(12) United States Patent
Gandini et al.

(10) Patent No.: US 12,174,179 B2
(45) Date of Patent: *Dec. 24, 2024

(54) DEVICES AND METHODS FOR DETECTION AND QUANTIFICATION OF IMMUNOLOGICAL PROTEINS, PATHOGENIC AND MICROBIAL AGENTS AND CELLS

(71) Applicants: Alberto Gandini, Katy, TX (US); James F. Antaki, Ithaca, NY (US); Byron Wang Chuan, Pittsburgh, PA (US); Joie N. Marhefka, Pittsburgh, PA (US); Juha-Pekka Mattila, Pearland, TX (US); Eliseo Salas, Stone Mountain, GA (US)

(72) Inventors: Alberto Gandini, Katy, TX (US); James F. Antaki, Ithaca, NY (US); Byron Wang Chuan, Pittsburgh, PA (US); Joie N. Marhefka, Pittsburgh, PA (US); Juha-Pekka Mattila, Pearland, TX (US); Eliseo Salas, Stone Mountain, GA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 1422 days.

This patent is subject to a terminal disclaimer.

(21) Appl. No.: 16/700,021

(22) Filed: Dec. 2, 2019

(65) Prior Publication Data
US 2020/0110081 A1 Apr. 9, 2020

Related U.S. Application Data

(60) Continuation-in-part of application No. 15/666,918, filed on Aug. 2, 2017, now Pat. No. 10,495,634, (Continued)

(51) Int. Cl.
*G01N 33/543* (2006.01)
*B01L 3/00* (2006.01)

(52) U.S. Cl.
CPC ...... *G01N 33/54326* (2013.01); *B01L 3/5027* (2013.01); *Y02A 50/30* (2018.01)

(58) Field of Classification Search
CPC ............. G01N 33/543; G01N 33/541; G01N 33/54326; G01N 33/54306;
(Continued)

(56) References Cited

U.S. PATENT DOCUMENTS

| 4,756,884 A | * | 7/1988 | Hillman | ................. B29C 66/54 366/DIG. 3 |
| 7,479,393 B2 | * | 1/2009 | Noetzel | ................ G01N 33/721 436/66 |

FOREIGN PATENT DOCUMENTS

KR 20100090957 * 8/2010 ........... G01N 33/553

* cited by examiner

*Primary Examiner* — Christopher L Chin
(74) *Attorney, Agent, or Firm* — ACKER WOOD IP LAW, LLC; Gaven R. Acker Wood

(57) ABSTRACT

The present invention provides microfluidic pScreen™ devices for quantifying the concentration of DNA fragments in a liquid sample by using magnetic-responsive silica micro-beads and nonmagnetic-responsive silica micro-beads. The devices of the present invention allow for rapid, simple and inexpensive quantification of DNA fragment concentration in a sample. The devices do not require complex instrumentation and can be performed in less than three minutes. Moreover, they are compatible with complex samples including, without limitation, unpurified PCR amplification products, and thus can be expected to seamlessly integrate into various common molecular biology techniques and workflows.

6 Claims, 32 Drawing Sheets

Related U.S. Application Data which is a division of application No. 14/148,010, filed on Jan. 6, 2014, now Pat. No. 9,753,029, which is a continuation-in-part of application No. 13/862,899, filed on Apr. 15, 2013, now Pat. No. 8,623,596, which is a continuation of application No. 13/684,618, filed on Nov. 26, 2012, now Pat. No. 8,445,192, which is a continuation-in-part of application No. 13/590,859, filed on Aug. 21, 2012, now abandoned.

(60) Provisional application No. 61/539,210, filed on Sep. 26, 2011.

(58) Field of Classification Search
CPC ........... G01N 33/54313; G01N 33/581; G01N 15/00; G01N 33/5302; G01N 35/0098; G01N 21/293; B01L 2300/0864; B01L 3/502761; B01L 3/502723; B01L 3/5085; B01L 3/5027; B01L 2200/0684; Y02A 50/30
USPC ....... 435/6.19, 5, 2; 422/504, 507, 502, 506, 422/68.1, 9, 99, 100, 101, 102; 436/63, 436/66, 67, 174, 175, 177, 178, 179, 180
See application file for complete search history.

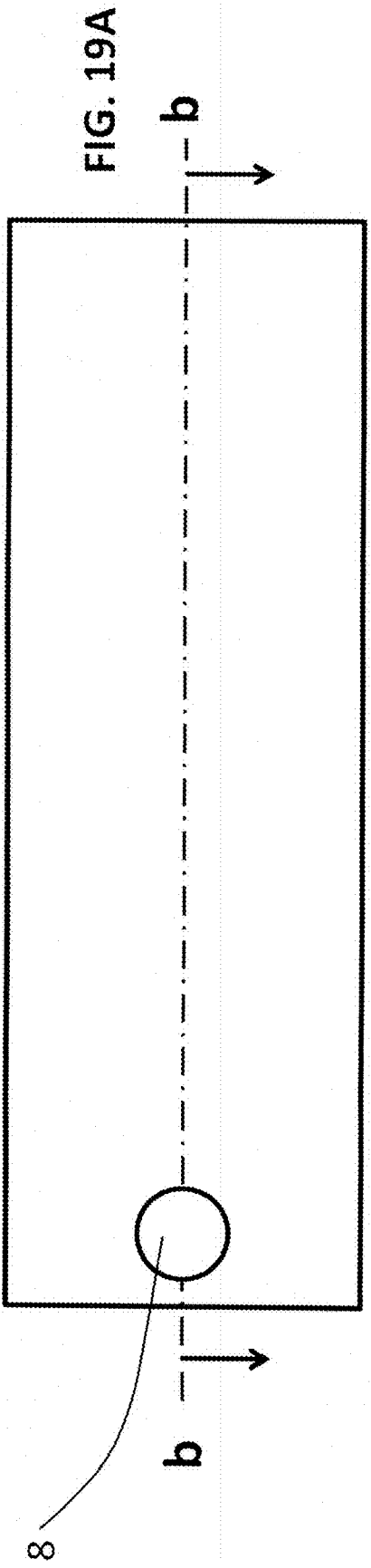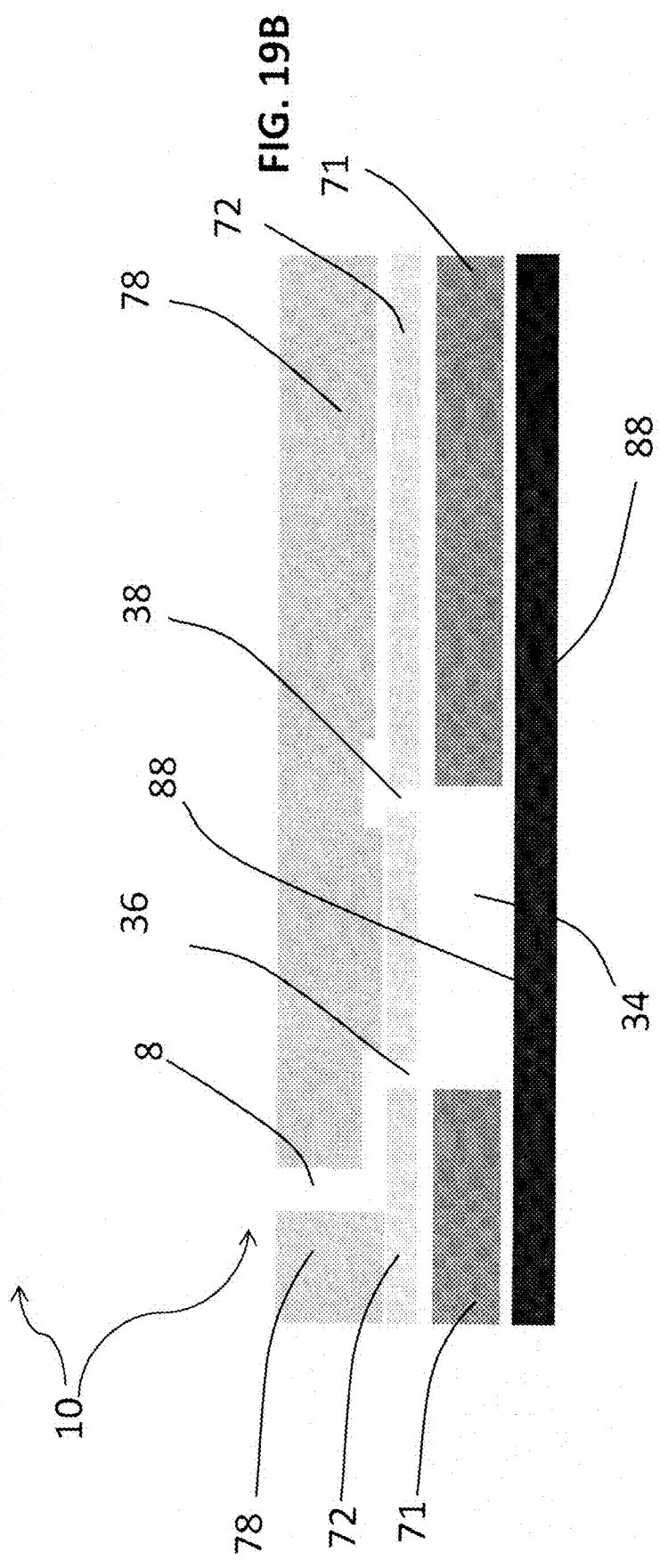

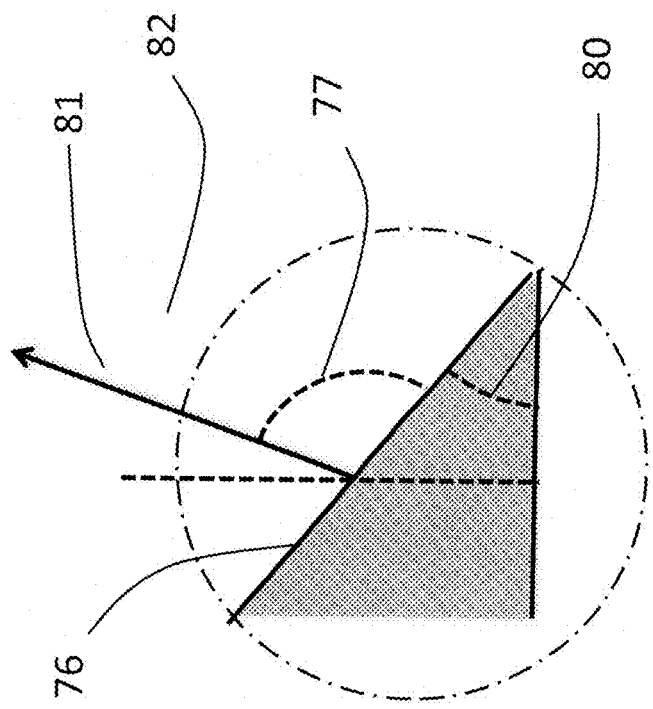
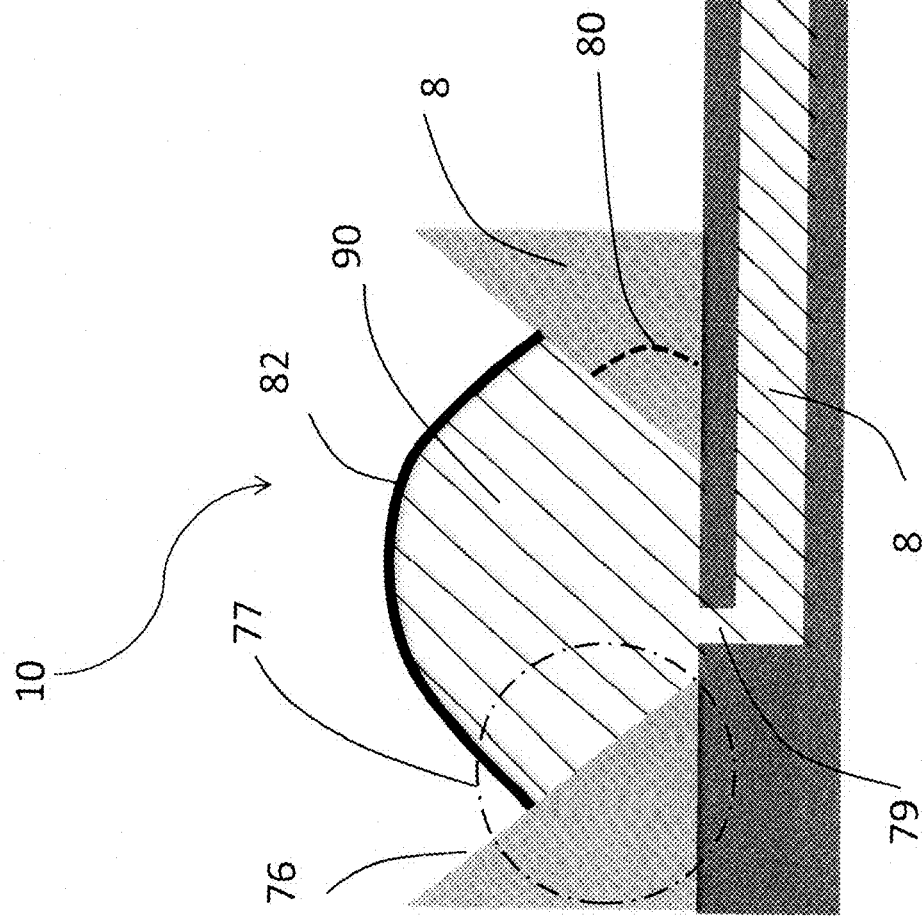
FIG. 20B
FIG. 20A

DEVICES AND METHODS FOR DETECTION AND QUANTIFICATION OF IMMUNOLOGICAL PROTEINS, PATHOGENIC AND MICROBIAL AGENTS AND CELLS

CROSS REFERENCE TO RELATED APPLICATIONS

The present application is a continuation-in-part of U.S. patent application Ser. No. 15/666,918, filed Aug. 2, 2017, which is a continuation of U.S. patent application Ser. No. 14/148,010, filed Jan. 6, 2014, which is a continuation-in-part of U.S. patent application Ser. No. 13/862,899, filed Apr. 15, 2013, now U.S. Pat. No. 8,623,596, which is a continuation application of U.S. patent application Ser. No. 13/684,618, filed Nov. 26, 2012, now U.S. Pat. No. 8,445,192, issued May 21, 2013, which is a continuation-in-part application of U.S. patent application Ser. No. 13/590,859, filed Aug. 21, 2012, which claims priority to U.S. Provisional Patent Application No. 61/539,210, filed Sep. 26, 2011, all of which are incorporated by reference herein in their entirety.

FIELD OF THE INVENTION

The present invention relates to the field of immunoassay and microfluidic devices and, in particular, to a point-of-care diagnostic method and device for the detection and quantification of magnetic-responsive micro-beads conjugated with proteins, cells and microbial agents dispersed in a liquid sample.

BACKGROUND OF THE INVENTION

Current immunoassay technologies for the detection and quantification of proteins rely on the specificity of the chemical interaction between antigens and antigen-specific antibodies. These tests may be classified into two main groups: laboratory based-tests and point-of-care (POC) tests. Laboratory-based tests are sensitive and accurate, but require a laboratory setting and skilled technicians. POC tests are designed to be used in the field and require limited training, but they are far less sensitive and accurate with most POC tests providing only binary positive/negative or semi-quantitative results.

All current immunoassay technologies involve the formation of an antigen-antibody complex. The detection of the complex indicates the presence of a targeted analyte in a sample. The antigen-antibody complex is detected by measuring the emission and/or reflection of light by the complex, when fluorescent-tagged antigen-specific antibodies are employed, or in the case in which antibody-coated micro-beads are used, by measuring the emission and/or reflection of light, or the magnetic moment of the micro-beads forming the antigen-bead complex. In all cases, optical or magnetic detectors and electronic readers are required.

For example, the simplest, best known and widely used POC diagnostic assay is the lateral flow assay, also known as the immunochromatic test. In this test, the targeted analyte is bound to an analyte-specific antibody linked to latex or gold nanoparticles. The presence of the analyte in the sample then is revealed by the formation of a visible band, or line, which results from the agglutination or accumulation of the analyte-antibody-linked complex. The band typically is visible macroscopically to the naked eye. Devices to increase the assay's sensitivity have been developed which can read color changes with microscopic sensitivity. Fluorescent or magnetic-labeled particles also have been used. In these cases, however, electronic readers to assess test results are needed. Thus, although sensitivity of the assay may increase, the cost and complexity of the assay also increases.

In recent years, antibody-coated micro-beads have been increasingly used for the separation and detection of proteins. In the field of immunoassay diagnostics, the concentration of micro-beads is a proxy for the concentration of targeted proteins in a sample. In these applications, it is necessary to identify the concentration of micro-beads in the sample solution. The micro-beads may be made magnetically responsive by adding a magnetic core or layer to a polymer bead. The micro-beads then may be coated with a variety of molecules and proteins, referred to as ligands, which serve the purpose of binding the targeted antigen via an antibody-antigen interaction. In addition, fluorescent dyes can be incorporated into the micro-beads making them optically detectable. Recently, a diagnostic test for the protein troponin using magnetic micro-beads has been proposed by Dittmer et al. (Philips Research Europe). In this assay, micro-beads coated with anti-troponin antibody are immobilized via antibody-troponin-antibodies on the surface of a micro-well with the aid of an applied magnetic field. The number of antibody-troponin-antibodies is measured by illuminating the bottom of the well and measuring the light reflected by the immobilized micro-beads with an optical receiver. Methods for the detection of E. coli also have been developed using immuno-magnetic micro-beads. In this case, the bacteria in the sample are measured by detecting time-resolve fluorescence.

While micro-bead technology has matured in the last decade, the technology to quantify micro-bead concentration has lagged behind. Current methods include manual microscopes and automatic or semi-automatic cell counters. Typically, micro-bead counting using a microscope involves the manual, and often tedious, counting of beads through a microscope objective. This method requires skilled technicians in a laboratory setting, is time consuming and is subject to a technician's interpretation. Cell counters require photo sensors to detect micro-beads automatically by measuring the light reflection of a laser beam hitting the micro-bead's surface. Cell counters, while accurate, are expensive and also require skilled technicians in sophisticated laboratory settings. Lab-on-a-chip devices to detect and measure the concentration of protein-coated micro-bead concentration also have been developed. These devices, however, rely on traditional approaches, i.e., light reflection and detection using micro-scale light and photo sensors and micro-scale magneto-resistance magnetometers. Thus, while greatly reducing the need for a laboratory setting and equipment, lab-on-a-chip devices still require electrical readers and transducers. In addition, these devices typically include handset and consumable components, resulting in increased manufacturing, calibration and maintenance costs. Thus, these devices have limited applications in the field of POC immunoassay diagnostics.

In addition to current immunoassay technologies which involve the formation of an antigen-antibody complex, quantification of deoxyribonucleic acid (DNA) is a fundamental step in many molecular biology workflows. Whether quantifying isolated DNA fragments, amplified segments from Polymerase Chain Reaction (PCR), or library and cloning components, an accurate determination of the concentration of DNA fragments is important for experimental design and overall success.

Multiple methods to measure DNA concentration currently are available. These include optical methods, such as measuring the amount of UV radiation absorbed by the constituent nucleotides or the intensity of fluorescence emission following addition of an intercalating dye, as well as the comparison of an unknown sample against DNA standards of known concentration using gel electrophoresis or real-time PCR. Each of the methods have their advantages and disadvantages with regard to sensitivity, assay time, need of dedicated instrumentation/reagents, and susceptibility to interference from contaminants.

Thus, there exists a need for a POC immunoassay device which has the sensitivity and specificity of laboratory-based immunoassay tests while being simple to use and low cost, as well as for methods to detect and quantify magnetic-responsive micro-bead concentration in a sample specimen. In addition, there exists a need for a POC device to measure DNA fragment concentration which has the sensitivity and specificity of laboratory-based devices and methods for measuring DNA concentration.

SUMMARY OF THE INVENTION

The pScreen™ microfluidic immunoassay device, based on the inventions disclosed herein, fulfills all of the above-described needs in a single device. The detection and quantification of an unknown concentration of analyte in a liquid sample is obtained by exploiting the fluid-dynamic properties of magnetic-responsive micro-beads in liquid solution rather than using optical effects or magnetic field sensing as in current technologies. The unknown concentration of the target analyte is derived by measuring the differential flow rate between the sample flow in two micro-channels, one of which is under the influence of an applied magnetic field gradient. The present invention significantly reduces the cost and complexity of current laboratory-based immunoassay diagnostic tests, and greatly increases one thousand-fold the sensitivity of lateral flow tests, while maintaining the specificity and accuracy of laboratory-based tests, and the ability to detect targeted antigen concentration over a predefined range.

In an embodiment of the present invention, there is provided a method of detecting and quantifying the concentration of magnetic-responsive micro-beads in a fluid. The method comprises measuring flow rate (Qm) of a fluid in at least one test micro-channel (Cm) exposed to a magnetic field gradient with flow rate (Qo) of the fluid in a calibration micro-channel (Co) not exposed to a magnetic field gradient, in which the micro-channels are kept at an equal and constant pressure, calculating the ratio Qm/Qo, the difference Qo−Qm, and the ratio $(Qo-Qm)^p/(Qm)^q$, wherein p and q are derived through a calibration process, wherein the ratios Qm/Qo and $(Qo-Qm)^p/(Qm)^q$ are a proxy for the number of magnetic-responsive micro-beads in the fluid, and then quantifying the concentration of magnetic-responsive micro-beads in the fluid. The presence of magnetic-responsive micro-beads in the at least one test micro-channel which is exposed to the magnetic field gradient causes flocculation of the magnetic-responsive micro-beads in the fluid which reduces the flow rate of the fluid through the at least one test micro-channel.

In another embodiment, there is provided a method for detecting and quantifying concentration of an analyte in a liquid sample. The method comprises adding a liquid sample to a liquid sample inlet of a reaction chamber. The reaction chamber has adsorbed on its surface a plurality of immobilized antigen-specific antibodies (Ab1) specific to an analyte. The surface of the reaction chamber also has a plurality of magnetic-responsive micro-beads desiccated thereon, in which each of the plurality of magnetic-responsive micro-beads is coated with an antigen-specific antibody (Ab2) specific to the analyte. The method comprises having the liquid sample incubate within the reaction chamber, which causes rehydration of the plurality of antibody-coated magnetic-responsive micro-beads as the liquid sample is added and agitated in the reaction chamber, which rehydration disperses the antibody-coated magnetic-responsive micro-beads in the liquid sample, binding the rehydrated antibody-coated magnetic-responsive micro-beads as well as the antigen-specific antibodies immobilized on the surface of the reaction chamber to any analyte present in the liquid sample to form Ab1-analyte-Ab2-coated magnetic-responsive micro-bead complexes on the surface of the reaction chamber, having the liquid sample containing any unbound antibody-coated magnetic-responsive micro-beads exit the reaction chamber through a chamber outlet and transfer through a continuous fluid connection to a micro-channel splitter which bifurcates to form a calibration micro-channel (Co) and at least one test micro-channel (Cm). The at least one test micro-channel and the calibration micro-channel are kept at an equal and constant pressure. The calibration micro-channel is in continuous fluid connection with a graduated column, and the at least one test micro-channel is in continuous fluid connection with at least one graduated column. Each of the graduated columns has a graduated scale thereon. The method comprises measuring flow rate (Qm) of the liquid sample in the at least one test micro-channel exposed to a magnetic field gradient with flow rate (Qo) of the fluid in the calibration micro-channel not exposed to a magnetic field gradient, in which the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel, calculating the ratio Qm/Qo, the difference Qo−Qm, and the ratio $(Qo-Qm)^p/(Qm)^q$, wherein p and q are derived through a calibration process, wherein the ratios Qm/Qo and $(Qo-Qm)^p/(Qm)^q$ are a proxy for the number of magnetic-responsive micro-beads in the liquid sample, which is a proxy for the concentration of analyte in the liquid sample, and then quantifying the concentration of analyte in the liquid sample.

In another embodiment, there is provided a single use, portable, lab-on-card microfluidic pScreen™ magnetic-responsive micro-bead concentration counter device for detecting and quantifying the concentration of magnetic-responsive micro-beads in a liquid sample. The microfluidic device is comprised of a liquid sample inlet defined by an opening for accepting a liquid sample that contains a quantity of magnetic-responsive micro-beads. The liquid sample inlet is in continuous fluid connection with a flow resistor, which is in continuous fluid connection with a micro-channel splitter which bifurcates to form a calibration micro-channel (Co) and at least one test micro-channel (Cm). The calibration micro-channel and the at least one test micro-channel are kept at an equal and constant pressure. The calibration micro-channel is in continuous fluid connection with a graduated column, and the at least one test micro-channel is in continuous fluid connection with at least one graduated column. The at least one test micro-channel is exposed to a magnetic field gradient, which causes flocculation of the magnetic-responsive micro-beads in the at least one test micro-channel. The flocculation reduces the flow rate (Qm) of the liquid sample in the at least one test micro-channel compared to the flow rate (Qo) of the liquid sample in the calibration micro-channel. Each of the graduated columns has a graduated scale thereon which provides a read-out of the total volume of the liquid sample collected in each of the graduated columns, in which the total volume of the liquid sample collected in the at least one test micro-channel graduated column indicates the concentration of magnetic-responsive micro-beads in the liquid sample.

In another embodiment of the invention, there is provided a single use, portable, lab-on-card microfluidic pScreen™ immunoassay device for detecting and measuring an analyte in a liquid sample. The microfluidic pScreen™ immunoassay device comprises a liquid sample inlet defined by an opening for accepting the liquid sample. The liquid sample inlet is in continuous fluid connection with a flow resistor channel, which is in continuous fluid connection with an assay inlet of a reaction chamber. The reaction chamber has adsorbed on its surface a plurality of immobilized antigen-specific antibodies (Ab1) specific to an analyte, as well as having a plurality of magnetic-responsive micro-beads desiccated thereon. Each of the plurality of magnetic-responsive micro-beads is coated with an antigen-specific antibody (Ab2) specific to the analyte. Flow of the liquid sample through the reaction chamber rehydrates the plurality of antibody-coated magnetic-responsive micro-beads which disperses into the liquid sample. Any analyte present in the liquid sample binds to the dispersed antibody-coated magnetic-responsive micro-beads as well as to the antigen-specific antibodies immobilized on the surface of the reaction chamber to form Ab1-analyte-Ab2-coated magnetic-responsive micro-bead complexes. Any unbound antibody-coated magnetic-responsive micro-beads exit the reaction chamber through an assay outlet, which is in continuous fluid connection with a micro-channel splitter that bifurcates to form a calibration micro-channel (Co) and at least one test micro-channel (Cm), which are kept at an equal and constant pressure. The calibration micro-channel is in continuous fluid connection with a graduated column, and the at least one test micro-channel in continuous fluid connection with at least one graduated column. The at least one test micro-channel is exposed to a magnetic field gradient, which causes flocculation of the magnetic-responsive micro-beads in the at least one test micro-channel. The flocculation reduces the flow rate (Qm) of the liquid sample in the at least one test micro-channel compared to the flow rate (Qo) of the liquid sample in the calibration micro-channel. Each of the graduated columns has a graduated scale thereon which provides a read-out of the total sample volume collected in each of the graduated columns, in which the total sample volume collected in the at least one test micro-channel graduated column indicates the concentration of analyte in the liquid sample.

In another embodiment, there is provided a method for detecting and quantifying concentration of an analyte in a liquid sample using a single use, portable, lab-on-card microfluidic pScreen™ immunoassay device having a plurality of reaction chambers and a system of secondary micro-channels. The method comprises adding a liquid sample to an immunoassay microfluidic device, the microfluidic device having a liquid sample inlet in continuous fluid connection with a liquid sample inlet manifold micro-channel that is in continuous fluid connection with a plurality of reaction chambers, each of the plurality of reaction chambers having adsorbed on its surface a plurality of immobilized antigen-specific antibodies (Ab1) specific to an analyte each of the plurality of reaction chambers has adsorbed on its surface a plurality of immobilized antigen-specific antibodies (Ab1) specific to an analyte, wherein the surface of each of the reaction chambers also has a plurality of magnetic-responsive micro-beads deposited thereon, each of the plurality of magnetic-responsive micro-beads coated with an antigen-specific antibody (Ab2) specific to the analyte; incubating the liquid sample within the plurality of reaction chambers, which causes rehydration of the plurality of antibody-coated magnetic-responsive micro-beads, which rehydration disperses the antibody-coated magnetic-responsive micro-beads in the liquid sample; binding the rehydrated antibody-coated magnetic-responsive micro-beads as well as the antigen-specific antibodies immobilized on the surface of each of the reaction chambers to any analyte present in the liquid sample to form Ab1-analyte-Ab2-coated magnetic-responsive micro-bead complexes on the surface of each of the reaction chambers; having the liquid sample containing any unbound antibody-coated magnetic-responsive micro-beads exit the plurality of reaction chambers through outlet manifold micro-channels which is in continuous fluid connection with a connector micro-channel, wherein one outlet manifold micro-channel also is in continuous fluid connection with a delay micro-channel, the delay micro-channel also in continuous fluid connection with the connector micro-channel, wherein the connector micro-channel is in continuous fluid connection with a terminal flow splitter micro-channel that bifurcates to form a calibration micro-channel (Co) and at least one test micro-channel (Cm), wherein each of the outlet manifold micro-channels terminates in a passive valve, each of the passive valves substantially stopping, for a given period of time, the flow of the liquid sample from moving forward into the connector micro-channel; measuring the volume, Vm, of the liquid sample passing through the at least one test micro-channel exposed to a magnetic field gradient, in which the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel, and the volume of the liquid sample passing through the calibration micro-channel, Vo, not exposed to a magnetic field gradient; calculating the ratio Vm/Vo, the difference Vo−Vm, and the ratio $(Vo-Vm)^p/(Vm)^q$, wherein p and q are derived through a calibration process, wherein the ratios Vm/Vo and $(Vo-Vm)^p/(Vm)^q$ are a proxy for the number of magnetic-responsive micro-beads in the liquid sample, which is a proxy for the concentration of analyte in the liquid sample; and quantifying the concentration of analyte in the liquid sample.

In another embodiment of the invention, there is provided a single use, portable, lab-on-card microfluidic pScreen™ immunoassay device for detecting and quantifying an analyte in a liquid sample having a plurality of reaction chambers and a system of secondary micro-channels. The microfluidic pScreen™ immunoassay device comprises a liquid sample inlet, which is in continuous fluid connection with a liquid sample inlet manifold micro-channel, which is in continuous fluid connection with a plurality of reaction chambers. Each of the reaction chambers has an outlet manifold micro-channel where fluid exits the chambers. Each of the plurality of reaction chambers has adsorbed on its surface a plurality of immobilized antigen-specific antibodies (Ab1) specific to an analyte, and a plurality of magnetic-responsive micro-beads deposited thereon. Each of the plurality of magnetic-responsive micro-beads is coated with an antigen-specific antibody (Ab2) specific to the analyte. When the liquid sample flows through the plurality of reaction chambers, the plurality of antibody-coated magnetic-responsive micro-beads disperses in the liquid sample and binds to any analyte present in the liquid sample. Any analyte present in the liquid sample also binds to the antigen-specific antibodies immobilized on the surface of the plurality of reaction chambers to form Ab1-analyte-Ab2-coated magnetic-responsive micro-bead complexes. Any unbound antibody-coated magnetic-responsive micro-beads exit each of the plurality of reaction chambers via the outlet manifold micro-channels. Each of the outlet manifold micro-channels terminates in a passive valve. The liquid sample flow is substantially stopped for a period of time at each of the passive valves, wherein the substantial stoppage of flow allows the analyte to incubate with the Ab1 and Ab2 antibodies in the plurality of reaction chambers. A primary flow splitter micro-channel is in continuous fluid connection with one of the outlet manifold micro-channels, and the primary flow splitter micro-channel is in continuous fluid connection with a delay micro-channel. The delay micro-channel is in continuous fluid connection with a connector micro-channel. The passive valves also are in continuous fluid connection with the connector micro-channel. The connector micro-channel is in continuous fluid connection with a terminal flow splitter micro-channel which bifurcates to form a calibration micro-channel (Co) and at least one test micro-channel (Cm), which are kept at an equal and constant pressure. The calibration micro-channel is in continuous fluid connection with one or more calibration graduated columns, and the at least one test micro-channel is in continuous fluid connection with one or more test graduated columns. The test micro-channel is exposed to a magnetic field gradient, which causes flocculation of the magnetic-responsive micro-beads in the at least one test micro-channel. The flocculation reduces the flow rate (Qm) of the liquid sample in the at least one test micro-channel compared to the flow rate (Qo) of the liquid sample in the calibration micro-channel. The volume of liquid collected in the one or more calibration graduated columns, Vo, and in the one or more test graduated columns, Vm, are a proxy for the concentration of the analyte in the liquid sample.

Each of the reaction chambers, other than the reaction chamber that is in continuous fluid connection with the delay micro-channel, is in continuous fluid connection with a secondary flow splitter micro-channel. Each secondary flow splitter micro-channel is in continuous fluid connection with the outlet manifold micro-channel and with an appendix micro-channel. Each of the appendix micro-channels terminates in a vent port that is open to atmospheric pressure.

Each passive valve has three sharp edges and one continuous surface comprised of a sealing layer. The passive valves serve to substantially stop the liquid sample flow for about 30 seconds to about 5 minutes due to the three sharp edges which intersects with the connector micro-channel. After this time, the passive valves burst sequentially so that the liquid sample resumes flowing into the connector micro-channel. In contrast, the liquid sample flows freely through the delay micro-channel and the appendix micro-channels via capillary action. This free flow of liquid sample reduces the pressure gradient across the passive valves enough so that the passive valves work to substantially stop the flow of the liquid sample across the passive valves.

In accordance with the invention, the magnetic-responsive micro-beads are deposited on the surface of each of the reaction chambers by deposition of a micro-bead buffer solution containing the micro-beads dispersed therein. The micro-bead buffer solution is comprised of phosphate buffered saline. The micro-beads are deposited in nano-drops, in which each nano-drop has a volume of about 3 nl to 60 nl.

In accordance with the invention, mass density of the micro-bead buffer solution is increased to match mass the density of the micro-beads by adding additives to the micro-bead buffer solution. The additives may include, without limitation, heavy water, glycerol, sucrose, polyethylene glycol, or a combination of two or more of the additives.

In accordance with the invention, all of the micro-channels of the device may be coated with a protein-free blocking solution which creates a hydrophilic film on the surface of the micro-channels, which hydrophilic film decreases the liquid sample contact angle, increases liquid sample flow rate, and decreases assay time.

In accordance with the invention, the liquid sample inlet can have a conical shape and a super-hydrophobic surface in order to create a convex meniscus which creates pressure within the liquid sample that is greater than the atmospheric pressure so that a pressure gradient is created which favors the flow of the liquid sample through the device.

In accordance with the invention, the micro-channel splitter of the microfluidic device bifurcates to form one test micro-channel and one calibration micro-channel. In another embodiment of the invention, the micro-channel splitter of the microfluidic device bifurcates to form three test micro-channels and one calibration micro-channel, in which each of the three test micro-channels is in continuous fluid connection with one graduated column. In another embodiment of the invention, the micro-channel splitter of the microfluidic device bifurcates to form four test micro-channels and one calibration micro-channel, in which the four test micro-channels merge to be in continuous fluid connection with one graduated column.

Liquid samples that can be assayed in accordance with the embodiments of the invention include, without limitation, water, plasma, serum, buffer solution, urine, whole blood, blood analogs, and liquid solutions from dilution of solid biological matter or other biological fluids.

Analytes that can be detected and quantified in accordance with the embodiments of the invention include, without limitation, proteins, protein fragments, antigens, antibodies, antibody fragments, peptides, RNA, RNA fragments, functionalized magnetic micro-beads specific to $CD^{4+}$, $CD^{8+}$ cells, malaria-infected red blood cells, cancer cells, cancer biomarkers such as prostate specific antigen and other cancer biomarkers, viruses, bacteria such as *E. coli* or other pathogenic agents.

The magnetic field gradient in accordance with the invention is generated from two magnets aligned lengthwise with the at least one test micro-channel and along opposite poles to expose the at least one test micro-channel to the magnetic field gradient. The at least one test micro-channel is located between a gap formed between the opposite poles of the magnets. In another embodiment, the magnetic field gradient is generated by one magnet and a magnetic-responsive structure positioned near the at least one test micro-channel.

In accordance with the invention, the magnetic field generated can range between about 0.05 Tesla (T) to about 0.5 T, and the magnetic field gradient that is generated can be about 10 T/m or greater.

The total sample volume collected in the calibration micro-channel graduated column serves as a control for parameters such as variation in viscosity between samples, level of hematocrit in blood samples, temperature and humidity fluctuations and sample volumes.

The present invention will be more fully understood from the following description of the invention and by reference to the figures and claims appended hereto.

In another embodiment, there is provided a microfluid device for quantifying the concentration of DNA fragments. The microfluid device comprises a sample inlet defined by an opening for accepting a liquid sample; a sealing layer; a reaction chamber; a micro-channel splitter; a calibration micro-channel; a test micro-channel; a control graduated column; a test graduated column; a venting hole located at the end of each of the graduated columns that is placed through the sealing layer; and a magnetic field gradient adjacent to the test micro-channel.

The liquid sample contains a mixture of magnetic-responsive silica micro-beads, nonmagnetic-responsive silica micro-beads, and an aliquot of a DNA fragment sample, wherein the liquid sample is placed on the inlet of the microfluidic device.

The presence of DNA fragments triggers the formation of large magnetic-responsive clusters, the magnetic-responsive clusters aggregating in proximity of the magnetic field gradient to produce a localized restriction, the restriction retarding flow of the liquid sample in the test column.

The concentration of the nonmagnetic-responsive silica micro-beads ranges from between 10 µg/µl and 60 µg/µL in the liquid sample; and the concentration of magnetic-responsive silica micro-beads ranges from between 1.0 µg/µl and 2.0 µg/µL in the liquid sample.

In an embodiment, the control graduated column and the test graduated column are connected to one another via a joining channel, and a venting hole located at the end of the control column is placed through the sealing layer to stop the flow in the test channel when the liquid flowing in the control column fills to a desired volume.

In another embodiment, there is provided a microfluid passive valve layout to stop the flow of liquid in a primary micro-channel when a control micro-channel fills to a desired volume. The microfluidic passive valve layout comprises a primary micro-channel, a control micro-channel, a joining channel connecting the control and the primary micro-channel, and a venting hole in the joining channel which is placed through the sealing layer, the venting hole placed such that the volume of liquid filling the control micro-channel is the desired amount.

BRIEF DESCRIPTION OF THE DRAWINGS

A fuller understanding of the invention can be gained from the following description when read in conjunction with the accompanying drawings in which:

FIGS. 8A, 8B and 8C are schematic illustrations of three different views of a reaction chamber of the pScreen™ immunoassay device, in which FIG. 8A shows the secondary antibody (Ab2)-coated magnetic-responsive micro-beads and primary antibody (Ab1)-capturing antibodies on the surface of the reaction chamber; FIG. 8B shows the Ab1-antigen-Ab2-magnetic-responsive micro-bead complexes immobilized on the surface of the chamber; and FIG. 8C shows unbound, i.e., free, Ab2-magnetic-responsive micro-beads reaching the assay outlet of the reaction chamber, according to the embodiments of the invention;

FIG. 19A is a schematic illustration of the pScreen™ immunoassay device showing the sample inlet and the device's longitudinal axis. FIG. 19B is a schematic illustration of a cross-section of the pScreen™ immunoassay device along the longitudinal axis at B-B, showing the two levels of the device, in accordance with the invention;

FIGS. 20A and 20B are schematic illustrations of the pScreen™ immunoassay device inlet, with FIG. 20A showing a cross-section of the inlet, and FIG. 20B showing an expanded view of the inlet contact angle and inlet cone angle, in accordance with the invention;

DETAILED DESCRIPTION OF THE INVENTION

As used herein, the terms "analyte" and "antigen" are meant to be interchangeable.

As used herein, the terms "calibration micro-channel(s)" and "control micro-channel(s)" are meant to be interchangeable.

As used herein, the terms "magnetic-responsive micro-beads," and "magnetic micro-beads" are meant to be interchangeable.

As used herein, the terms "microfluidic device" and "microfluidic card" are meant to be interchangeable.

Figure 1:
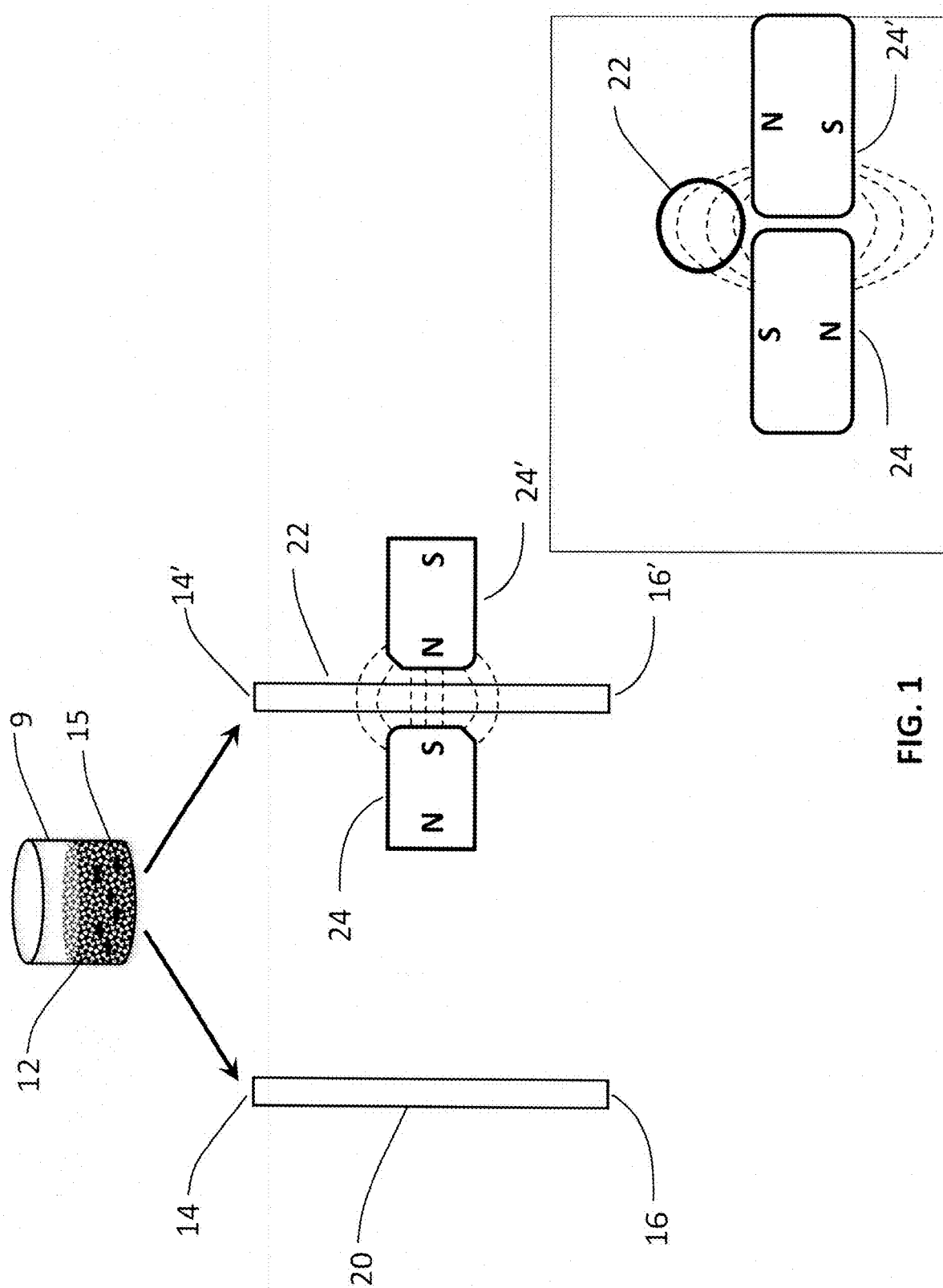
FIG. 1 is a schematic illustration of the method for determining the number of magnetic-responsive micro-beads in a fluid, in which the ratio between the flow rate in the calibration micro-channel (Co) and the test micro-channel (Cm) is measured, according to the embodiments of the invention.

The present invention provides a flow rate-based method for detecting and quantifying the concentration, i.e., number, of magnetic-responsive micro-beads in a fluid. The ratio, $Qm/Qo$, between the flow rate ($Qm$) in a test micro-channel ($Cm$) exposed to a localized high-gradient magnetic field, and the unperturbed flow rate ($Qo$) in a calibration, or control, micro-channel ($Co$) not exposed to the localized high-gradient magnetic field, is a monotonic function of the number of magnetic-responsive micro-beads flowing through the test micro-channel. That is:

$$Qm(N_m)/Qo = f(N_m) \qquad \text{Equation (1)}$$

where $Nm$ is the total number of magnetic-responsive micro-beads transported by the fluid into the localized high-magnetic field region. Both micro-channels are held at an equal and constant pressure. As shown in FIG. 1, a fluid 12 seeded with magnetic-responsive micro-beads 15 flows into two micro-channel inlets 14, 14' and out of two micro-channel outlets 16, 16'. The test micro-channel 22 on the right is exposed to a high-gradient magnetic field generated by two magnets 24, 24'. The magnets are positioned as shown in FIG. 1 and in the inset. In an embodiment, the magnetic field gradient is generated by one magnet and a magnetic-responsive structure (not shown) positioned near the test micro-channel 22. A magnetic-responsive structure may be made of a metallic material with ferromagnetic, super-paramagnetic or paramagnetic properties, such that upon application of an external magnetic field the magnetic-responsive structure generates an induced magnetic field. The structure is geometrically shaped, e.g., cylindrically-shaped, in order to generate a magnetic field gradient in the region occupied by the test micro-channel. Equation 1 applies to a wide range of magnetic-responsive micro-bead concentrations, ranging from about 50 micro-beads/µl to about $2 \times 10^6$ micro-beads/µl. The upper and lower limits, however, are a function of the micro-channels' size and magnetic field topology. Hence, both upper and lower limits may vary based on these parameters.

Because $f(Nm)$ is a monotonic function of $Nm$, it also holds that:

$$N_m = f^{-1}(Qm(N_m)/Qo) \qquad \text{Equation (2)}$$

Thus, according to Equation 2, the number of magnetic-responsive micro-beads in a given fluid is a monotonic function of the ratio $Qm/Qo$. Thus, the number of magnetic-responsive micro-beads can be determined by measuring the ratio $Qm/Qo$ in the two micro-channels, configured as shown in FIG. 1. In other words, the ratio $Qm/Qo$ is a specific proxy for the number of magnetic-responsive micro-beads in a given fluid.

The analytical form of the function depends on the geometry, i.e., length and inner diameter of the two micro-channels, magnetic field topology, and the size of the magnetic-responsive micro-beads. In addition, the difference $Q_o - Q_m$, and the ratio $(Q_o - Q_m)^p/(Q_m)^q$, where p and q are derived through a calibration process, are a proxy for the number of magnetic-responsive micro-beads in the fluid. The parameters p and q are obtained as followed. A solution containing a known concentration of micro-beads and of known volume is passed through the micro-channels and the flow rate Qm and Qo are measured. Then, a solution containing the same concentration of magnetic-responsive micro-beads but of larger volume similarly is passed through the micro-channels. This process is repeated several times. Then, the ratio $(Qo-Qm)^p/(Qm)^q$, with p and q set equal to 1, are plotted versus the volume of each sample. Using the well-known least square regression method, p and q are determined by enforcing the condition that the ratios $(Qo-Qm)^p/(Qm)^q$ versus sample volume form a horizontal straight line with slope equal to zero.

The present invention further provides a microfluidic pScreen™ magnetic-responsive micro-bead concentration counter device for detecting and quantifying magnetic-responsive micro-bead concentration in a liquid sample. This device leverages the previously described flow rate-based detection and quantification method.

Figure 2:
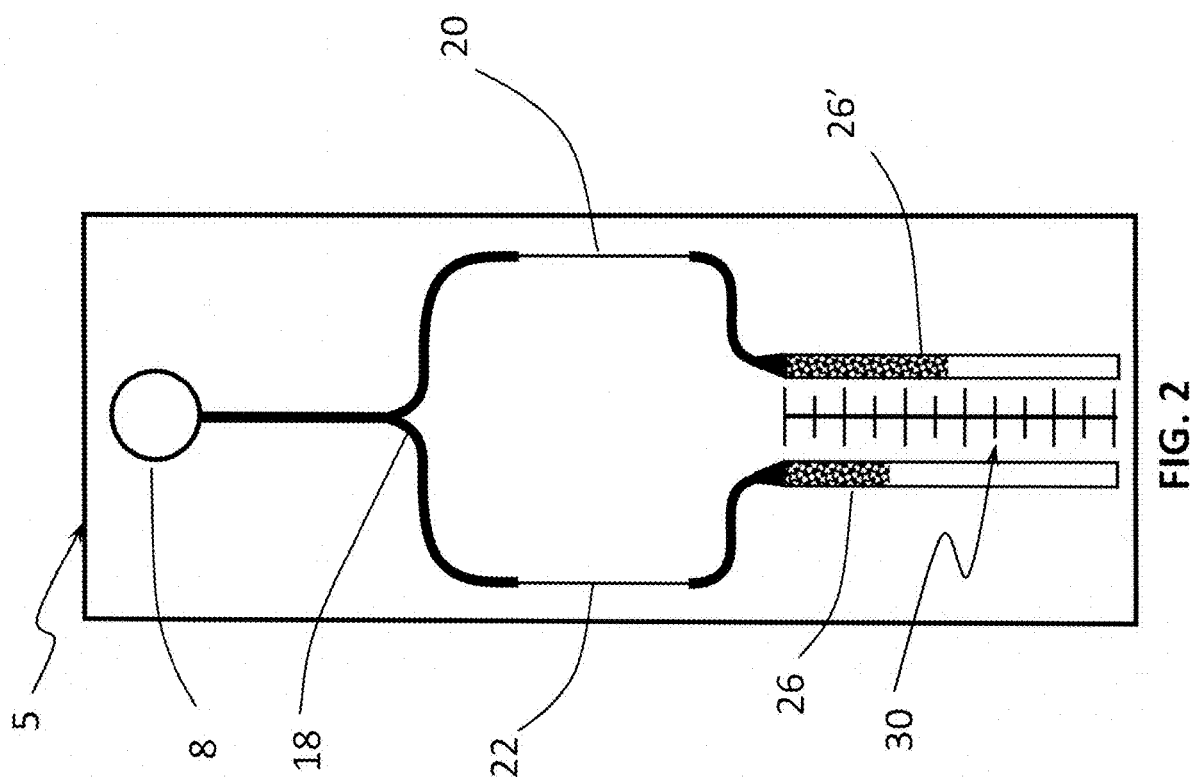
FIG. 2 is a schematic illustration of the microfluidic pScreen™ magnetic-responsive micro-bead concentration counter device, having one test micro-channel and one calibration micro-channel, according to the embodiments of the invention.
Figure 3:
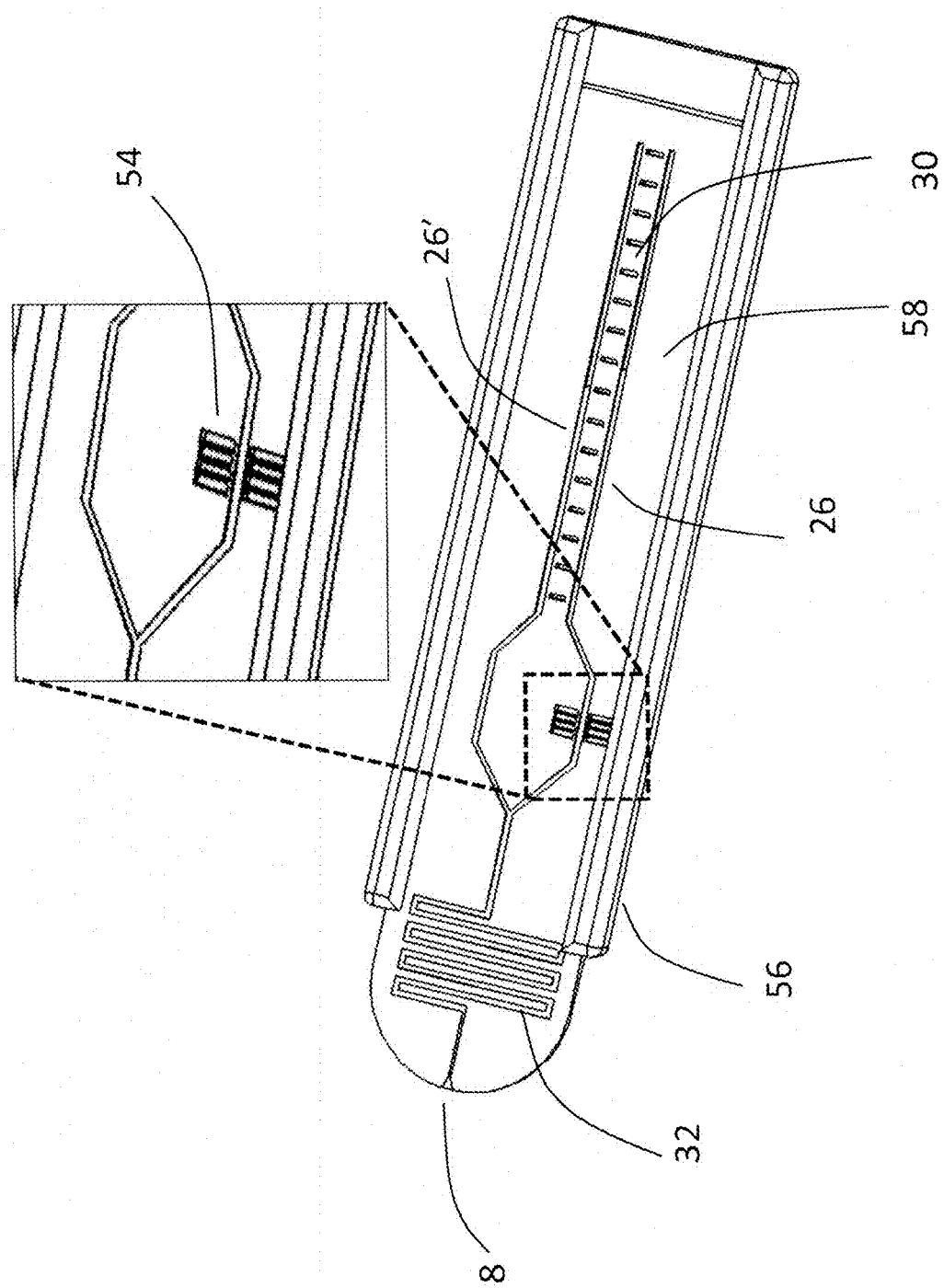
FIG. 3 is an artistic rendering of the microfluidic pScreen™ immunoassay device, according to the embodiments of the invention.

FIGS. 2 and 3 show the pScreen™ microfluidic device 5 for the detection and quantification of magnetic-responsive micro-beads in a liquid sample of the present invention. The microfluidic device 5 comprises a liquid sample inlet 8 in which a liquid sample, or specimen, which contains an unknown amount of magnetic-responsive micro-beads, is applied. From the liquid sample inlet 8, the liquid sample, self-propelled by capillary action, flows through a flow resistor 32 (shown in FIG. 3) and enters a micro-channel splitter 18. The micro-channel splitter 18 bifurcates into two smaller micro-channels: a calibration micro-channel 20 and a test micro-channel 22. The two micro-channels 20, 22 are identical in length and inner diameter (best shown in FIG. 2).

The concentration of magnetic-responsive micro-beads that can be detected and quantified using the methods and devices of the invention is about 50 micro-beads/µl to about $2 \times 10^6$ micro-beads/µl; and the diameter of the magnetic-responsive micro-beads is about 0.2 µm to about 20 µm. In an embodiment, the diameter of the magnetic micro-beads is about 4.0 µm.

In accordance with the invention, the test micro-channel and the calibration micro-channel are made of a capillary tube, in which the length of the capillary tube is about 0.2 cm to about 20 cm. In an embodiment, the length of the capillary tube is about 3.0 cm to about 7.5 cm. In another embodiment, the length of the capillary tube is about 1.5 cm.

In an embodiment, the length of the calibration micro-channel 20 and the test micro-channel 22 is about 0.2 cm to about 20 cm. In another embodiment, the length of the two micro-channels 20, 22 is about 3.0 cm to about 7.5 cm. In still another embodiment, the length of the two micro-channels 20, 22 is about 1.5 cm.

In an embodiment, the inner diameter of the calibration micro-channel 20 and the test micro-channel 22 is about 50 µm to about 500 µm. In another embodiment, the inner diameter of the two micro-channels 20, 22 is about 50 µm.

A magnetic field gradient is applied only to the test micro-channel 22. The magnetic field gradient is generated by small rare-earth (e.g., neodymium) permanent magnet and ferromagnetic (e.g., nickel, iron) pole structures (not shown) which serve as a magnetic concentrator 54 (shown in FIG. 3) specifically designed to concentrate the magnetic field, hence creating a high magnetic field gradient (of about 100 T/m). In the calibration channel 20, the liquid sample flows freely at a very low velocity (Reynolds number around 1) and shear rate range (1 to 400 $s^{-1}$). In the test micro-channel 22, the magnetic field gradient induces micro-bead flocculation if magnetic-responsive micro-beads are present in the sample. Even in very small concentrations, as low as <50 micro-beads/µl, the flow rate through the test micro-channel 22 will be reduced due to the formation of the magnetically-induced micro-bead flocculation. After flowing through the calibration and test micro-channels 20, 22, a volume of liquid sample is collected in two graduated columns 26, 26', both of equal size and volume.

Each graduated column 26, 26' has a graduated scale thereon 30 which provides an easy to interpret read-out system of the total sample volume collected in each graduated column 26, 26'. The graduated columns' 26, 26' length and cross section, as well as the respective scales 30 thereon, are designed to be visible to the naked eye. Unlike current POC read-out devices, the read-out system of the microfluidic device of the present invention does not require electrical transducers and/or sensors. As shown in FIGS. 2 and 3, both graduated columns 26, 26' are clearly visible. As shown in FIG. 3, the microfluidic device 5 may be configured in a cartridge 58 which fits into a holder 56. The read-out obtained by the microfluidic device 5 can be determined at any time by direct comparison of the fluid in the two graduated columns 26, 26'.

Referring now to FIG. 2, the micro-channel configuration provides for the concentration of micro-beads to be a monotonic function only of the volumes Vo and Vm (Vo and Vm are the volumes collected at the micro-channel outlets 16, 16' of the calibration micro-channel 20 (Co) and test micro-channel 22 (Cm), respectively; shown in FIG. 1). This approach allows the user to read out the result provided by the pScreen™ microfluidic device of the present invention at any time while the assay is running or at any time after the assay has been completed.

Given the relationship in Equation (1), and because the flow rate in the calibration micro-channel 20 is constant and the magnetic-responsive micro-beads are uniformly distributed in the sample fluid, and by definition ρ=dN/dV and dV=Qdt, where N is the number of micro-beads, Q the flow rate, and V the fluid volume, the below equations are satisfied at any time instances:

$$t = \int_0^{N_o} \frac{dN'}{\rho Q_0} = \frac{N_0}{\rho Q_0}, \quad \text{Equation (3)}$$

$$t = \int_0^{N_m} \frac{dN'}{\rho Q_m}. \quad \text{Equation (4)}$$

where, t is the time, ρ is the magnetic-responsive micro-bead concentration in the sample specimen 12, Qo and Qm are the flow rates in the calibration and test micro-channels 20, 22, respectively, No and Nm is the number of magnetic-responsive micro-beads passing through the calibration and test micro-channels 20, 22, respectively, and the prime symbol inside the integral, dN', indicates, according to standard convention, that the integral operation is computed on N variable It thus follows that:

$$N_0 = g(N_m), \text{ with:} \quad \text{Equation (5)}$$

$$g(N) \equiv \int_0^{N_m} \frac{dN'}{Q(N)}, \text{ and: } Q = \frac{Q_m}{Q_0}.$$

Thus:

$$N_m = g^{-1}(N_0). \quad \text{Equation (6)}$$

-continued

Since, $$N_0 = \rho V_0, \text{ and } N_m = \rho V_m,$$  Equation (7)

we have that:

$$\rho V_m = g^{-1}(\rho V_0)$$

Hence: $\rho = F(V_0, V_m)$.  Equation (8)

Thus, the pScreen™ microfluidic device of the present invention provides a comparative read-out system in which the magnetic-responsive micro-bead concentration, ρ, is a monotonic function of only Vm, the volume flowing through the test micro-channel 22 where the magnetic-induced flocculation forms and Vo, the volume flowing through the calibration micro-channel 20 without the magnetic-induced flocculation.

The comparative read-out system of the pScreen™ microfluidic device of the present invention greatly simplifies the detection and quantification of magnetic-responsive micro-bead concentration in a liquid sample. In addition, this comparative read-out system has the significant advantage of virtually eliminating common-mode error (with the calibration graduated column 26 acting as a control), such as variation in viscosity between samples, level of hematocrit in blood samples, temperature and humidity fluctuation of the test environment, and sample volume. The pScreen™ microfluidic device of the present invention thus provides a stand-alone device for the detection and quantification of magnetic-responsive micro-bead concentration in liquid samples over a wide range of concentrations and micro-bead sizes.

Figure 4:
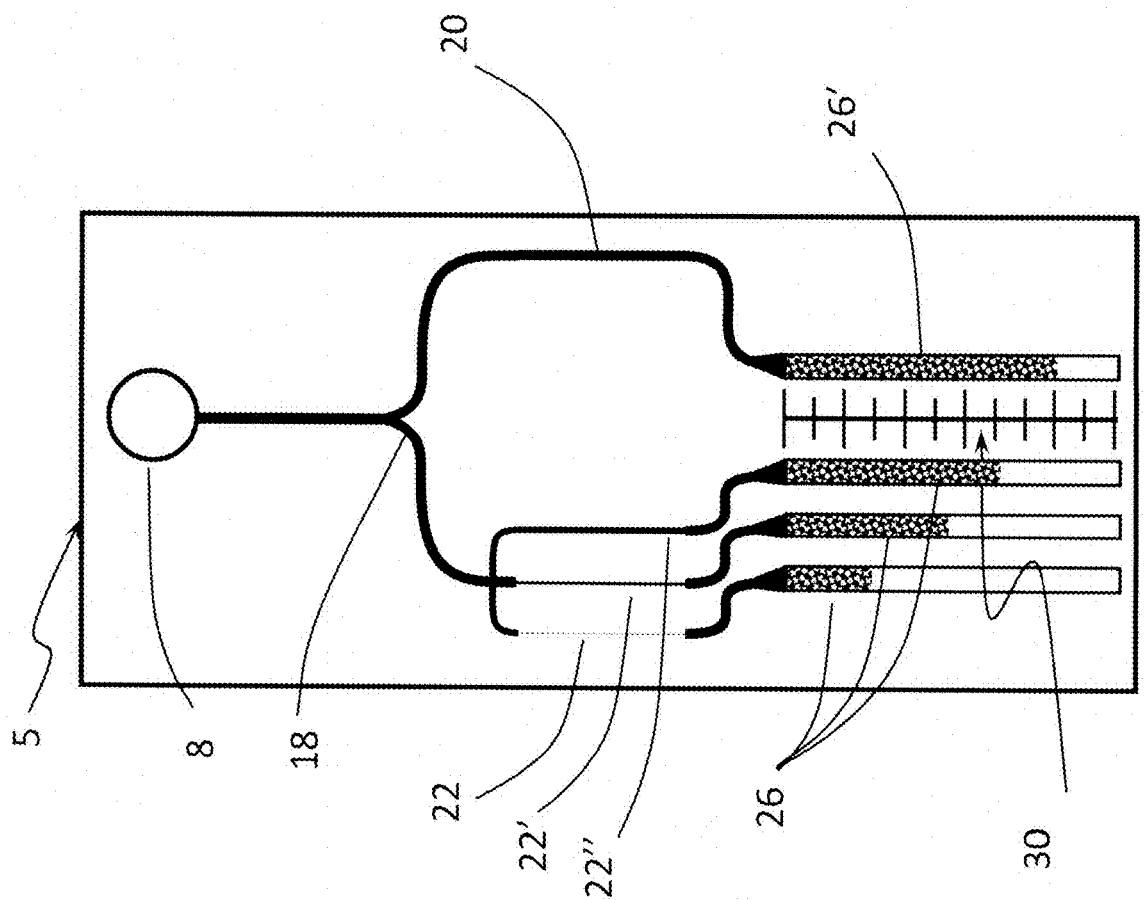
FIG. 4 is a schematic illustration of the microfluidic pScreen™ magnetic-responsive micro-bead concentration counter device, having three test micro-channels and one calibration micro-channel, according to the embodiments of the invention.

FIG. 4 shows an alternate embodiment of the microfluidic device 5 of the invention. In this embodiment, the test micro-channel (Cm) is split into three test micro-channels 22, 22', 22" which run parallel to one other. The three test micro-channels 22, 22' and 22" are of the same length but have a different inner diameter from one another. Each test micro-channel 22, 22', 22" is connected to a separate graduated column 26. In an embodiment, the first test micro-channel 22 has an inner diameter of about 50 µm to about 500 µm, the second test micro-channel 22' has an inner diameter of about 100 µm to about 250 µm, and the third test micro-channel 22" has an inner diameter of about 250 µm to about 5 mm. In another embodiment, the first test micro-channel 22 has an inner diameter of about 50 µm, the second test micro-channel 22' has an inner diameter of about 100 µm, and the third test micro-channel 22" has an inner diameter of about 250 µm. The inner diameter of the calibration micro-channel 20 is such that the area of the cross-section of the calibration micro-channel 20 is identical to the sum of the areas of the cross-sections of the three test micro-channels 22, 22', 22".

For a given amount of magnetic-responsive micro-beads entering each of the three test micro-channels 22, 22' 22", the third, largest test micro-channel 22" experiences the lowest reduction in flow rate, the second, middle-sized test micro-channel 22' experiences a reduction in flow rate greater than in the third, largest test micro-channel 22", and the first, smallest test micro-channel 22 experiences the greatest reduction in flow rate. In addition, the first, smallest test micro-channel 22 will tend to clog before the second, middle-sized test micro-channel 22' and the third, largest test micro-channel 22", and the middle-sized test micro-channel 22' will tend to clog before the largest test micro-channel 22". Hence, the device in accordance with this embodiment allows measurement of a wide range of concentrations of magnetic-responsive micro-beads, in which the first, smallest test micro-channel 22 allows for finely-tuned measurements of magnetic-responsive micro-beads at low concentrations and the third, largest test micro-channel 22" allows for gross measurements of magnetic-responsive micro-beads at high concentrations.

Figure 5:
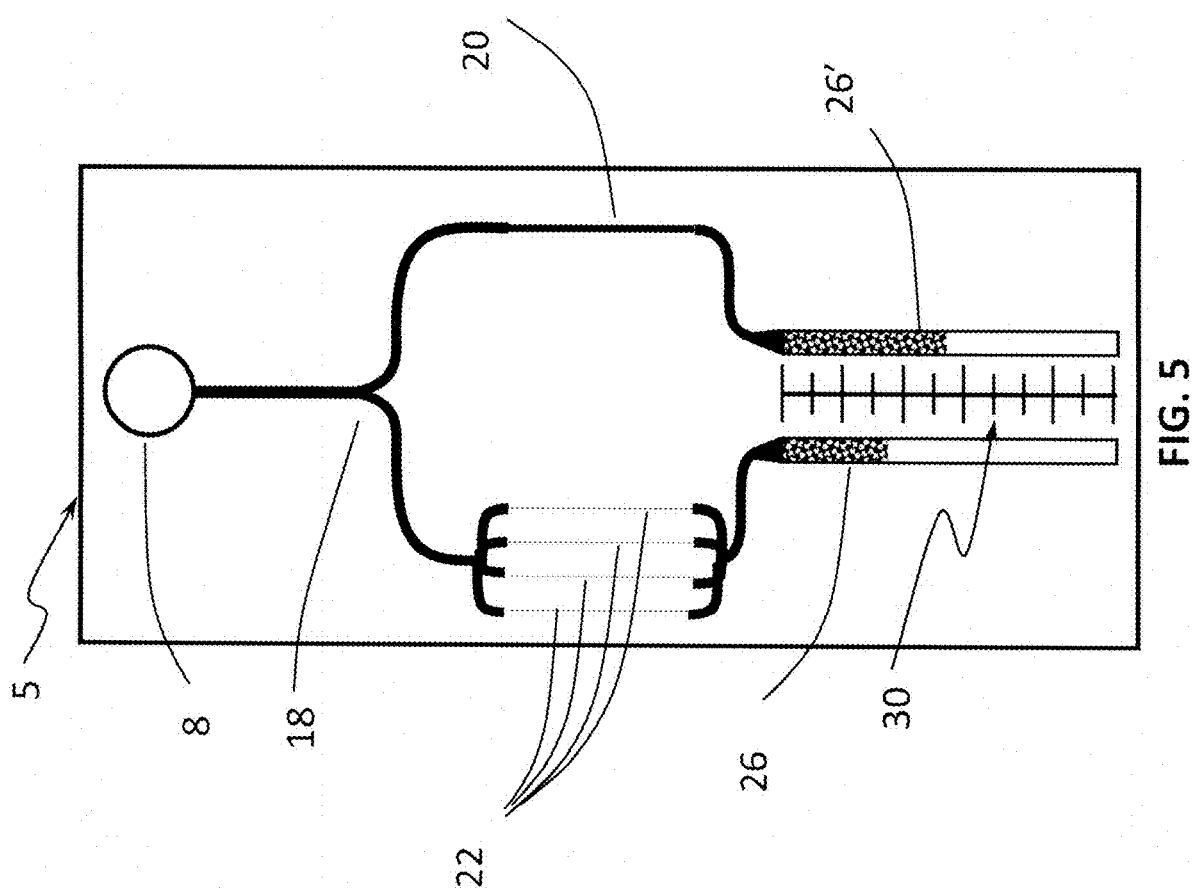
FIG. 5 is a schematic illustration of the microfluidic pScreen™ magnetic-responsive micro-bead concentration counter device, having four test micro-channels and one calibration micro-channel, according to the embodiments of the invention.

FIG. 5 shows an additional alternate embodiment of the invention. In this embodiment, the test micro-channel 22 (Cm) is split into four micro-channels which run parallel to each other. The four test micro-channels 22 have the same length and inner diameter. In an embodiment, each of the four test micro-channels has an inner diameter of about 12.5 µm to about 125 µm. In another embodiment, each of the four test micro-channels has an inner diameter of about 12.5 µm. The inner diameter of the calibration micro-channel 20 is such that the area of the cross-section of the calibration micro-channel 20 is identical to the sum of the areas of the cross-sections of the four test micro-channels 22, 22', 22".

The four test micro-channels 22 rejoin to connect to one graduated column 26. If no magnetic-responsive micro-beads flow into the four test-micro-channels 22 and the one calibration micro-channel 20, then the flow rate of the fluid through the calibration micro-channel 20 is the sum of the flow rates in each of the test micro-channels. Equations (1) through (8) also apply in this embodiment, however, because there are four parallel test micro-channels compared to one test micro-channel, a greater volume of fluid can flow through the device in a shorter amount of time, thus allowing a user to obtain a read out of results of the pScreen™ microfluidic device in a shorter period of time.

The present invention also provides a flow rate-based method for detecting and quantifying concentration of an analyte in a liquid sample. The analyte can include, without limitation, proteins, protein fragments, antigens, antibodies, antibody fragments, peptides, RNA, RNA fragments, cells, cancer cells, viruses, and other pathogenic agents.

The method according to this embodiment comprises adding a liquid sample to a liquid sample inlet of a reaction chamber. The reaction chamber has adsorbed on its surface a plurality of immobilized antigen-specific antibodies (Ab1) specific to an analyte. The surface of the reaction chamber also has a plurality of magnetic-responsive micro-beads desiccated thereon, in which each of the plurality of magnetic-responsive micro-beads is coated with an antigen-specific antibody (Ab2) specific to the analyte. The method comprises having the liquid sample incubate inside the reaction chamber, which causes rehydration of the plurality of antibody-coated magnetic-responsive micro-beads as the liquid sample is added and agitated in the reaction chamber, which rehydration disperses the antibody-coated magnetic-responsive micro-beads in the liquid sample, binding the rehydrated antibody-coated magnetic-responsive micro-beads as well as the antigen-specific antibodies immobilized on the surface of the reaction chamber to any analyte present in the liquid sample to form Ab1-analyte-Ab2-coated magnetic micro-bead complexes on the surface of the reaction chamber, having the liquid sample containing any unbound antibody-coated magnetic-responsive micro-beads exit the reaction chamber through a chamber outlet and transfer through a continuous fluid connection to a micro-channel splitter which bifurcates to form a calibration micro-channel (Co) and at least one test micro-channel (Cm). The at least one test micro-channel and the calibration micro-channel are kept at an equal and constant pressure. The calibration micro-channel is in continuous fluid connection with a graduated column, and the at least one test micro-channel is in continuous fluid connection with at least one graduated column. Each of the graduated columns has a graduated scale thereon. The method comprises measuring flow rate (Qm) of the liquid sample in the at least one test micro-channel exposed to a magnetic field gradient with flow rate (Qo) of the fluid in the calibration micro-channel not exposed to a magnetic field gradient, in which the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel, and calculating the ratio Qm/Qo, the difference Qo−Qm, and the ratio $(Qo-Qm)^p/(Qm)^q$, wherein p and q are derived through a calibration process, and wherein the ratios Qm/Qo and $(Qo-Qm)^p/(Qm)^q$ are a proxy for the number of magnetic-responsive micro-beads in the liquid sample, which is a proxy for the concentration of analyte in the liquid sample.

Figure 6:
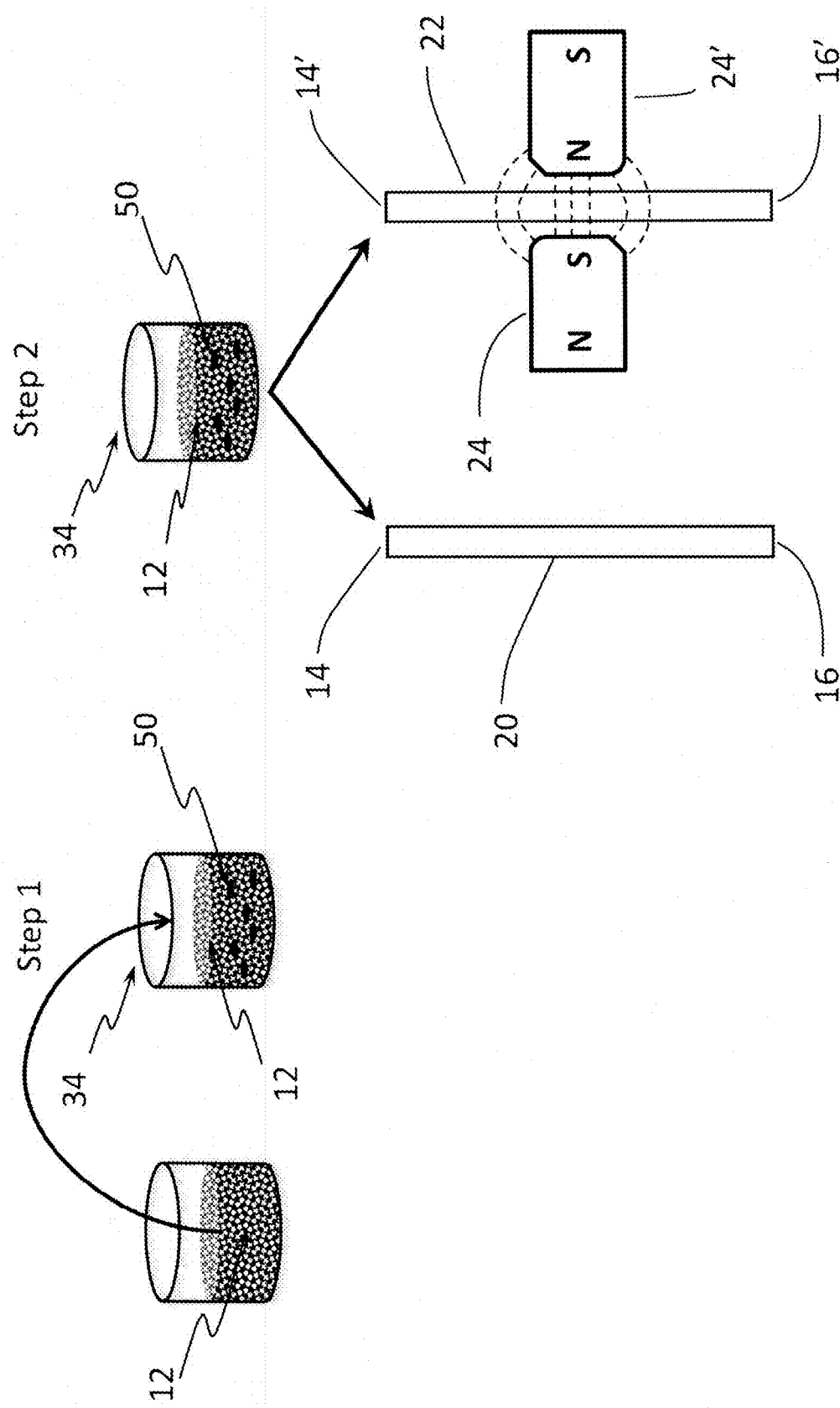
FIG. 6 is the schematic illustration of the method for determining the concentration of analyte in a fluid, in which the sample analyte is bound to immobilized analyte-specific immobilized antibodies and to analyte-specific coated magnetic-responsive micro-beads, the ratio $Q_m/Q_o$, of the flow rate $Q_o$ in the calibration micro-channel, Co, and the flow rate, $Q_m$, in the test micro-channel, Cm, is measured, according to the embodiments of the invention.

As shown in FIG. 6, a liquid sample 12 is added, Step 1, to a reaction chamber 34, which has adsorbed on its surface a plurality of immobilized antigen-specific antibodies (Ab1) (not shown) and contains a plurality of magnetic-responsive micro-beads coated with antigen-specific antibodies (Ab2) 50 desiccated on the surface of the reaction chamber 34. In Step 1, by adding the liquid sample to the reaction chamber 34, the antibody-coated magnetic-responsive micro-beads 50 are rehydrated and they, as well as the antigen-specific antibodies immobilized on the surface of the reaction chamber 34, bind to any analyte present in the liquid sample 12 to form Ab1-analyte-Ab2-coated magnetic-responsive micro-bead complexes (not shown) on the surface of the reaction chamber 34, with any unbound magnetic-responsive micro-beads 50 free to flow (Step 2) into two micro-channel inlets 14, 14' and out of two micro-channel outlets 16, 16'. The test micro-channel 22 on the right is exposed to a high-gradient magnetic field generated by two magnets 24. As described in the previous paragraph, the number of magnetic-responsive micro-beads in a liquid sample passing through two micro-channels, a test micro-channel (Co) and a calibration, or control micro-channel (Cm), is proportional to the ratio, Qm/Qo, between the flow rate (Qm) in a micro-channel (Cm) exposed to a localized high-gradient magnetic field, and the unperturbed flow rate (Qo) in a micro-channel (Co) not exposed to the localized high-gradient magnetic field. Therefore, by measuring the flow rates Qm and Qo, the concentration of analyte in the liquid sample can be determined. The method applies to a wide range of antigen concentration, from about 0.01 ng/ml to about 1.0 µg/ml.

The present invention further provides a pScreen™ microfluidic immunoassay device for the detection and quantification of proteins, protein fragments, antigens, antibodies, antibody fragments, RNA, RNA fragments, cells, cancer cells, viruses, and other pathogenic agents. This device leverages the previously described method for detecting and quantifying concentration of an analyte in a liquid sample.

Principle of Operation

Figure 7:
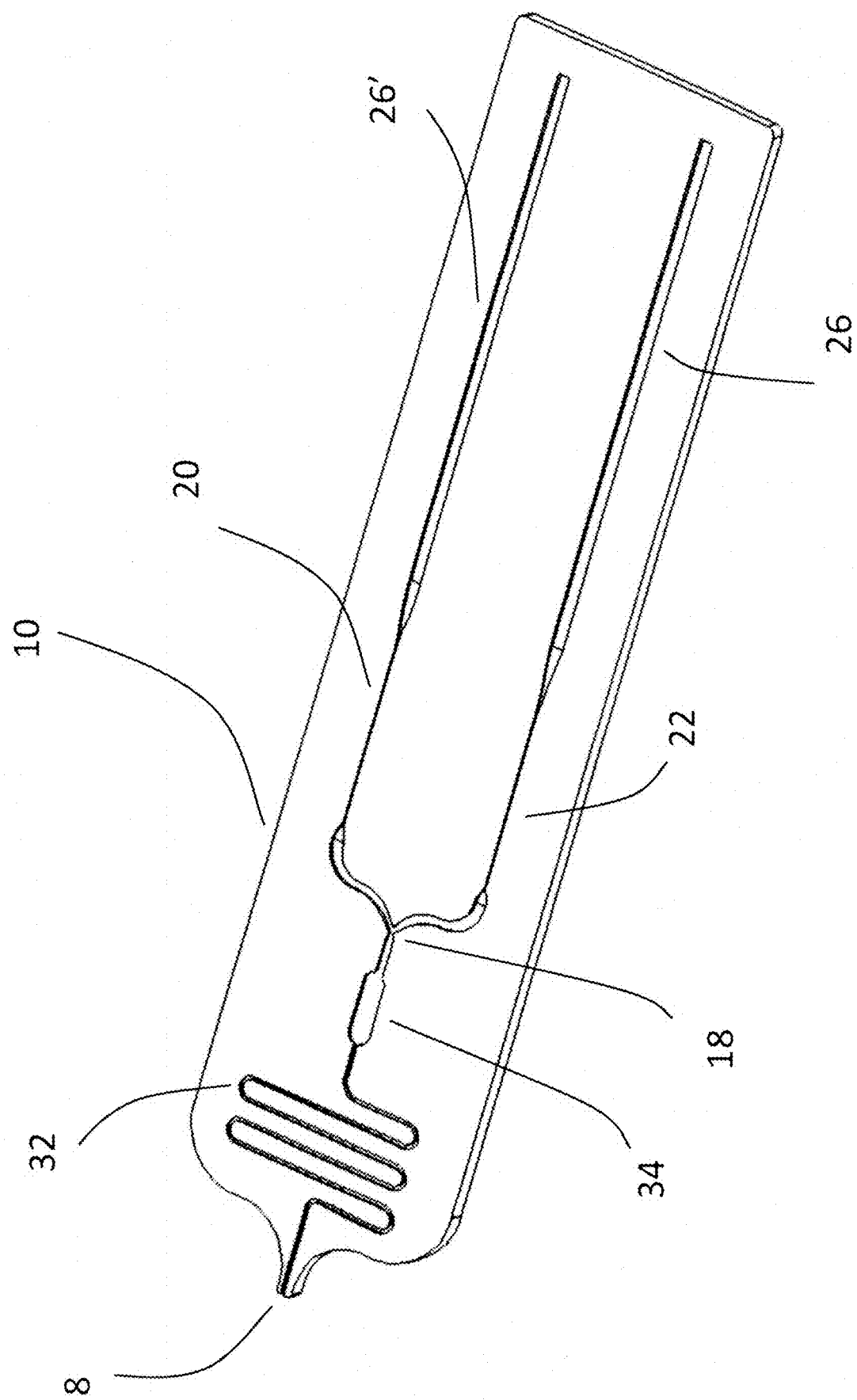
FIG. 7 is a schematic illustration of the pScreen™ immunoassay device, according to the embodiments of the invention.

In one embodiment of the invention, as shown in FIG. 7, the pScreen™ microfluidic immunoassay device 10 has a liquid sample inlet 8, a flow resistor channel 32, a reaction chamber 34, a micro-channel splitter 18, a test micro-channel 22, a calibration micro-channel 20 and graduated readout columns 26, 26'. In use, a liquid sample, or specimen, which may contain an unknown amount of a target analyte, is applied into the liquid sample inlet 8. By capillary action, the sample is self-propelled and transferred from the liquid sample inlet 8 into the reaction chamber 34 via the flow resistor channel 32. The flow rate of the liquid sample is determined by the cross-section and length of the flow resistor channel 32 and the surface tension of the device material and sample liquid, as well as by the binding kinetic reaction between the analyte, i.e., antigen, and antibody in the reaction chamber 34.

Figure 8A:
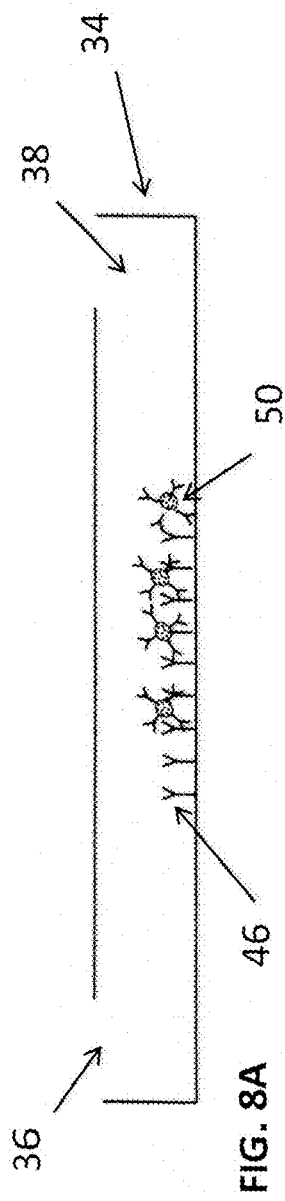
Figure 8B:
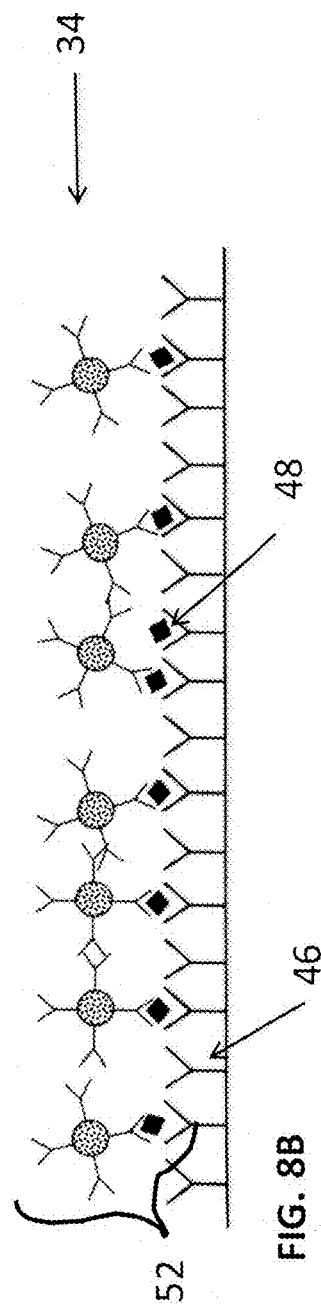
Figure 8C:
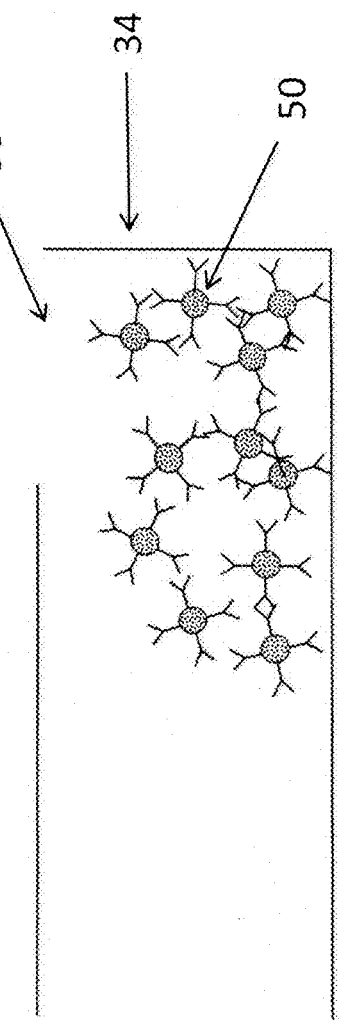
Figure 9:
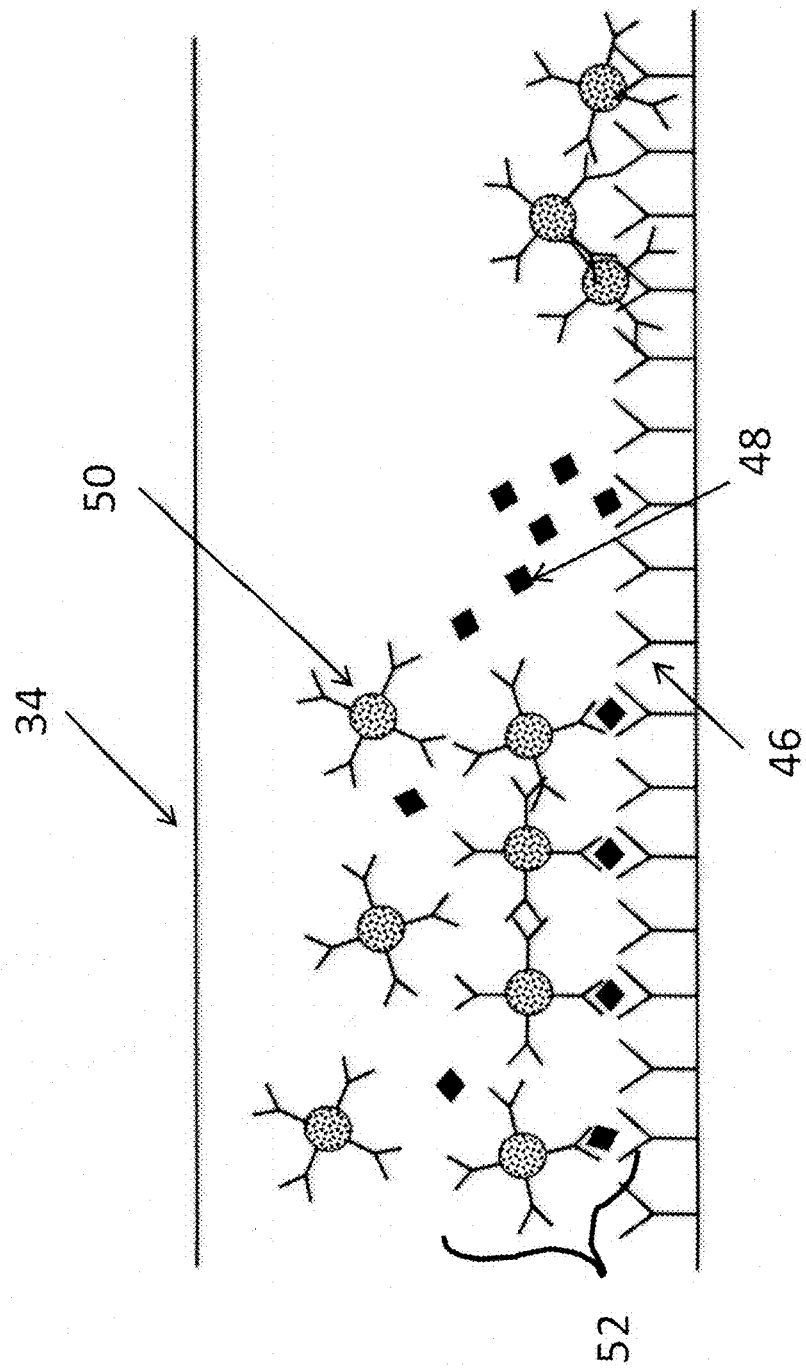
FIG. 9 is a schematic illustration which shows the formation of the Ab1-antigen-Ab2-magnetic-responsive micro-bead complexes as the sample with the antigen flows through the reaction chamber and rehydrates the magnetic-responsive micro-beads, according to the embodiments of the invention.

As shown in FIG. 8A, the reaction chamber 34 is coated with antigen-specific antibodies (Ab1) 46 immobilized onto the surface of the reaction chamber 34. The antigen-specific antibodies (Ab1) 46, referred to as capturing antibodies, may be primary or secondary antibodies. The antigen-specific antibodies (Ab1) 46 are bound to the surface of the reaction chamber 34 via adsorption. The surface of the reaction chamber 34 also is coated with antibody-coated magnetic-responsive micro-beads 50 by desiccation. The magnetic-responsive micro-beads may be desiccated on the same region of the device where Ab1 antibodies 46 are bound, or in a region preceding where the Ab1 antibodies 46 are bound. The antibody-coated magnetic-responsive micro-beads 50 are coated with antigen-specific antibodies (Ab2). These antigen-specific antibodies (Ab2) may be primary or secondary antibodies. As the liquid sample flows into the reaction chamber 34 via a chamber inlet 36, the antigen-specific antibody-coated magnetic-responsive micro-beads 50 are rehydrated and dispersed in the liquid, and any antigen molecules 48 contained in the sample bind to the antigen-specific antibodies (Ab1) 46 immobilized on the surface of the reaction chamber, and to the antigen-specific antibodies (Ab2) coating the magnetic micro-beads, forming Ab1-antigen-Ab2-coated magnetic-responsive micro-bead complexes 52 (FIG. 8B). The formation of Ab1-antigen-Ab2-coated magnetic-responsive micro-bead complexes 52 anchors the bound antibody-coated magnetic-responsive micro-beads 50 onto the surface of the reaction chamber 34. After all antigen molecules 48 have reacted to form the Ab1-antigen-Ab2-coated magnetic-responsive micro-bead complexes 52, any unbound, i.e., free, antibody-coated magnetic-responsive micro-beads 50 exit the reaction chamber 34 via a chamber outlet 38 (FIG. 8C), leaving behind the bound antibody-coated magnetic-responsive micro-beads 50 in the reaction chamber 34. FIG. 9 shows the formation of the Ab1-antigen-Ab2-coated magnetic-responsive micro-bead complex 52 as a liquid sample containing an antigen 48 flows through the reaction chamber 34 and rehydrates the antibody-coated magnetic-responsive micro-beads 50.

A negative liquid sample, i.e., a sample not containing detectable traces of the targeted analyte, results in zero antibody-coated magnetic-responsive micro-beads anchored to the reaction chamber's surface, as the Ab1-antigen-Ab2-coated magnetic-responsive micro-bead complexes cannot form. An analyte (i.e., antigen)-positive sample, on the other hand, results in antibody-coated magnetic-responsive micro-beads anchored to the reaction chamber's surface via the Ab1-antigen-Ab2-coated magnetic micro-bead complexes. Thus, the higher the concentration of analyte in the liquid sample, the greater the number of magnetic-responsive micro-beads anchored to the reaction chamber's surface, and hence the fewer the number of free magnetic-responsive micro-beads reaching the reaction chamber assay outlet. In the extreme case of very high analyte concentration, all antibody-coated magnetic-responsive micro-beads will be anchored to the reaction chamber's surface, and none will exit through the reaction chamber's assay outlet.

After flowing through the reaction chamber, the liquid sample, self-propelled by capillary action, reaches the pScreen™ magnetic micro-bead concentration counter portion of the device (which principle of operation has been described previously). If the liquid sample flowing into the test micro-channel and the calibration micro-channel contains no magnetic-responsive micro-beads, the flow rate in both the test and calibration micro-channels will be identical, and thus the sample volume collected in each of the graduated columns will be identical. The user easily is able to observe that the volume of sample in each of the graduated columns is of equal length. On the other hand, if the sample coming from the micro-channel splitter contains magnetic-responsive micro-beads in any concentration other than zero, the flow of the liquid in the test micro-channel will be retarded (due to the magnetically-induced flocculation of the magnetic micro-beads). Hence, the length of the volume of liquid in the test graduated column will be less than the length of the volume of liquid in the calibration graduated column by an amount proportional to the magnetic-responsive micro-bead concentration in the volume of liquid flowing into the graduated columns. In other words, the higher the magnetic-responsive micro-bead concentration in the liquid reaching the test and calibration micro-channels, the greater the difference in the lengths of the volume of liquid observed in the two graduated columns. The resulting difference between the volumes of liquid collected in the two graduated columns is easily visible to the naked eye.

In an embodiment of the pScreen™ microfluidic immunoassay device, described in detail above and shown in FIG. 4, the test micro-channel (Cm) is split into three test micro-channels 22, 22' and 22" which run parallel to each other. In another embodiment of the pScreen™ microfluidic immunoassay device, described in detail above and shown in FIG. 5, the test micro-channel (Cm) is split into four micro-channels 22 which run parallel to each other.

Figure 10:
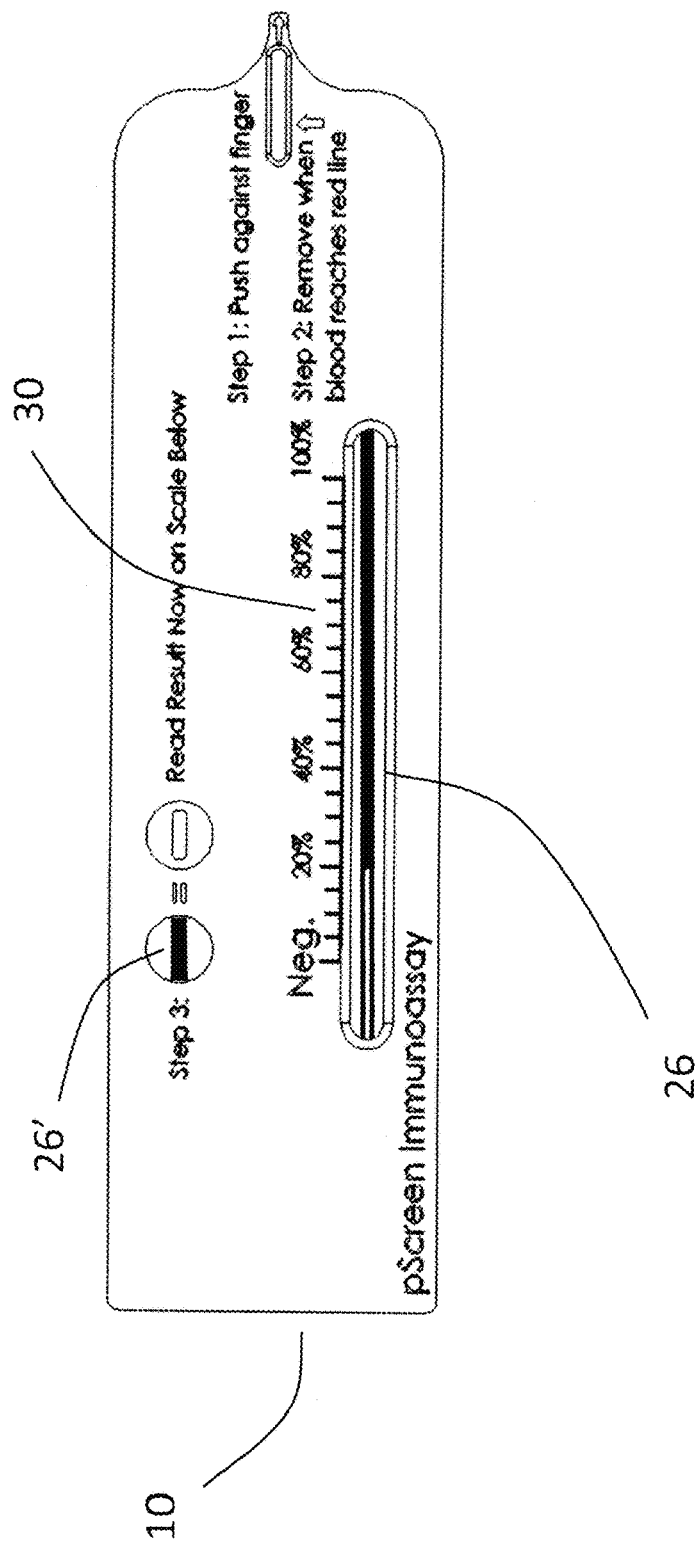
FIG. 10 is an artistic rendering of the pScreen™ immunoassay device, according to the embodiments of the invention.

FIG. 10 shows the pScreen™ microfluidic immunoassay device 10, according to the embodiments of the invention, in which the calibration column is only partially visible. In this embodiment, the read-out is taken when the portion of the calibration column that is visible changes color, i.e., fills up with liquid.

In another embodiment of the present invention, there is provided a method for detecting and quantifying concentration of an analyte in a liquid sample using the pScreen™ immunoassay device having a plurality of reaction chambers and a system of micro-channels. The method comprises adding a liquid sample to a liquid sample inlet which is in continuous fluid connection with a reaction chamber inlet manifold micro-channel, which is in continuous fluid connection with a plurality of reaction chambers. Each of the reaction chambers has adsorbed on its surface a plurality of immobilized antigen-specific antibodies (Ab1) specific to an analyte. The surface of each of the reaction chambers also has a plurality of magnetic-responsive micro-beads desiccated thereon, in which each of the plurality of magnetic-responsive micro-beads is coated with an antigen-specific antibody (Ab2) specific to the analyte. The method further comprises having the liquid sample incubate within the plurality of reaction chambers, which causes rehydration of the plurality of antibody-coated magnetic-responsive micro-beads as the liquid sample is added and flows in each of the reaction chambers, which rehydration disperses the antibody-coated magnetic-responsive micro-beads in the liquid sample, binding the rehydrated antibody-coated magnetic-responsive micro-beads as well as the antigen-specific antibodies immobilized on the surface of each of the reaction chambers to any analyte present in the liquid sample to form Ab1-analyte-Ab2-coated magnetic-responsive micro-bead complexes on the surface of each of the reaction chambers, and having the liquid sample containing any unbound antibody-coated magnetic-responsive micro-beads exit the plurality of reaction chambers through each of the reaction chamber's outlet manifold micro-channels. Each of the outlet manifold micro-channels is comprised of a micro-channel that is in continuous fluid connection with a connector micro-channel, which is in continuous fluid connection with a terminal flow splitter micro-channel. The terminal flow splitter micro-channel bifurcates to form a calibration micro-channel (Co) and at least one test micro-channel (Cm). Each of the outlet manifolds is connected to the connector micro-channel via a passive valve. Each of the passive valves function to substantially stop, for a given period of time, the flow of fluid from moving forward into the micro-channel splitter, hence allowing time for any antigen, capture antibodies and magnetic-responsive micro-beads to chemically react in the plurality of reaction chambers. The period of time for which each of the passive valves substantially stops the fluid from moving forward is determined by a desired incubation time, which incubation time provides an optimum reaction time for the specific antibody-antigen of the assay.

The method further comprises measuring the volume, Vm, of the liquid sample passing through the at least one test micro-channel exposed to a magnetic field gradient, in which the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel, and the volume of the liquid sample passing through the calibration micro-channel, Vo, not exposed to a magnetic field gradient, calculating the difference Vo−Vm, or the ratio $(Vo-Vm)^p/(Vm)^q$, wherein p and q are derived through a calibration process, wherein the ratios Vm/Vo and $(Vo-Vm)^p/(Vm)^q$ are a proxy for the number of magnetic-responsive micro-beads in the liquid sample exiting the reaction chambers, which is a proxy for the concentration of analyte in the liquid sample, and then quantifying the concentration of analyte in the liquid sample.

In another embodiment of the present invention, there is provided a single use, portable, lab-on-card microfluidic pScreen™ immunoassay device having a plurality of reaction chambers and a system of micro-channels for detecting and measuring an analyte in a liquid sample.

Figure 16A:
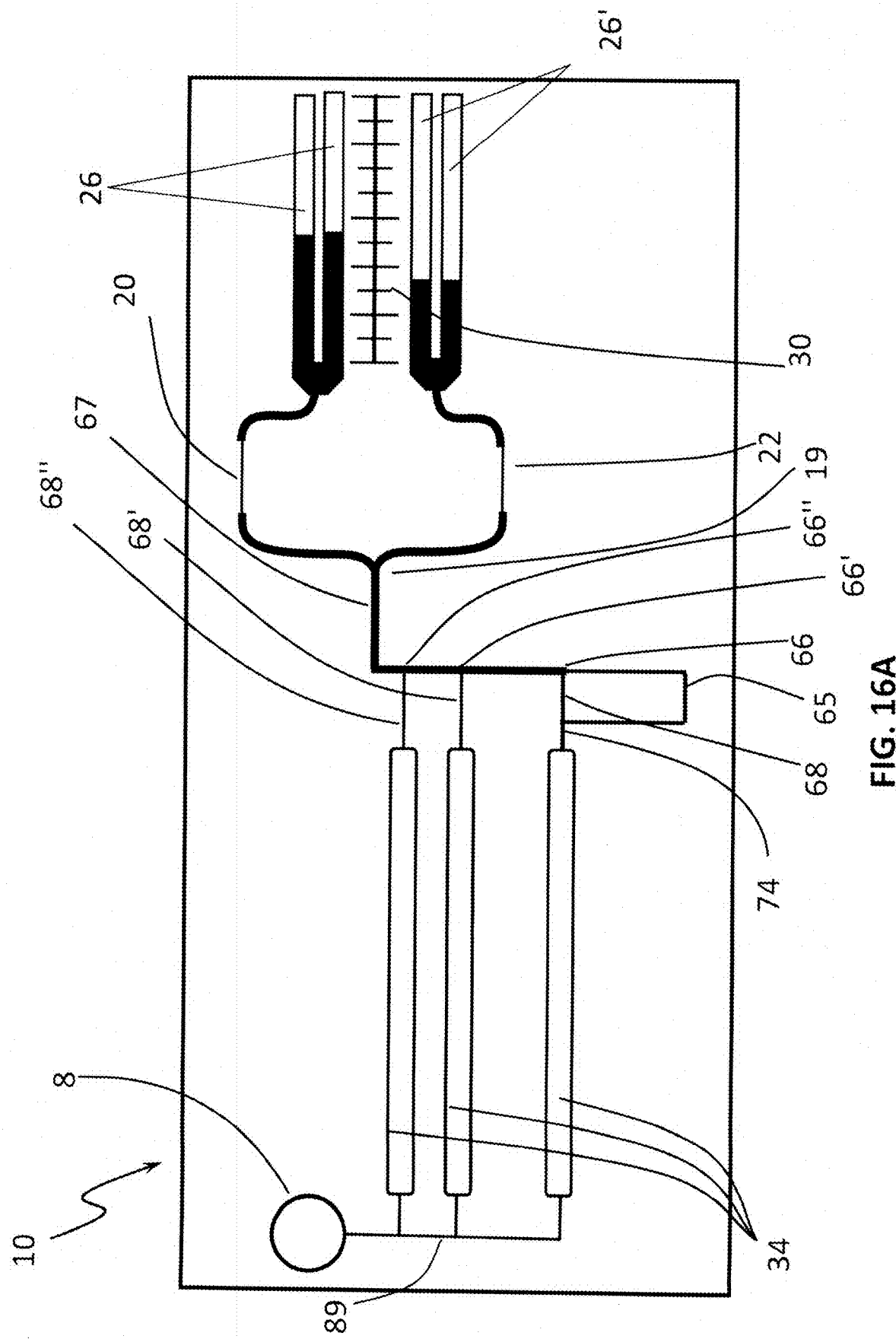
FIGS. 16A and 16B are schematic illustrations of the pScreen™ immunoassay device, FIG. 16A showing a top view, and FIG. 16B showing a side view, in accordance with the invention.
Figure 16B:
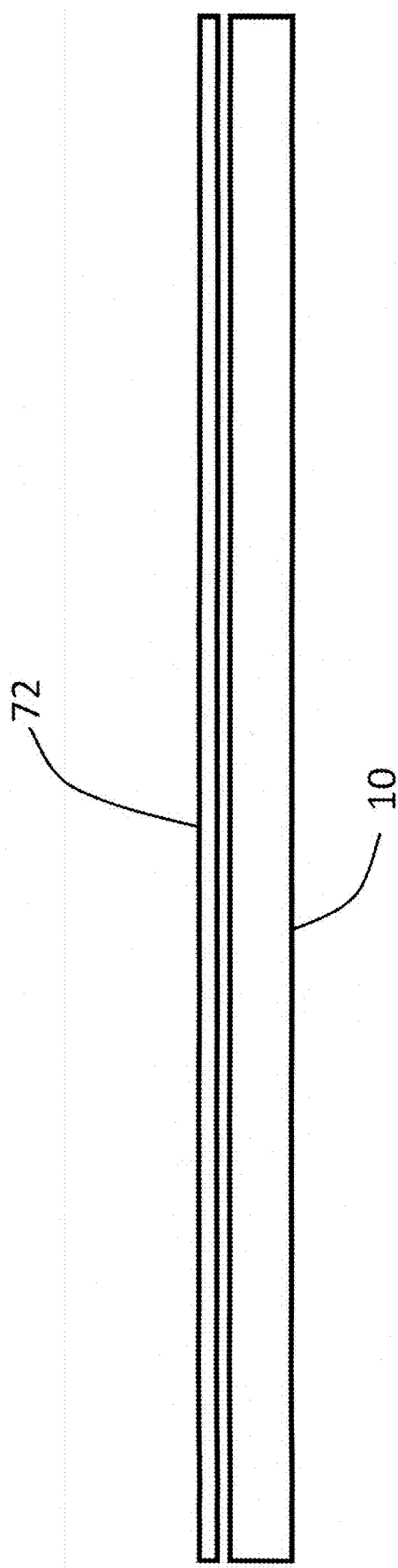

In particular, as shown in FIG. 16A (top view) and 16B (side view), the microfluidic pScreen™ immunoassay device 10 comprises the microfluidic device 10 with a sealing layer 72 atop the microfluidic device (shown in FIG. 16B). As shown in FIG. 16A, a liquid sample inlet 8 is provided for accepting a liquid sample. The liquid sample inlet 8 is in continuous fluid connection with a reaction chamber inlet manifold micro-channel 89 which is in continuous fluid connection with a plurality of reaction chambers 34. Each of the reaction chambers 34 has adsorbed on its surface a plurality of immobilized antigen-specific antibodies (Ab1) specific to an analyte, as well as having a plurality of magnetic-responsive micro-beads desiccated thereon. In an embodiment, each of the plurality of reaction chambers 34 may be coated with a different Ab1 antibody as well as having different Ab1 surface densities in order to react with a plurality of antigens. Each of the plurality of magnetic-responsive micro-beads is coated with an antigen-specific antibody (Ab2) specific to the analyte.

In an embodiment, magnetic-responsive micro-beads may be coated with different Ab2 antibodies in order to react with a plurality of antigens. Flow of the liquid sample through each of the plurality of reaction chambers 34 rehydrates the plurality of antibody-coated magnetic-responsive micro-beads, which disperses into the liquid sample. The analyte present in the liquid sample binds to the dispersed antibody-coated magnetic-responsive micro-beads as well as to the antigen-specific antibodies immobilized on the surface of each of the plurality of reaction chambers 34 to form Ab1-analyte-Ab2-coated magnetic-responsive micro-bead complexes. Any unbound antibody-coated magnetic-responsive micro-beads, dispersed in the fluid, exit the reaction chambers 34 through outlet manifold micro-channels 68, 68' 68", flow through a connector micro-channel 67, and then flow through a terminal flow splitter micro-channel splitter 19 that bifurcates to form a calibration micro-channel (Co) 20 and at least one test micro-channel (Cm) 22. The calibration micro-channel 20 and the at least one test micro-channel 22 each are kept at an equal and constant pressure.

Figure 17B:
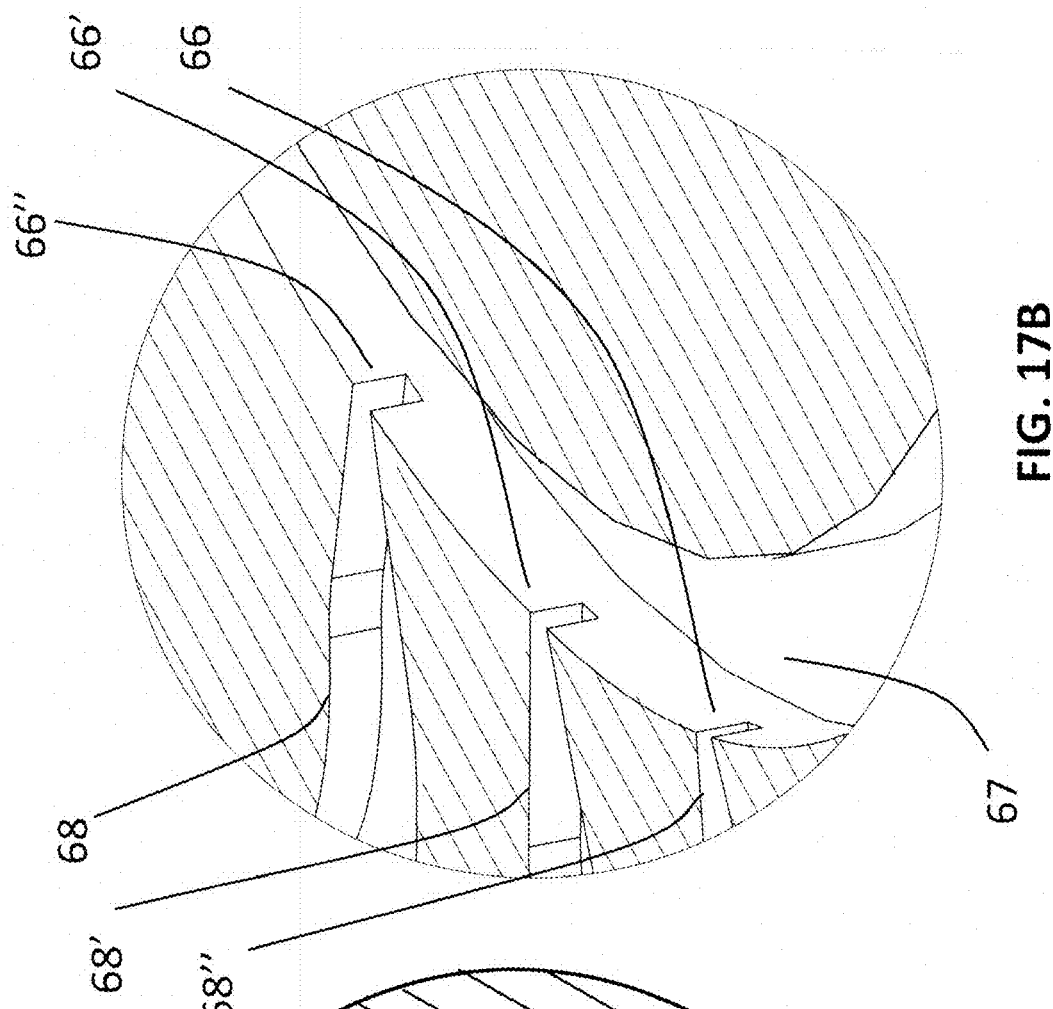
FIGS. 17A and 17B and 17C are schematic illustrations of the system of passive valves, with FIGS. 17A and 17B showing a top view, and FIG. 17C showing a perspective view of the intersection of one outlet manifold micro-channel with the connector micro-channel, in accordance with the invention.
Figure 17A:
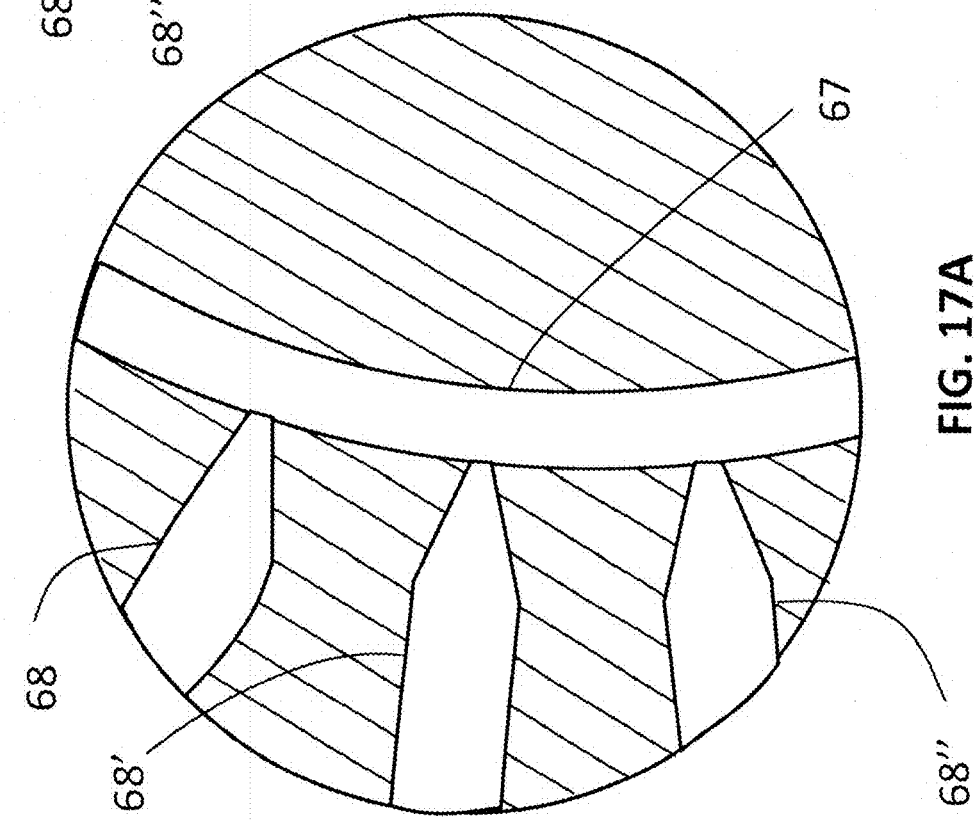

Each of the plurality of the reaction chamber's 34 outlet manifold micro-channels 68, 68', 68" is in continuous fluid connection with the connector micro-channel 67 via a passive valve 66, 66', 66". As used herein, the term "passive valve" is meant to describe a valve that does not have any moving mechanical parts. The passive valves 66, 66', 66" are formed by having sharp edges at the intersections of the plurality of outlet manifold micro-channels 68, 68', and 68" with the connector micro-channel 67, as shown in FIGS. 17A and 17B (top views) and 17C (perspective view). Fluid flow substantially stops to a negligible flow rate at each intersection of a passive valve 66, 66', 66" with the connector micro-channel 67. The fluid resumes flowing into the connector micro-channel 67 only when the valves 66, 66', 66" burst sequentially, each within a few seconds from one other. The term "burst" is a well-known term in the field of microfluidics, and is described in detail below. The period of time that the fluid is substantially stopped at the passive valves 66, 66', 66" is referred to as "the delay time," because the valves delay the time it takes for the fluid to move from the outlet manifold micro-channels 68, 68', 68" into the connector micro-channel 67.

Figure 17C:
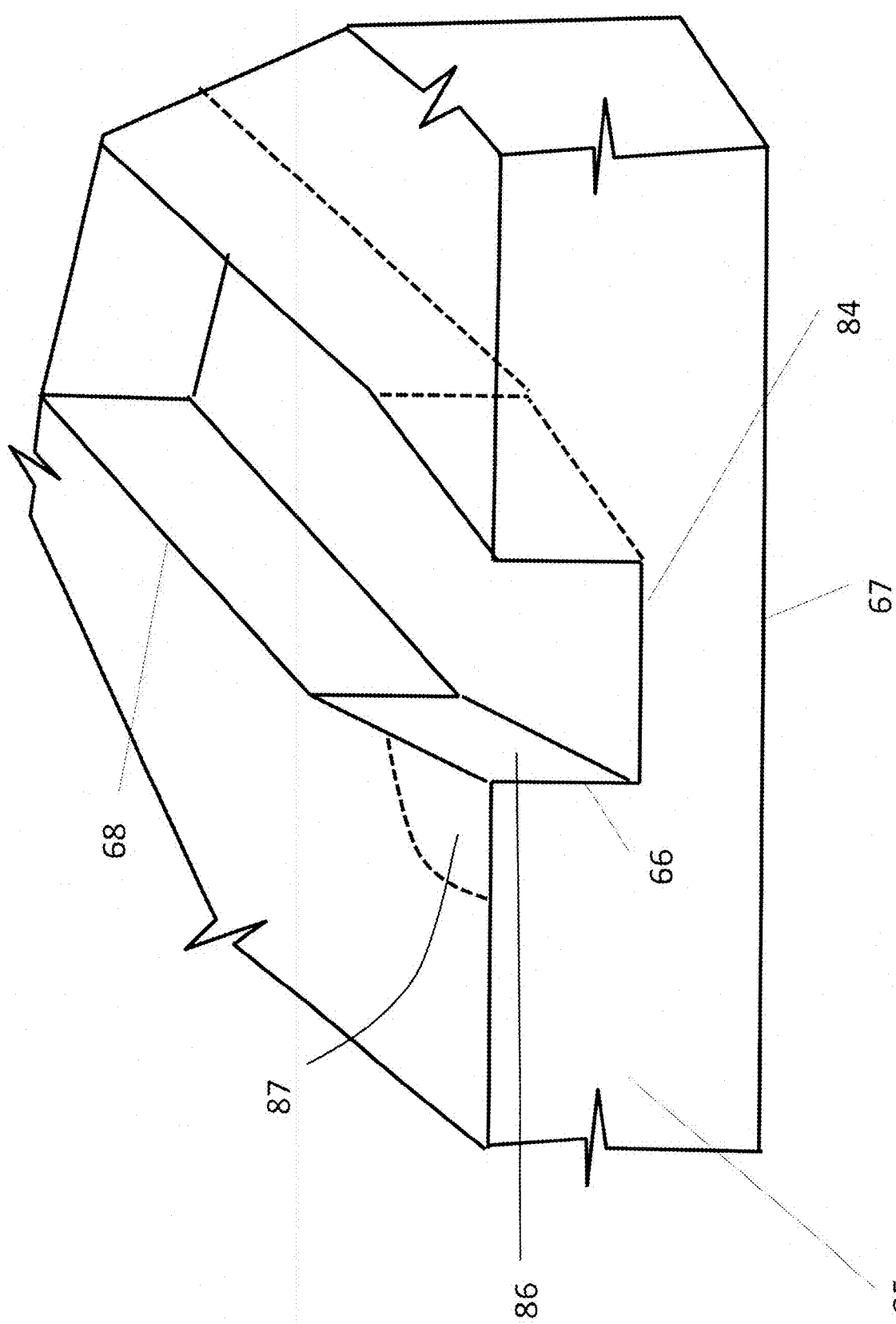

FIG. 17C shows the spatial relationship of one outlet manifold micro-channel 68, a passive valve 66 located at the end of the outlet manifold micro-channel 68, and the connector micro-channel 67. The bottom surface 84 of the outlet manifold micro-channel 68 forms a 90-degree angle with the side wall 85 of the connector micro-channel 67. The side wall 86 of the outlet manifold micro-channel 68 forms a 90-degree or greater angle 87 with the side wall 85 of the connector micro-channel 67. These 90-degree or greater angles have the effect of increasing the contact angles of the fluid against the walls of the micro-channels, above 90 degrees, which creates a convex meniscus, which, as per the Young-Laplace principle, creates a pressure gradient in the direction opposite to the fluid direction of motion. This, in turn, stops the flow of fluid from proceeding forward through the intersection of the outlet manifold micro-channel and the connector micro-channel, hence creating a passive valve to the fluid forward motion. Once the flow is stopped, it requires an applied pressure gradient, in the direction of the fluid motion, which is greater than the pressure gradient created by the passive valves, to get the fluid to resume flowing past the valve and into the connector micro-channel 67. This process would normally require a mechanical action to apply the pressure gradient in the direction of the flow, either automatically by using an electrical or mechanical timer system, or by an operator-activated system.

In this embodiment, a primary flow splitter 74 (shown in FIG. 16) is placed before valve 66 joins the connector micro-channel 67. The primary flow splitter forms a secondary micro-channel, referred to as a delay micro-channel 65, which connects to the connector micro-channel 67 and is located before valve 66 intersects with the connector micro-channel 67 along the flow direction. As used herein, the area where the valves 66, 66', 66" intersects with the connector micro-channel is referred to as "the valve-connector intersection".

As described above, fluid flow is stopped where the valve 66 intersects with the connector micro-channel 67, whereas the fluid in the delay micro-channel 65 continues to flow via capillary action. Fluid from the delay micro-channel 65 therefore is free to enter the connector micro-channel 67, as the delay micro-channel 65 forms a continuous surface with the connector micro-channel's 67 wall. This is in contrast to the intersection between the micro-channel outlet manifold 68 and the connector micro-channel 67, which forms the passive valve 66 due to their sharp edges. As used herein, a sharp edge is defined as the angle formed between the tangents of two surfaces, at the surfaces' intersection area or line, which angle is greater than zero. As fluid enters the connector micro-channel 67, the fluid wets the walls of the connector micro-channel 67 and continues to flow by capillary action. As fluid reaches the first valve 66 in its path, it joins the fluid effectively stopped at the intersection of the valve 66 and the connector micro-channel 67, providing a continuous surface for the fluid to move past the valve 66. At this point, the valve 66 is said to burst, since the fluid is now flowing through the valve propelled by capillary action of the fluid meniscus that travels through the connector micro-channel 67.

The period of time that it takes for the fluid to travel through the delay micro-channel 65 is referred to herein as the delay time. During the delay time, the flow in each of the plurality of reaction chambers 34, except for the reaction chamber connected to the delay micro-channel, is stopped, whereas the flow in the reaction chamber connected to the delay micro-channel can be reduced to an arbitrary low level, or substantially stopped, i.e., the flow rate is decreased to a negligible rate, as described in detail below. This delay time allows time for the magnetic-responsive micro-beads to bind more effectively to the captured antigen. The delay time is chosen to match a desired incubation time value, which value is determined as providing the optimum reaction time for the specific antibody-antigen of the assay. As used herein, the optimum reaction time is defined as the shortest time that results in between about 60% to 90% of the total number of antigen molecules in the fluid contained in the plurality of reaction chambers to bind to the capture antibodies.

As shown in FIG. 16A, the calibration micro-channel 20 is in continuous fluid connection with one or more parallel calibration graduated columns 26, and the at least one test micro-channel 22 is in continuous fluid connection with one or more parallel test graduated columns 26'. The at least one test micro-channel 22 is exposed to a magnetic field gradient, which causes flocculation of the magnetic-responsive micro-beads in the at least one test micro-channel 22. The flocculation reduces the flow rate (Qm) of the liquid sample in the at least one test micro-channel 22 compared to the flow rate (Qo) of the liquid sample in the calibration micro-channel 20. Each of the one or more test graduated columns 26' has a graduated scale 30 thereon which provides a read-out of the sample volume collected in each of the test graduated columns 26', Vm, and the calibration graduated columns 26, Vo. The difference Vo−Vm, or the ratio $(Vo-Vm)^p/(Vm)^q$, wherein p and q are derived through a calibration process, are a proxy for the number of magnetic-responsive micro-beads in the liquid sample, which is a proxy for the concentration of analyte in the liquid sample, which allows for the quantification of the concentration of analyte in the liquid sample.

In an embodiment, the reaction chambers 34 are about 20 mm to 50 mm long, about 1 mm to 5 mm wide, and about 50 μm to 200 μm deep. The inlet manifold micro-channel 89 is about 50 μm to 300 μm deep and wide, and about 10 mm to 40 mm long. The outlet manifold micro-channels 68, 68', and 68" are about 50 μm to 200 μm wide, and about 50 μm to 300 μm deep. The connector micro-channel 67 is about 50 μm to 400 μm wide, and about 60 μm to 400 μm deep. The delay micro-channel 65 about 30 mm to 120 mm long, about 50 μm to 300 μm wide, and about 50 μm to 300 μm deep.

The delay time can range between about 30 seconds and 10 minutes. In an embodiment, the delay time ranges between about 1 minute and 4 minutes.

In an embodiment, the number of reaction chambers is between 1 and 8. In another embodiment, the number of reaction chambers is 4.

Figure 18:
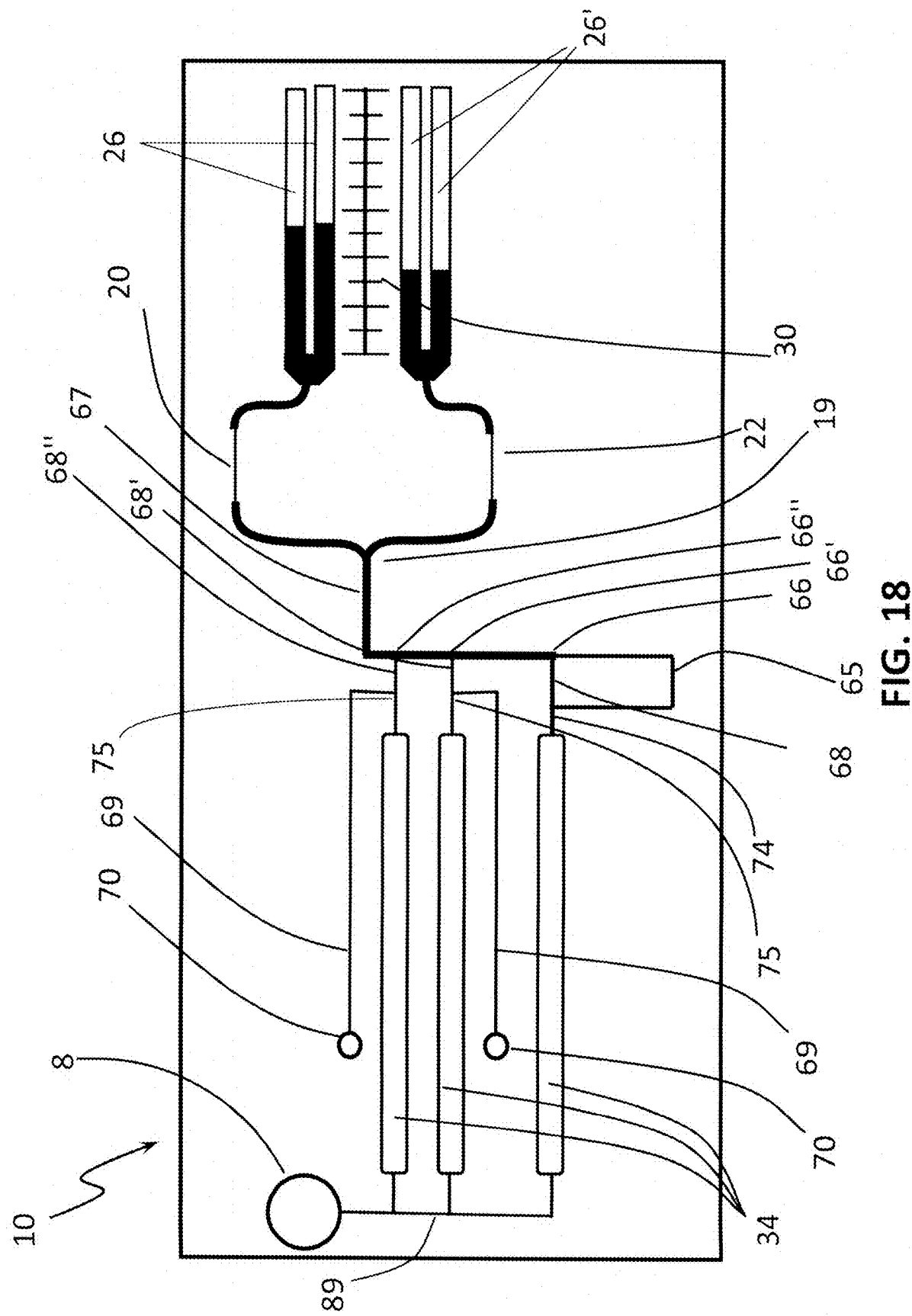
FIG. 18 is a schematic illustration of the pScreen™ immunoassay device, in accordance with the invention.

In another embodiment, as shown in FIG. 18, each of the reaction chambers 34, except for the reaction chamber 34 having the primary flow splitter 74 and the delay micro-channel 65, are in continuous fluid connection with secondary flow splitter micro-channels 75, which are in continuous fluid connection with the outlet manifold micro-channels 68', 68". Each secondary flow splitter 75 is in continuous fluid connection with an appendix micro-channel 69, which terminates in a vent port 70 that is open to atmospheric pressure. The number of appendix micro-channels therefore is equal to the number of reaction chambers minus one. The appendix micro-channels 69 are about 50 μm to 400 μm wide, about 50 μm to 400 μm deep, and about 30 mm to 120 mm long.

Whereas fluid flow stops where the outlet manifold micro-channels 68, 68', 68" intersect the connector micro-channel 67, fluid flow is continuous in the appendix micro-channels 69. The advantage of introducing the appendix micro-channel in the present invention is evident when a hydrophilic sealing layer is used in place of a hydrophobic sealing layer, which sealing layer is described in detail below.

The passive valves have three sharp edges and one continuous surface, which is a sealing layer. FIG. 19 shows the sealing layer 72, which can be made of either a hydrophilic or hydrophobic material. The advantage of a hydrophilic sealing layer is that it provides, in addition to the three walls of the micro-channels which are carved in the microfluidic device, a fourth continuous surface which promotes fluid flow movement by capillary action throughout the device, thus increasing the overall flow rate and reducing the assay time. In contrast, a hydrophobic layer resists the flow, thus reducing the capillary action of the three walls of the micro-channels carved in the microfluidic device 10. The term "carved" is used herein to refer to any of the methods used to make the microfluidic device of the present invention, as described below. Using a hydrophilic material may, however, result in failure of the passive valves to stop the fluid flow through the valves. This is because a sealing layer made of a hydrophilic material, by providing a hydrophilic continuous surface, allows the fluid to flow easily past the passive valves, thus causing the valves to fail, i.e., the fluid is not stopped at the valves. This is in contrast to a hydrophobic sealing layer, which impedes the forward flow of fluid, and thus acts as a flow stop in addition to the three walls of the micro-channels. Unimpeded flow occurs anytime the hydrophilic sealing layer produces a capillary pressure larger than the pressure gradient created by the sharp edges of the passive valves which opposes the flow through the valves. Thus, with a highly hydrophilic surface layer this unimpeded flow will very likely occur. However, incorporating the appendix micro-channels 69 (shown in FIG. 18) in the present invention, a hydrophilic sealing layer can be used without causing failure of the valves 66, 66', 66". This is because when fluid is flowing in the appendix micro-channels 69, the pressure gradient across the valves 66, 66', 66" is reduced by the fluid flow capillary action in each of the appendix micro-channels, which creates a pressure gradient in the opposite direction that is larger than the pressure gradient created by the capillary action through the valves, hence stopping the flow of the fluid from flowing through the passive valves.

In accordance with the invention, during the delay time, the flow in each of the plurality of reaction chambers 34 is reduced to an arbitrary low level, or is substantially stopped, i.e., the flow rate is decreased to zero or is negligible. This arbitrary low flow rate is achieved by adjusting the length, width, and depth of the delay micro-channel and the appendix micro-channels. Because both the delay micro-channel and the appendix micro-channels are relatively narrow and long micro-channels, flow resistance in these micro-channels rapidly increases, which in turn causes the flow rate (which is inversely proportional to the fluid resistance) in these micro-channels to decrease and stop. In addition, by increasing the width and depth of the last few mm of the final portions of the delay micro-channel and the appendix micro-channels (which represents only a small portion of the total length of these micro-channels), by about two to six fold, the capillary pressure in these micro-channels is greatly reduced. Thus, because the flow resistances in both the delay micro-channel and the appendix micro-channels are substantially unchanged, by increasing the width and depth of the final portion of these micro-channels, this results in a further reduction of the flow rate. Hence, by adjusting the length, width and depth of the delay micro-channel and the appendix micro-channels, the flow rate in the reaction chamber can be made arbitrarily low so that flow substantially stops.

Referring again to FIG. 19, the immunoassay device is constructed on two levels, rather than in a co-planar configuration, with the one or more reaction chambers 34 constructed on a bottom level, the system of embedded micro-channels 78 constructed on a top level, and a sealing layer 72 positioned in between the top and bottom levels. In particular, all of the micro-channels of the device are placed on one level by mold casting or any of the above-described methods. The micro-channels are formed by sealing two layers of materials, one in which the system of micro-channels are embedded 78 and the other forming the sealing layer 72. The one or more reaction chambers 34 which are formed on the lower level is constructed by bonding the bottom plate 88 of each of the reaction chambers 34 (which are coated with one or more capture antibodies) to the bottom side of the sealing layer 72 to form the one or more reaction chambers 34. The two layers, i.e., the embedded micro-channels 78 and the sealing layer 72, are connected and sealed by adhesives or other bonding materials. Bonding the one or more reaction chambers 34 with the bottom of the sealing layer 72 may be accomplished by a variety of methods, which include, without limitation, double pressure sensitive adhesive 71 or thermal bonding. Holes which form the reaction chamber inlet 36 and the reaction chamber outlet 38 (also shown in FIG. 8) are placed on the sealing layer to transfer fluid in and out of the one or more reaction chambers 34.

Referring now to FIGS. 20A and B, the liquid sample inlet 8 of the immunoassay device 10 has a conical shape (shown in cross-section in FIG. 20A). The inner surface 76 of the liquid sample inlet 8 is made super-hydrophobic by either coating the inner surface 76 with a super-hydrophobic layer or by a surface texture that creates a capillary contact angle 77 between 120 degrees and 160 degrees. The upper opening 90 of the liquid sample inlet 8 has a diameter between about 3 mm and 10 mm. The lower opening 79 of the liquid sample inlet 8 (which is continuous with the reaction chamber inlet; not shown) is between about 1 mm and 6 mm. The cone angle is designed to match the capillary contact angle. The inlet shape is designed and the surface is made hydrophobic to create a convex meniscus 82 that creates a pressure within the liquid sample that is greater than atmospheric pressure and, by virtue of the Young-Laplace's principle, creates a pressure gradient that favors the flow of the liquid sample through the microfluidic device. This further increases the liquid sample flow rate through the device by providing an additional capillary pressure gradient in the direction of the flow from the liquid sample inlet toward the system of micro-channels of the device of the present invention.

As shown in FIG. 20B (expanded view of the left side of the inlet opening), the cone angle (alpha) 80 of the conical inlet is related to the fluid contact angle (beta) 77, which is the angle formed by inlet surface tension force, 81, with the inlet hydrophobic inner surface. For a fixed value of beta, the optimum value of alpha is given by the following equation: alpha=beta−90°. When this equation is satisfied, then the capillary pressure created by the fluid meniscus is maximum, and is equal to two times the surface density divided by the radius of the inlet circumference at the location where the fluid meniscus intersects the conical inlet's inner surface. Therefore, as the fluid in the inlet is reduced as fluid moves into the device, the radius of the inlet circumference, at the location where the fluid meniscus intersects the conical inlet's inner surface, decreases, and the capillary pressure created by the meniscus increases.

In an embodiment, the walls of the micro-channels are coated with hydrophilic films to decrease the fluid contact angle and in turn increase the capillary action and thus the flow rate, hence reducing the assay time. Hydrophilic films used in coating include, but are not limited to, hyaluronic acid, bovine serum albumin, or a protein-free blocking solution. Other hydrophilic liquid or sprays also may be used.

Figure 23:
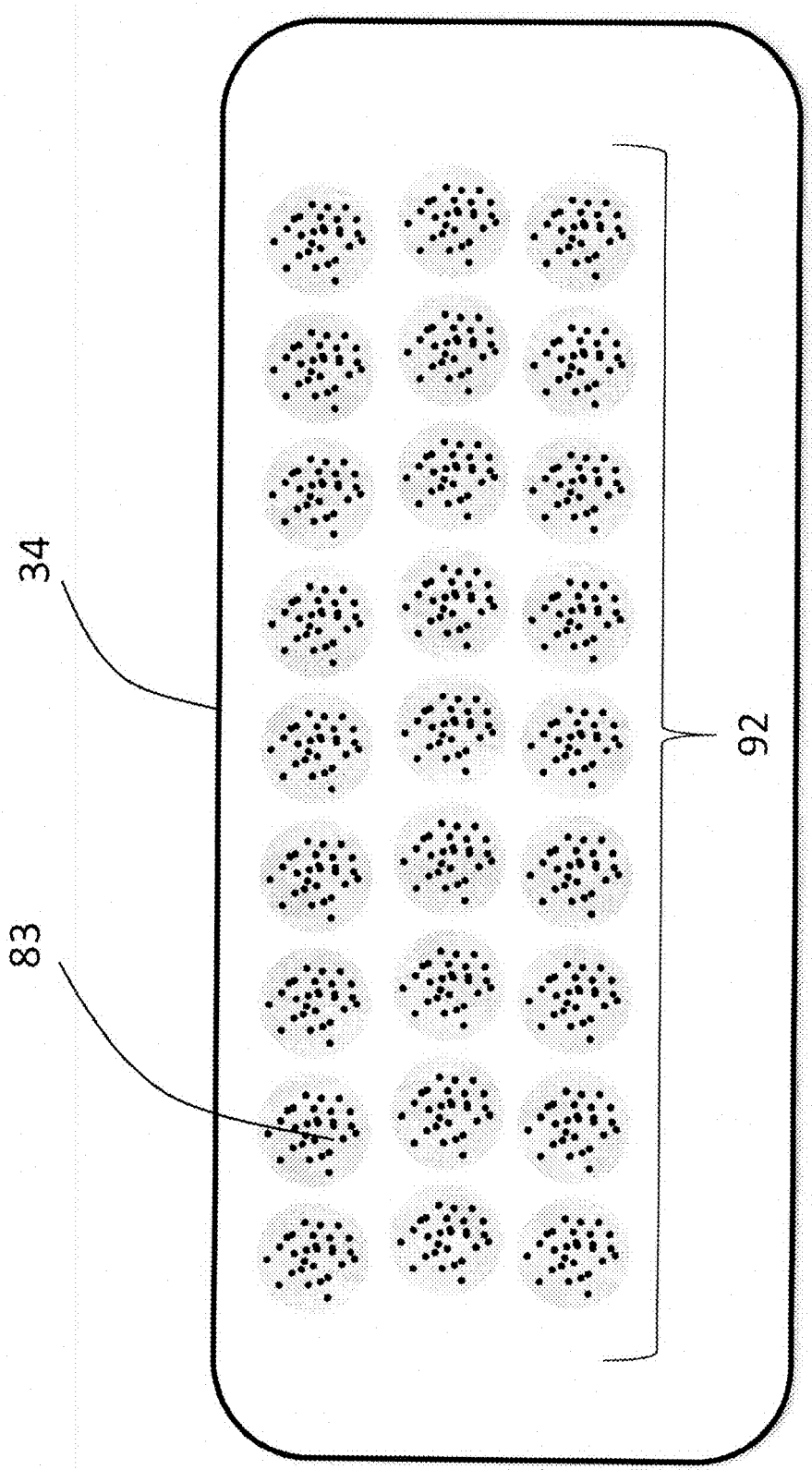
FIG. 23 is a schematic top view illustration of one reaction chamber showing an array of micro-bead drops, in accordance with the invention.

In an embodiment, the micro-beads are dispensed in the one or more reaction chambers in nanoliter-sized drops 83 (shown in FIG. 23). The nanoliter-sized drops are dispensed using methods which include, without limitation, microarray spotting pins or a nanoliter-sized pipette mechanism. Drops may be dispensed in a variety of configurations and arrays. Drop size may range from about 5 nl to greater than 100 nl. Drops may be layered directly on top of one another in one or more layers to increase the number of micro-beads in each spot and overall in the one or more reaction chambers, which promotes micro-bead release when a liquid sample rehydrates the micro-beads. A higher percentage of micro-beads releases from the surface of the one or more reaction chambers when more than one layer of drops is applied, and thus more micro-beads are rehydrated and become available for binding and for detection of analyte in the liquid sample.

In an embodiment, sucrose, glycerol, and trehalose or any combination of two or more of sucrose, glycerol and trehalose, are added to the micro-bead's buffer solution to promote micro-bead release. The micro-bead's buffer solution typically is phosphate buffered saline (PBS). When sucrose, glycerol, trehalose, or a combination thereof is added to the micro-bead buffer solution, a higher percentage of microbeads releases from the surface than when sucrose, glycerol, trehalose are not included in the solution. Therefore, when sucrose, glycerol, trehalose, or a combination thereof is added to the micro-bead buffer solution, more micro-beads are rehydrated and thus available for binding and for detection of analyte in the liquid sample. Concentration of these additives from about 5-40% of the buffer solution promotes micro-bead release.

In an embodiment, the dispensing solution density is altered depending on the density of micro-beads used. Micro-beads have a higher density than both water and PBS. Thus, the micro-beads settle to the bottom of the reservoir or tubing during dispensing and the number of micro-beads dispensed per drop changes over time. In order to keep the number of micro-beads dispensed per drop constant over time, the density of the micro-beads must be the same as the density of the solution in which the micro-beads are suspended during dispensing to achieve a neutral buoyancy micro-bead dispensing solution. Density of the solution can be altered to match the density of the micro-beads using additives that increase solution density, which include but are not limited to heavy water, glycerol, sucrose, polyethylene glycol, or a combination of two or more of these additives. Concentrations of these additives can be varied to match the density of a given micro-bead. In particular, the use of heavy water is very advantageous because it simply replaces the water in the micro-bead dispensing solution. Suspension in neutral buoyancy fluid prevents settling and maintains uniform micro-bead concentration in the dispensing buffer for the entire time it takes to dispense the drops. Dispensing can take several hours depending on the number of devices prepared. This allows for uniformity of micro-bead concentration within each reaction chamber and between reaction chambers.

In the above-described embodiments of the method and device of the present invention, a liquid sample flows via capillary action thorough the plurality of the reaction chambers and the system of micro-channels. The flow rate of the liquid sample varies with the position of the fluid meniscus in accordance with the embodiments of the invention. As the liquid sample enters each reaction chamber, the flow rate is relatively high, typically between about 0.3 μl/sec to 0.4 μl/sec, then the flow rate decreases as the fluid moves forward via capillary pressure created by the fluid meniscus. The mean flow rate in the reaction chamber is between about 0.15 μl/sec to 0.2 μl/sec. As the fluid meniscus enters the outlet manifold micro-channels, the flow rate further decreases, according to well-known microfluidic principles, which, in brief, states that the pressure gradient created by a micro-channel is inversely proportional to the size of the micro-channel. And, because the depth of each outlet manifold micro-channel is larger than the depth of each reaction chamber, the meniscus in each of the outlet manifold microchannels creates a lower pressure gradient and hence a lower flow rate. Then, as the liquid splits at the primary and secondary flow splitter micro-channels, the meniscuses of the branches connected to the passive valves stop, while the meniscus of the fluid in the delay and appendix micro-channels continue to move forward. Because both the delay micro-channel and the appendix micro-channels are narrow and long micro-channels, their flow resistance rapidly increases, which in turn causes the flow rate (which is inversely proportional to the fluid resistance) to rapidly decrease and substantially stop. Then, once the meniscus enters the connector micro-channel causing the system of passive valves to burst, the flow bypasses the appendix micro-channels and the delay micro-channel, and moves through the valves, and since both appendix micro-channels and the delay line have a higher flow resistance than each the outlet manifold micro-channels, the flow rate increases. Then, as the fluid flows through the calibration micro-channel (Co) and at least one test micro-channel (Cm), the flow rate slightly decreases since these micro-channels introduce a high flow resistance. Finally, the fluid enters the graduated columns, and since the graduated columns' width and depth are larger than the test and calibration micro-channels, the capillary pressure at the fluid meniscus is lowered and the flow rate decreases. When the fluid is in the graduated columns, the flow rate remains substantially constant, since the flow resistance of the graduated columns is much smaller than the sum of the flow resistances of all the preceding micro-channels. The initial high flow rate found in the reaction chambers favors the re-hydration of the magnetic micro-beads. The substantially stopped flow rate, when the fluid is in the appendix micro-channels and in the delay line, favors antigen incubation and formation of the micro-beads-antigen-capture antibody complex. Then, the increase in flow rate, when the fluid is in the connector micro-channel, favors the movement of the magnetic micro-beads that are not bound to the surfaces of the reaction chambers via the antigen. This step reduces the number of micro-beads that may bind non-specifically to the surfaces of the reaction chambers, and thus reduces assay background. Finally, the substantially constant flow rate encountered when the meniscus is in the graduated columns provides a uniform flux of micro-beads out of the reaction chambers and through the test and control micro-channels.

In another embodiment, there is provided a device for the quantification of DNA fragments based on flocculation of silica micro-beads. Under specific conditions, DNA fragments bind to the surface of the silica micro-beads and trigger their aggregation into bead clusters (i.e. aggregates). These clusters are held together by an electrostatic interaction between the DNA fragments and the silica micro-bead surface. Accordingly, the degree of flocculation is proportional to the amount of DNA fragments present in a sample. A higher concentration of DNA fragments will lead to more and larger aggregates, while a lower concentration of DNA fragments to smaller and fewer clusters. By mixing magnetic-responsive silica micro-beads to nonmagnetic-responsive silica micro-beads, the DNA-induced clusters will become magnetic-responsive. As such, even a small amount of magnetic-responsive silica micro-beads will lead to large magnetic-responsive bead clusters by addition of non-magnetic-responsive silica micro-beads.

To trigger and facilitate the binding of DNA fragments to the silica micro-beads and subsequent formation of bead clusters, the sample containing the DNA fragments first is mixed with a low pH buffer that promotes the binding of the DNA strands onto the silica micro-beads by electrostatic interaction. Subsequently, a chaotropic salt-based buffer containing either isopropyl or ethanol alcohol is added, which promotes the formation of the bead clusters by hydrophobic interactions. Following the mixing of the sample with the clustering-promoting solutions, an aliquot of the sample is transferred into a custom pScreen microfluidic device, shown in FIG. 25, which first promotes collisions between silica micro-beads, and hence the formation of magnetic-responsive bead clusters. Then, it splits the flow into two calibrated micro-channels, one of which is placed adjacent to a permanent rare-earth magnet. All magnetic-responsive bead clusters exiting the chamber and entering the micro-channel will aggregate in the proximity of the magnet and create a localized restriction, which retards the flow of liquid. Conversely, the flow in the other channel is unaffected by the presence of clusters. This enables visual readout of the concentration of DNA fragments in the sample by comparing the volumes of liquid accumulated into the two channels during an assay run time described above. In the absence of DNA fragments in the sample, only the magnetic-responsive silica micro-beads will aggregate in the proximity of the magnet. Therefore, by keeping the fraction of magnetic-responsive silica micro-beads low, a sample absent of DNA fragments will result in no appreciable difference in the amount of the volumes of liquid accumulated in the two channels. On the other hand, if DNA fragments are present in the sample, they will trigger the formation of large magnetic-responsive clusters, which then will create a large aggregate in the proximity of the magnet and introduce a localized restriction, which retards the flow of liquid in that column (i.e. test column).

The pScreen microfluidic device, therefore, allows for rapid, simple and inexpensive quantification of DNA concentration in a sample. The device does not require complex instrumentation and can be performed in less than three minutes. Moreover, it is compatible with complex samples including, without limitation, unpurified PCR amplification products, and thus can be expected to seamlessly integrate into various common molecular biology techniques and workflows.

Figure 25A:
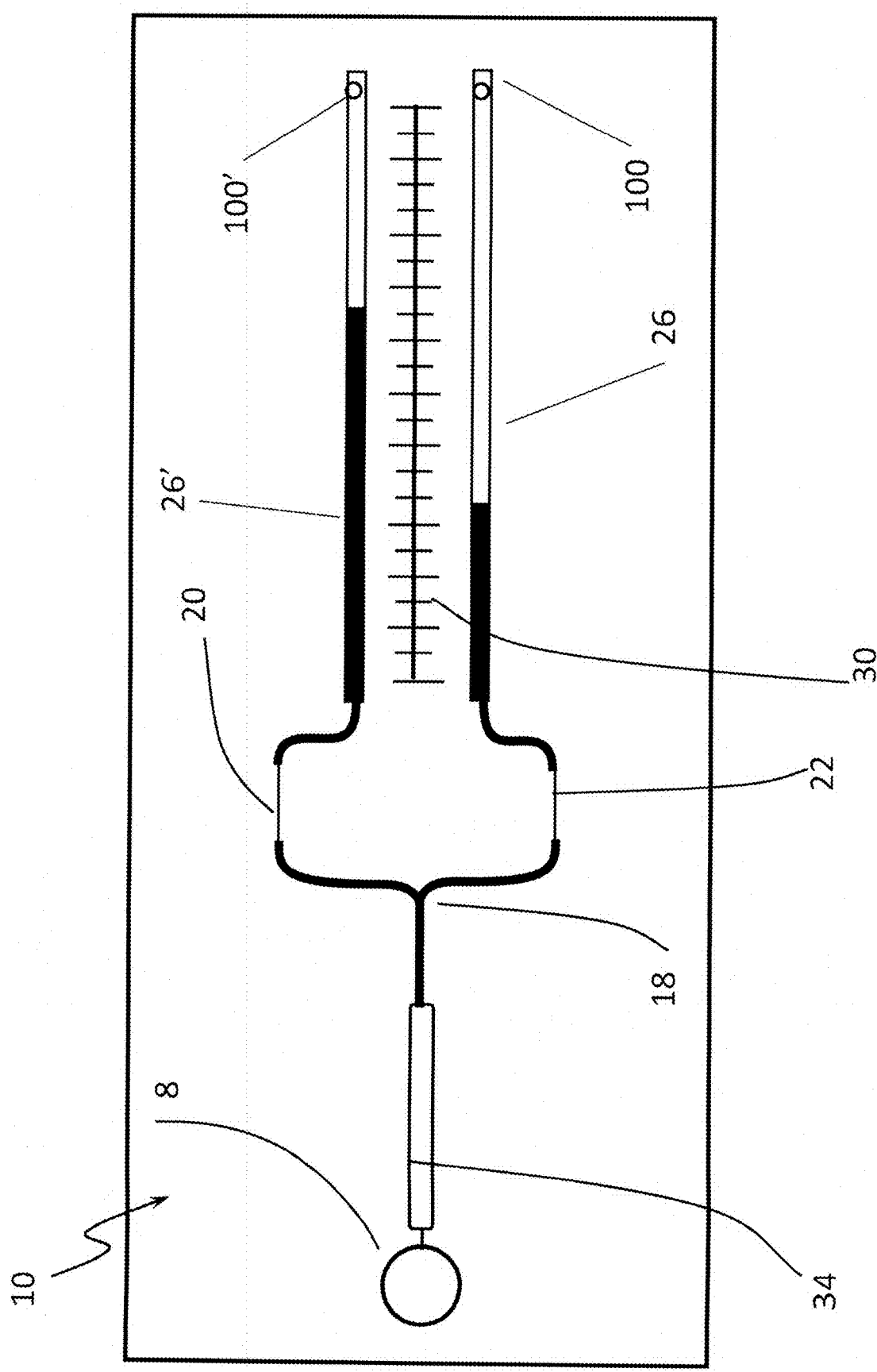
FIG. 25A is a top view schematic illustration of the pScreen™ microfluidic device for measuring DNA concentration.
Figure 25B:
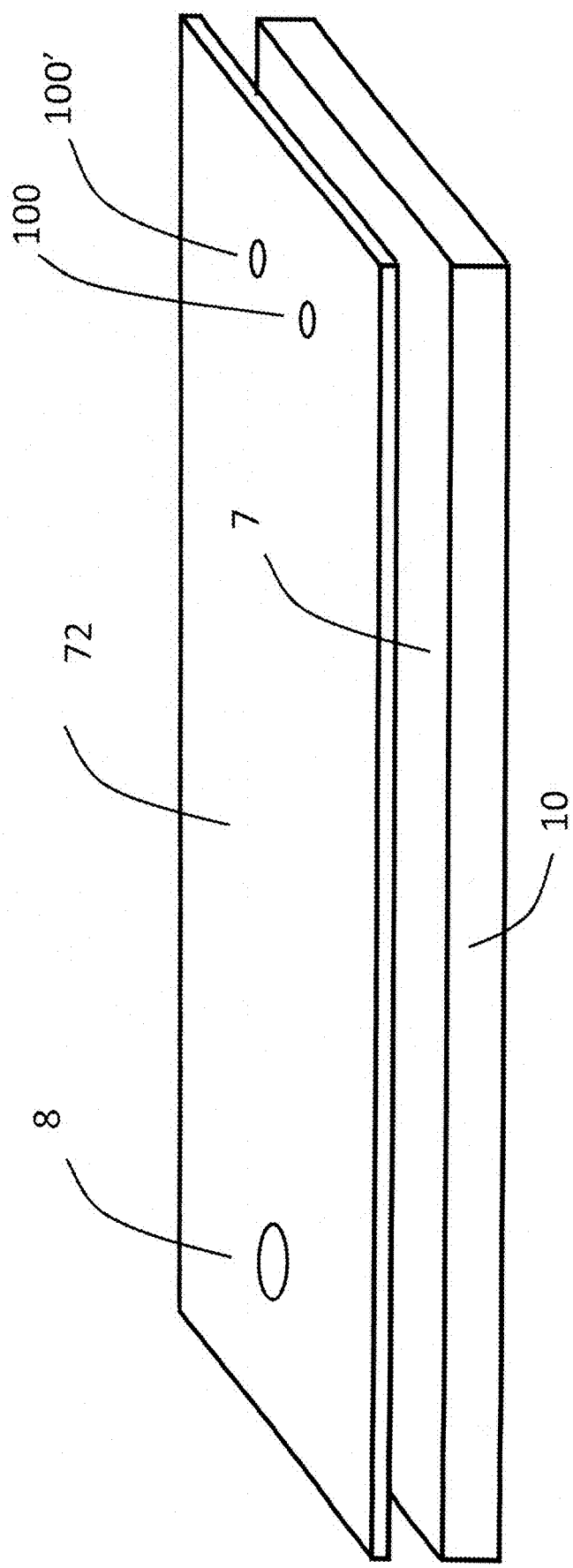
FIG. 25B is a side view schematic illustration of the pScreen™ microfluidic device for measuring DNA concentration, according to the embodiments of the invention.

In one embodiment of the device for the quantification of DNA fragments based on flocculation of silica micro-beads, there is provided a single use, portable, lab-on-card microfluidic device (shown in FIGS. 25A,B), comprising a microfluidic card 10 and a sealing layer 7 (shown in FIG. 25B) and a liquid sample inlet 8, defined by an opening for accepting the liquid sample. The microfluidic device has a reaction chamber 34 and a system of secondary micro-channels for detection and quantification of DNA fragments on flocculation of silica micro-beads in the micro-channels and the detection of magnetic aggregates in a liquid sample. As shown in FIG. 25A, the liquid sample inlet 8 is in continuous fluid connection a reaction chamber 34, which is in continuous fluid connection with a micro-channel splitter 18, which bifurcates to form a calibration micro-channel (Co) 20 and one test micro-channel (Cm) 22. The calibration micro-channel 20 is in continuous fluid connection with a control graduated column 26', and the test micro-channel 22 is in continuous fluid connection with a graduated parallel test graduated column 26'. Both columns are vented by small venting holes, 100 and 100' (shown in FIG. 25A, B), placed at the end of each column. The test micro-channel 22 is exposed to a magnetic field gradient, which causes flocculation of the magnetic-responsive clusters of the silica micro-beads in the test micro-channel 22, in the proximity of the magnet.

In use, the microfluidic device includes an assay solution comprised of two liquid buffers, Buffer 1 containing Reagent 1, and Buffer 2 containing Reagent 2. Buffer 1 contains a mixture of magnetic- and nonmagnetic-responsive silica micro-beads. First, an aliquot of the DNA sample to be tested is mixed with Buffer 1 and incubated for a period of time, T1. Then, Buffer 2 is added to the DNA sample and Buffer 1, mixed, and then incubated for a period of time, T2, to promote the formation of magnetic-responsive bead clusters. This mixture, comprised of the DNA sample, Buffer 1 and 2, then is placed on the inlet 8 of the microfluidic pScreen™ device 10. The magnetic-responsive bead clusters, dispersed in the liquid sample, flow through the reaction chamber 34 and exit through the micro-channel splitter 18 that bifurcates to form the calibration micro-channel (Co) 20 and the test micro-channel (Cm) 22. The flocculation of the magnetic-responsive clusters reduces the flow rate (Qm) of the liquid sample in the test micro-channel 22 compared to the flow rate (Qo) of the liquid sample in the calibration micro-channel 20. The test graduated column 26 has a graduated scale 30 thereon which provides a read-out of the sample volume collected in the test graduated column 26, Vm and the control graduated column 26, Vo, in which the difference, Vo−Vm, or the difference, Lo−Lm, where Lo is the length of the control column, and Lm the length of the test column, or the ratio $(Vo-Vm)p/(Vm)q$, wherein p and q are derived through a calibration process, is a proxy for the number of magnetic-responsive bead clusters in the liquid sample, which is a proxy for the concentration of DNA fragments in the liquid sample.

In an embodiment, the unknown concentration of DNA fragments in a sample is derived by comparing the difference, Lo−Lm, to the calibration curve obtained for a DNA fragment of about equal length, i.e., with an equal number of base pairs.

In an embodiment, Buffer 1 is a low pH water-based buffer containing between 1 Mole/Liter and 2 Mole/Liter of acetic acid ($CH_3COOH$), 2 Mole/Liter and 3 Mole/Liter of sodium chloride (NaCl), and between 5% v/v and 40% v/v polyethylene glycol, PEG 400; and contained silica non-magnetic-responsive micro-beads in concentrations between 10 µg/µl and 60 µg/µL, and magnetic-responsive silica beads in concentrations between 1.0 µg/µl and 6.0 µg/µl. Buffer 2 is a salt and alcohol-based buffer containing isopropyl alcohol between 10% and 50% v/v, guanidine hydrochloride between 10% and 30% w/v, and sodium perchlorate between 2% and 10% w/v. Alternatively, ethanol between 20% and 75% v/v can be used in place of isopropyl.

In an embodiment, Buffer 2 contains dyes in concentration between 0.2 and 0.5 mg/ml to make the otherwise clear liquid readily visible to the naked eye. Dyes may include Trypan Blue, Rhodamine 6G, and Crystal Violet.

In an embodiment, the non-magnetic-responsive silica micro-beads in Buffer 1 vary in size between 1 µm and 12 µm, and the magnetic-responsive micro-beads in Buffer 1 contain a magnetic kernel and are coated with a silicon dioxide ($SiO_2$) layer and vary in size between 2.5 µm and 4.5 µm.

In an embodiment, the reaction chamber 34 is 10 mm to 50 mm long, 1 mm to 5 mm wide, and 50 µm to 200 µm deep; the inlet and outlet manifolds 8 are 50 µm to 300 µm deep and wide and 10 mm to 40 mm long; the micro-channels 20 and 22 have a width between 50 µm and 200 µm, and a depth between 50 µm and 300 µm; and the columns 26 and 26' have a width between 0.5 mm and 2 mm, a depth between 50 µm and 400 µm, and a length between 100 mm and 500 mm. The sealing layer can be made of either a hydrophilic or hydrophobic material. The advantage of using a hydrophilic, rather than a hydrophobic material, is that a hydrophilic sealing layer provides, in addition to the three walls of all micro-channels embedded in 10, a fourth continuous surface that promote the flow motion by capillary action throughout the device, hence increasing the overall flow rate and reducing the assay time.

Passive valves are essential features of many microfluidic devices. They enable the—on/off switch of flow without the assistance of any external devices, battery or mechanical transducers. For example, in the embodiment shown in FIG. 25, the user is required to either measure at the same time, both Vm and Vo, or alternatively measure either Vm or Vo while measuring the total volume added into the device inlet. Furthermore, too large a sample volume may fill both columns to full capacity. As the control column reaches its end, the flow will continue in the test channel, eventually reaching the same length of the control channel, hence resulting in a test failure. On the other hand, a small sample volume will result in both Vm and Vo being shorter than optimum, resulting in a smaller difference between test and control columns, which in turn will reduce assay sensitivity. Here, we present a novel microfluidic passive valve that is able to stop the flow in a primary micro-channel as the liquid flowing in a secondary micro-channel reaches a predetermined mark.

Figure 26A:
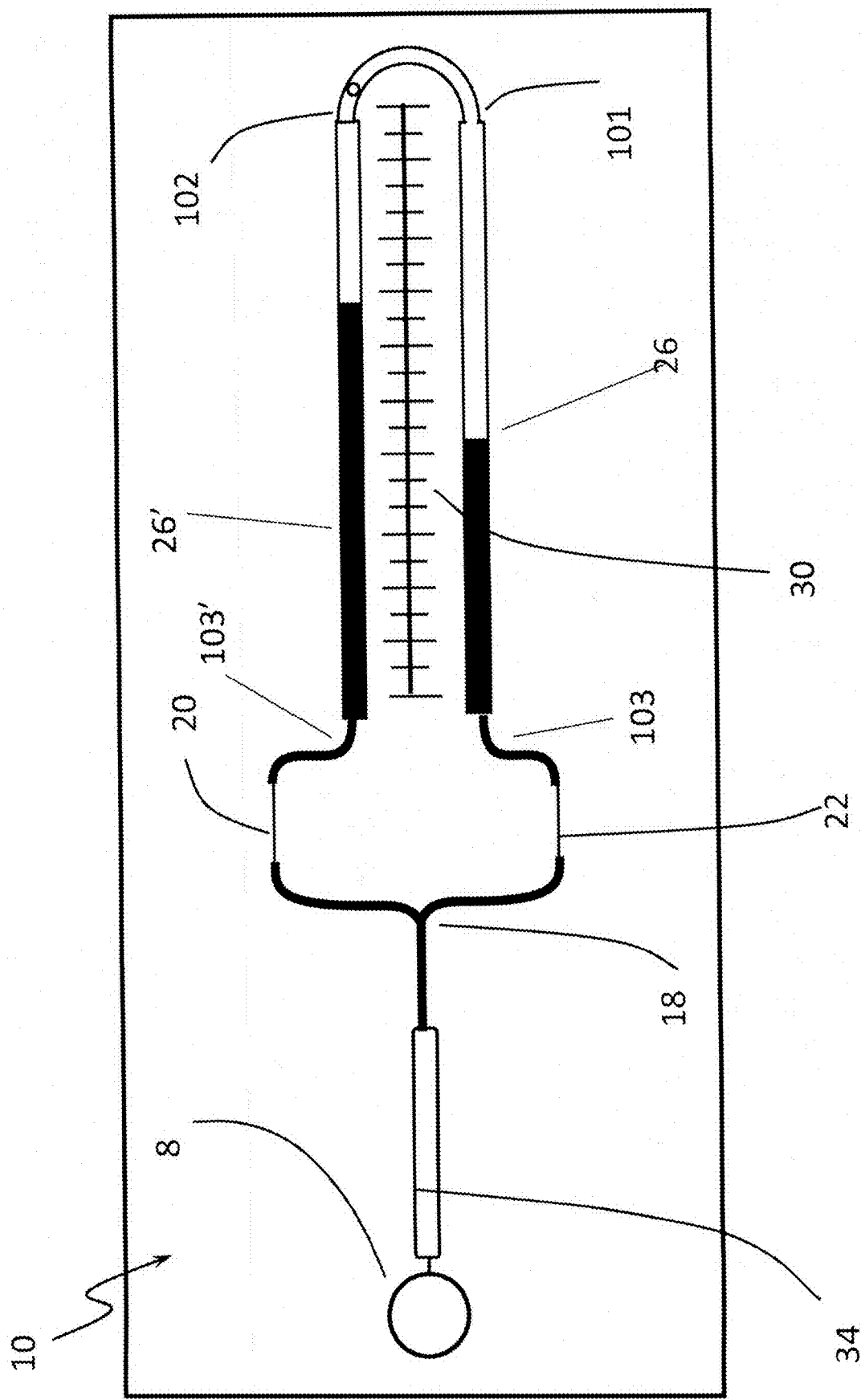
FIG. 26A is a top view schematic illustration of the pScreen™ microfluidic device for measuring DNA concentration which includes a joining channel.
Figure 26B:
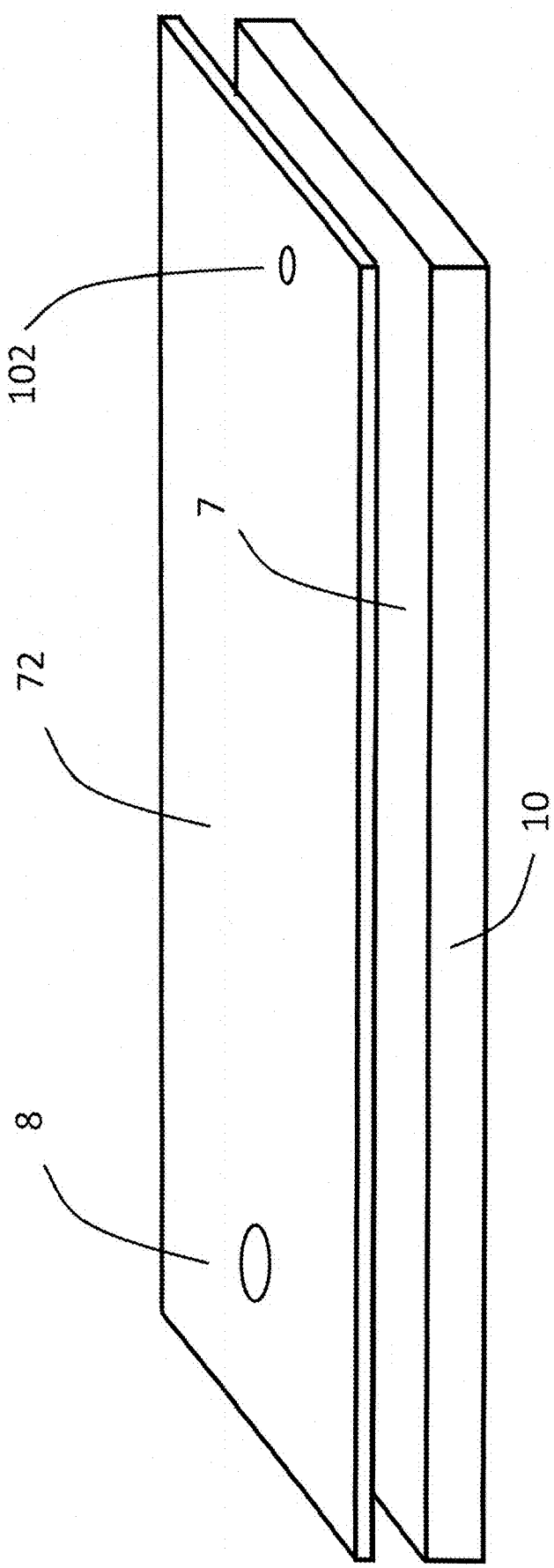
FIG. 26B is a side view schematic illustration of the pScreen™ microfluidic device for measuring DNA concentration which includes a joining channel, according to the embodiments of the invention.

In another embodiment, shown in FIG. 26, the columns 26 and 26' are joined together by a joining channel, 101, where a small venting hole 102, acting as a passive valve, is placed through the sealing layer. This passive valve provides access to atmospheric pressure to the fluid inside both columns, and thus allows the flow to move independently in both columns under the capillary pressure created by the flow meniscus of the liquid in both columns. The location of the passive valve hole is placed so that the volume of the control column from the entrance of the control column 103' to the venting hole location 102 is larger than the volume of the test column from the entrance of the test column 103 to the venting hole location 102. Thus, the liquid flowing in the control column will reach the venting hole first, as the liquid in the test column can only flow at the same speed or slower than the liquid in the control column. As soon as the liquid in the control column reaches the venting hole 102, the liquid itself seals the venting hole, creating an air pocket between the flow from the control column and the flow front of the test column, and thus stopping the liquid in the test column from moving forward. The liquid from the control column is prevented from exiting the venting hole, as the top surface of the sealing layer is hydrophobic or partially hydrophobic. Thus, in this embodiment, the control column always fills up only to the passive valve 102, at which point the test column stops. Therefore, since the volume Vo is a constant, Vm is a proxy for the number of magnetic-responsive bead clusters in the liquid sample, which is a proxy for the concentration of DNA fragments in the liquid sample. The clear advantage is that in this embodiment only Vm needs to be recorded, and the total sample volume does not need to be measured, since the passive valve 102 ensures that the assay will always end regardless the volume of the sample added, as long as the volume exceeds the minimal requirement.

In an embodiment, the venting hole has a diameter that ranges between 0.2 mm to 1.0 mm.

In an embodiment, the top surface 72 of the sealing layer around the venting hole 102 has a contact angle of between 40° and 80°.

In an embodiment, the top surface 72 of the sealing layer around the venting hole 102 is treated with a hydrophobic coating to increase the contact angle above 90°, hence further preventing liquid with surface tension lower than water from exiting the passive valve 102 by capillary action.

The devices in accordance with the embodiments of the invention, may be fabricated by methods which include, without limitation, etching each of the micro-channels on a plastic substrate using a laser etcher system, by injection mold casting in plastic, and then sealing the top of each of the micro-channels with a plastic layer by thermal bonding, or by employing hydrophilic pressure-sensitive tapes. Suitable plastic substrates, plastic sealing and injection mold casting plastics include, without limitation, poly(ethylene terephthalate) glycol, poly(lactic-co-glycolic acid) and poly(methyl methacrylate).

EXAMPLES

The present invention is more particularly described in the following non-limiting examples, which are intended to be illustrative only, as numerous modifications and variations therein will be apparent to those skilled in the art.

Example 1—Scientific Basis and Technology Feasibility of the Present Invention (A) Introduction The data presented herein describe the effect that flocculation of magnetic-responsive micro-beads in a micro-channel has on the flow resistance of liquid in the micro-channel. A liquid seeded with magnetic-responsive micro-beads in a micro-channel that is exposed to a magnetic field gradient produces a localized micro-bead flocculation. This localized micro-bead flocculation results in a localized reduction of the cross section of the micro-channel, and thus in a localized increase of the flow resistance across the flocculation region. The increase in resistance, in turn, results in an increased pressure drop across the flocculation region due to the energy loss in maintaining the flow across the reduced cross-section of the micro-channel. If the external forces responsible for the formation of the micro-bead flocculation are stronger than the flow shear-stress on the micro-beads and their aggregates, the micro-beads' flocculation increases in magnitude as more incoming micro-beads are added. In the case of a constant-pressure driven flow (relevant to the present invention), the increased pressure drop results in a reduction of the micro-channel flow rate. This study investigated and analyzed this phenomenon, and the results are reported below. These experimental results provide the scientific basis upon which the pScreen™ technology and the present invention have been developed.

(B) Experimental Methodology

Experimental data with respect to the effect of magnetic micro-bead flocculation on flow rate in micro-channels are presented. FIG. 1 is an illustration of a constant pressure flow system comprised of two micro-channels. Test micro-channel 22 (Cm) was exposed to a high-magnetic field gradient, while calibration micro-channel 20 (Co) served as a control. The pressure difference driving the flow between the micro-channel inlets 14, 14' and micro-channel outlets 16, 16' was equal between the two micro-channels 20, 22. A liquid sample 12 seeded with a known concentration of magnetic-responsive micro-beads 15 was added to both micro-channels 20, 22 and the flow rate in both micro-channels 20, 22 was recorded over time. Flocculation of the micro-beads 15 was created by means of a localized high-gradient magnetic field generated by two magnets 24, 24'.

Experiments were conducted using micro-channels fabricated from glass capillary tubes having an inner diameter of 50 μm and 100 μm. The length of the capillary tubes was varied between 3.0 cm and 7.5 cm. The magnetic field was generated by two neodymium-iron-boron (NdFeB) permanent magnets 24, 24' (25 mm×6 mm×1.5 mm; maximum surface field: 0.3 T). The magnets 24, 24' were aligned length-wise along opposite poles. The test micro-channel 22 capillary tube exposed to the magnetic field was placed between the gaps formed between the opposite poles of the NdFeB magnets 24, 24'.

Both micro-channel capillary tubes 20, 22 were partially inserted into a rubber stopper portion of a glass vacutainer tube (not shown), leaving about 0.5 cm of the ends of the capillary tubes visible. Each capillary tube inlet and outlet was inserted in a polystyrene tubing (not shown) having an inner diameter of 360 μm, which tightly fit the 360 μm outer diameter of the two micro-channel capillary tubes 20, 22. One end of the tubing lead directly to a reservoir 9 containing the liquid sample 12 with the magnetic micro-bead solution, and the other end of the tubing lead to the vacutainer tubes which collected the fluid exiting the micro-channel outlets 16, 16'. The sample reservoir 9 was open to the air, and thus was at atmosphere pressure. The vacutainer tubes were sealed and kept under a constant vacuum. The pressure difference between the sample reservoir 9 and the vacutainer tubes induced the liquid sample 12 to flow from the reservoir 9 into the vacutainer tubes. The pressure difference was maintained at 0.6 mmHg per cm of capillary tube to provide equal flow rate across capillary tubes of different lengths. Experiments were run in tandem, using two capillary tubes: one for the calibration, i.e., control, micro-channel 20; and one for the test micro-channel 22 exposed to the magnetic field gradient. Both micro-channel capillary tubes 20, 22 were kept at the same differential pressure and drew fluid 12 from the same sample reservoir 9. In the calibration micro-channel capillary tube 20, the sample 12 flowed freely. In the test micro-channel capillary tube 22, the applied magnetic field gradient induced micro-bead 15 flocculation. The calibration and test micro-channels 20, 22 were run simultaneously to eliminate common error, such as variation in atmospheric pressure, changes in viscosity due to fluctuation in temperature, and variations in micro-bead concentration. The suspension medium was 35% (by wt.) glycerol and 65% water to achieve a viscosity similar to that of blood (about 3.6 cP). Green fluorescent dye was added to the suspension medium to increase visibility of the solution exiting the two micro-channel capillary tubes 20, 22. Also added to the medium were smooth carboxyl magnetic micro-beads 15 (Spherotech, Inc.) with a diameter of 4.7 μm or 8.3 μm. Tests were conducted with a micro-bead 15 concentration between 100 micro-beads/μl and 50×10³ micro-beads/μl. Sample volumes were between 50 μl to 200 μl and initial flow rates were 0.01 μl/sec. As the sample fluid 12 exited the micro-channel capillary tubes 20, 22, it formed small drops before falling into the vacutainer. The measurement of flow rate was calculated by dividing the drop volume with the time interval between drops. The falling drop rate was recorded with a DVD video camera. Post video analysis provided the flow rate vs. time. Additional experiments were conducted without a vacutainer. The micro-channel outlets 16, 16' were connected to long polystyrene tubing (not shown) which was placed near a graduated ruler. The flow rate was measured by recording the advancement of the fluid meniscus inside the tubing as a function of time. Flow rate values in the glass calibration micro-channel capillary tube 20 not exposed to the magnetic field gradient were compared with theoretical Hagan—Poiseuille flow $Q=(\pi\alpha^4)\Delta P/8\ \mu L)$ (wherein a is the tube radius, $\Delta P$ is the pressure difference across the micro-channel, µ is the fluid viscosity, and L is the tube length) for a fully developed laminar flow of a Newtonian fluid in a cylindrical tube. Additional experiments were conducted using a micro-channel configuration as shown in FIG. 2 and fabricated in poly(lactic-co-glycolic acid) (PLGA) and Polyethylene terephthalate by laser etching as above described.

(C) Macroscopic Experimental Results and Data Analysis

Figure 11:
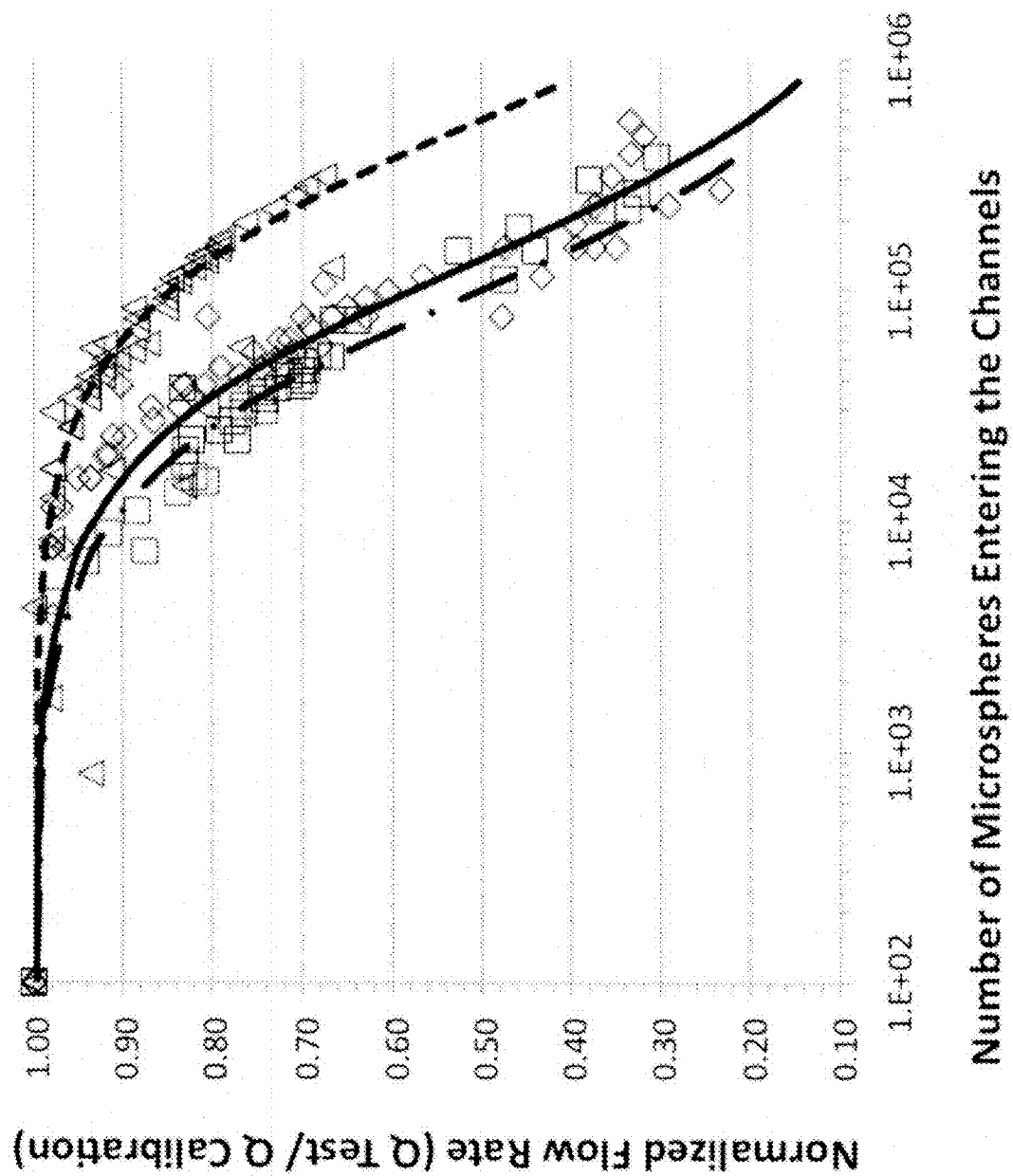
FIG. 11 is a graph showing reduction in fluid flow rate, i.e., the ratio between flow rate in the test (with magnetic field) and calibration (without magnetic field) micro-channels versus the number of magnetic-responsive micro-beads in the flocculation region.
Figure 13:
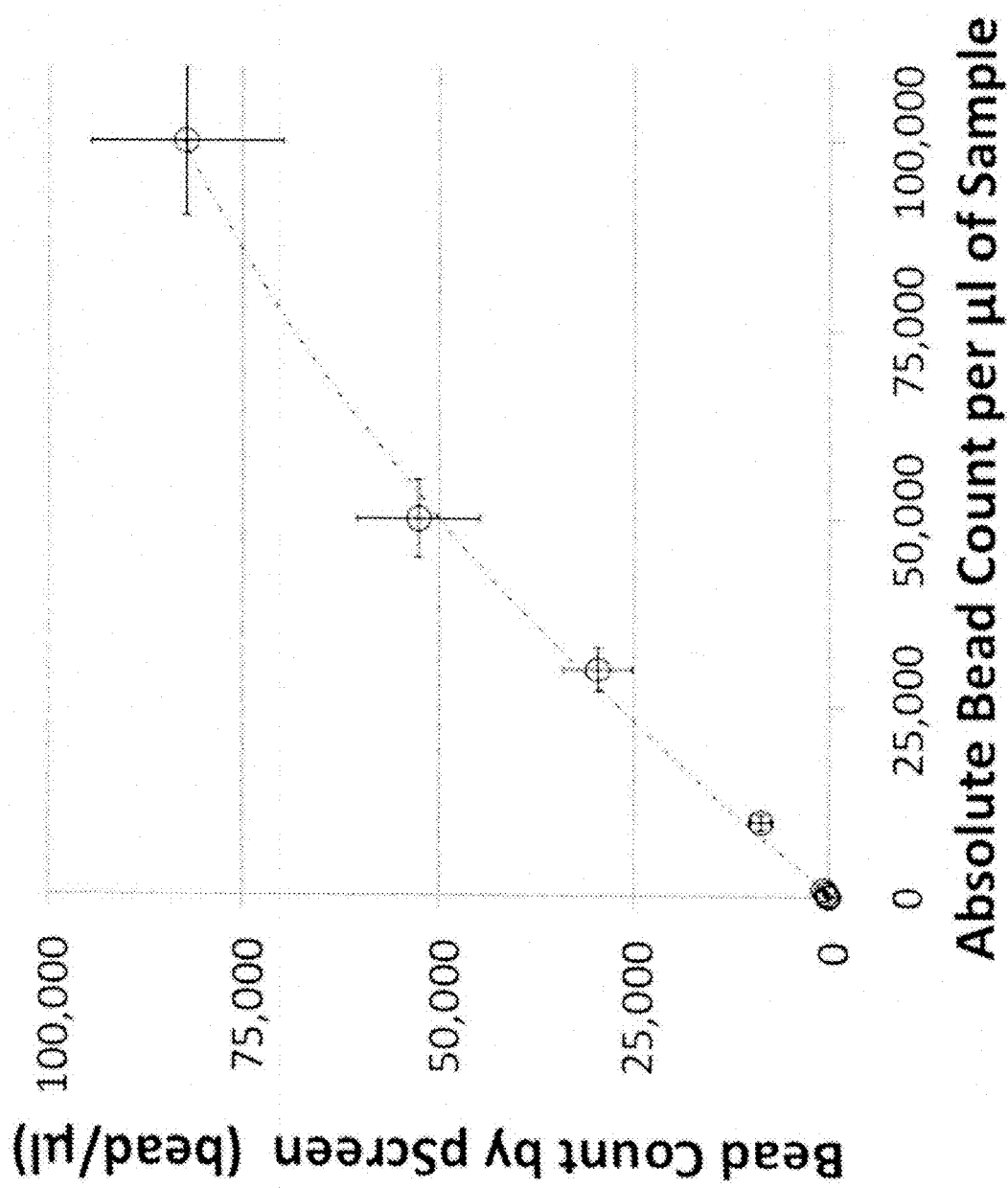
FIG. 13 is a graph showing the concentration of magnetic-responsive micro-beads in a solution obtained using the pScreen™ device versus the nominal concentration as tested by standard hemocytometry.

FIG. 11 shows the normalized flow rate, i.e., the ratio between the flow rate in the test micro-channel capillary tubes (exposed to the magnetic field gradient) and the calibration micro-channel capillary tubes (not exposed to the magnetic field gradient) versus the number of magnetic-responsive micro-beads in the flocculation region. The number of magnetic-responsive micro-beads is given by the product of the flow rate times the magnetic-responsive micro-bead concentration in the sample. The data show that the normalized flow rate is a monotonic function of the number (over three orders of magnitude) of magnetic-responsive micro-beads in the flocculation region. The amount by which the flow rate is reduced due to the pressure drop caused by the flocculation depends on the overall capillary length and the size of the flocculation zone. Thus, different aspect ratios of magnetic field length along the micro-channels versus the total length of the micro-channels also were investigated. FIG. 13 shows three data curves for different aspect ratios of magnetic field (concentrator) length versus the total length of the micro-channels [ratios range from 0.17 (triangle) to 0.24 (diamond) to 0.4 (square)]. To the investigators' knowledge, these data are the first to provide direct measurements of the effect of magnetic-responsive micro-bead flocculation on fluid flow rate in micro-channels.

(D) Data Analysis

These experimental data demonstrate that over a wide range the normalized flow rate, Qm/Qo, is a monotonic function of the number of magnetic-responsive micro-beads entering the capillary tubes. What is presented herein is a phenomenological model based on the Poiseuille equation that the investigators derived to corroborate these results. The model relates the flow rate to the reduction in micro-channel cross-section due to the formation of flocculation. The model predicts the following relationship between flow rate and number of magnetic-responsive micro-beads:

$$\hat{Q} = 1/(1+\alpha N), \quad \text{Equation (9)}$$

where α is a parameter defined below:

$$\alpha = [(a/R_{eff})^4 - 1]/LB, \quad \text{Equation (10)}$$

$$B = \tfrac{3}{4}(1-\varepsilon)(a^2 - R_{eff}^2)/r^3 \quad \text{Equation (11)}$$

where $\hat{Q}$ is the normalized flow rate, defined as Qm/Qo, N is the number of micro-beads in the flocculation, a is the capillary tube radius, $R_{eff}$ is the lumen length of the capillary tube not blocked by micro-bead flocculation, L is the capillary tube length, r the radius of the micro-beads, ε is the porosity of the micro-bead flocculation in the test micro-channel, and B is a constant that is introduced to collected different terms under a single parameter for adding simplicity and clarity to the equation form. The model predicts with high accuracy (solid lines, FIG. 11) the curve shift with changes in capillary length over magnetic field region lengths. This model provided analytical guidance for designing the specifications of the device of the present invention.

(E) Microscopic Experimental Results

Figure 12:
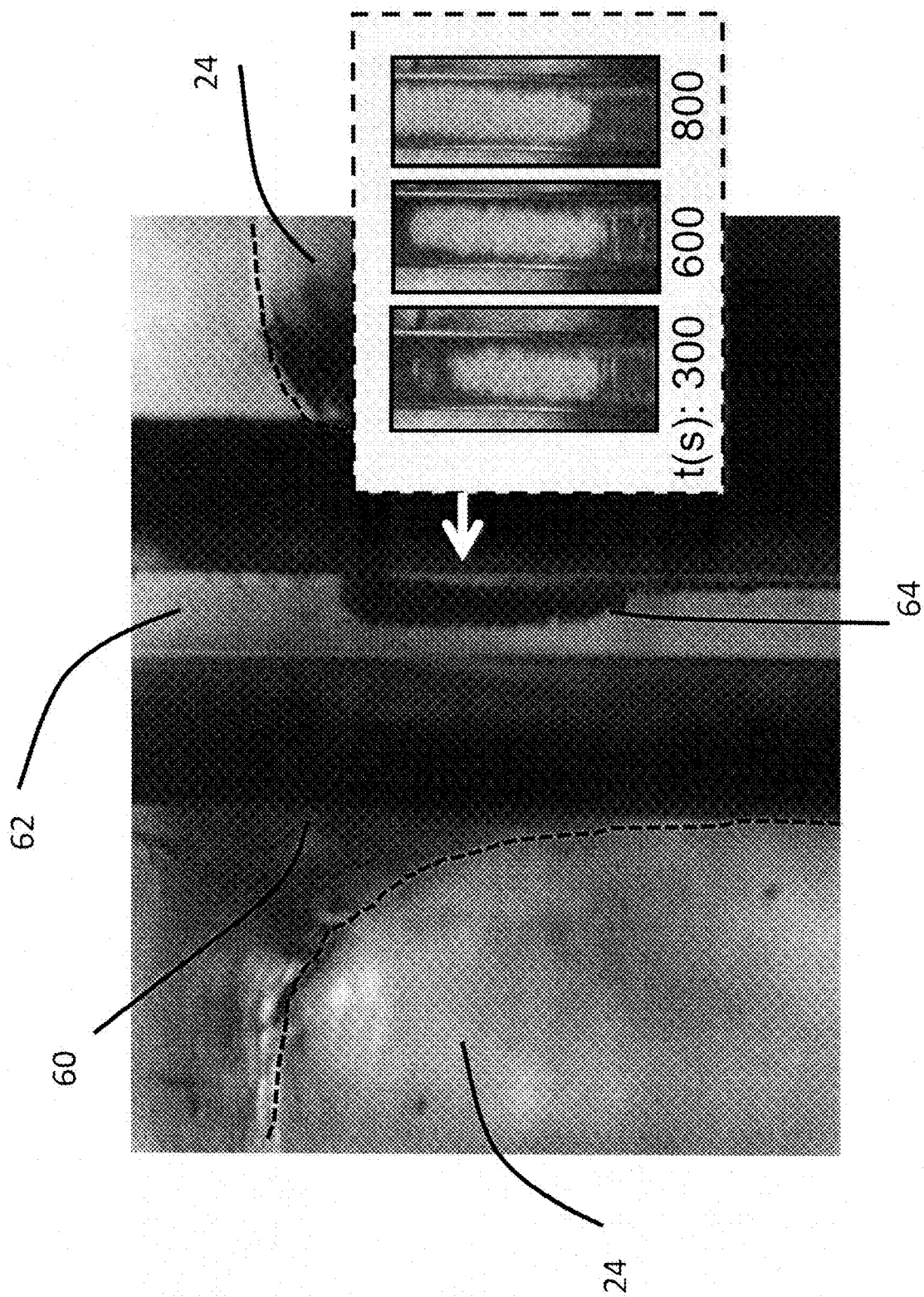
FIG. 12 is a photomicrograph showing magnetically-induced flocculation of magnetic-responsive micro-beads at a concentration of about 2,000 micro-beads/µl in a test micro-channel, according to the embodiments of the invention; the inset shows the variation in flocculation at 300 seconds, 600 seconds and 800 seconds.

In order to observe the mechanism of magnetically-induced flocculation, microscopic studies were performed using an inverted microscope (Olympus, IX70, 20× magnification). This phenomenon was visualized using a solution seeded with RBC-sized magnetic-responsive micro-beads, having a diameter of 4 µm or 8 µm, in capillary tubes having a diameter of 50 µm or 100 µm. FIG. 12 shows an example of flocculation 64 formed in a capillary channel 62 with glass walls 60, using a 2,000 micro-beads/µl analog solution. Flocculation initially formed at the leading edge of the magnet 24 (corresponding to the greatest magnetic field gradient.) The size of the flocculation grew over the entire length of the magnetic field region. When the size of the flocculation covered the length of the magnetic field region, the flocculation behaved as a fluidized bed. Magnetic-responsive micro-beads downstream were released, while upstream incoming magnetic-responsive micro-beads were added to the flocculation.

Example 2—pScreen™ Prototype Fabrication and Testing

(A) Fabrication

Two sets of pScreen™ prototypes were fabricated: (1) a bench top prototype with multiple micro-channels for simultaneous testing of various samples; and (2) a single-use, portable, lab-on-card device. The pScreen™ bench-top prototype was described in the previous section. The pScreen™ lab-on-card prototype was realized using standard microfluidics fabrication techniques. In brief, the micro-channels were etched using a laser etcher system on a poly(ethylene terephthalate) glycol (Petg) substrate. The channels then were sealed using a matching poly(lactic-co-glycolic acid) (PLGA) top by thermal bonding using a hot press. The magnetic field gradient was obtained by placing two small magnets in an N-S configuration underneath the test channel. The pScreen™ lab-on-card prototype also was fabricated using injection cast molding in which the prototype was fabricated in poly(methyl methacrylate) (PMMA).

(B) Experimental Data for a Microfluidic Device for Detecting and Quantifying the Concentration of Magnetic Micro-Beads Two pScreen™ prototypes were tested using a variety of fluids such as, without limitation, blood, blood-analogs, or PBS buffer solution with different concentrations of surfactant. Tests were conducted using magnetic-responsive micro beads having a diameter of 4.1 µm or 8 µm. Sample concentrations between 100 micro-beads/µl and 200,000 micro-beads/µl were used. The concentration of magnetic-responsive micro-beads was determined by recording the level of the fluid on the calibration and test graduated column scales. Each mark on the scale corresponded to a given amount of fluid volume which flowed through the micro-channels. The relationship derived in Equation 8 was applied to convert the recorded volumes in magnetic-responsive micro-bead concentration. The analytic expression of the relationship between the volumes Vo and Vm, specific for the tested prototypes, was derived by computing Equations (5) through (8), with $\dot{Q}$ given in Equations (9) through (11). To be especially noted is the fact that all of the equations provided above do not include time as a variable. Hence, it is not necessary to monitor/read the device's result at any specific time. The device reading at any time provides the same read-out. FIG. 13 is a graph showing magnetic-responsive micro-bead concentration measured using the pScreen™ device (y-axis) of the present invention versus magnetic-responsive micro-bead concentration measured with a standard hemocytometer (x-axis).

(C) Experimental Data for a pScreen™ Immunoassay

Figure 14:
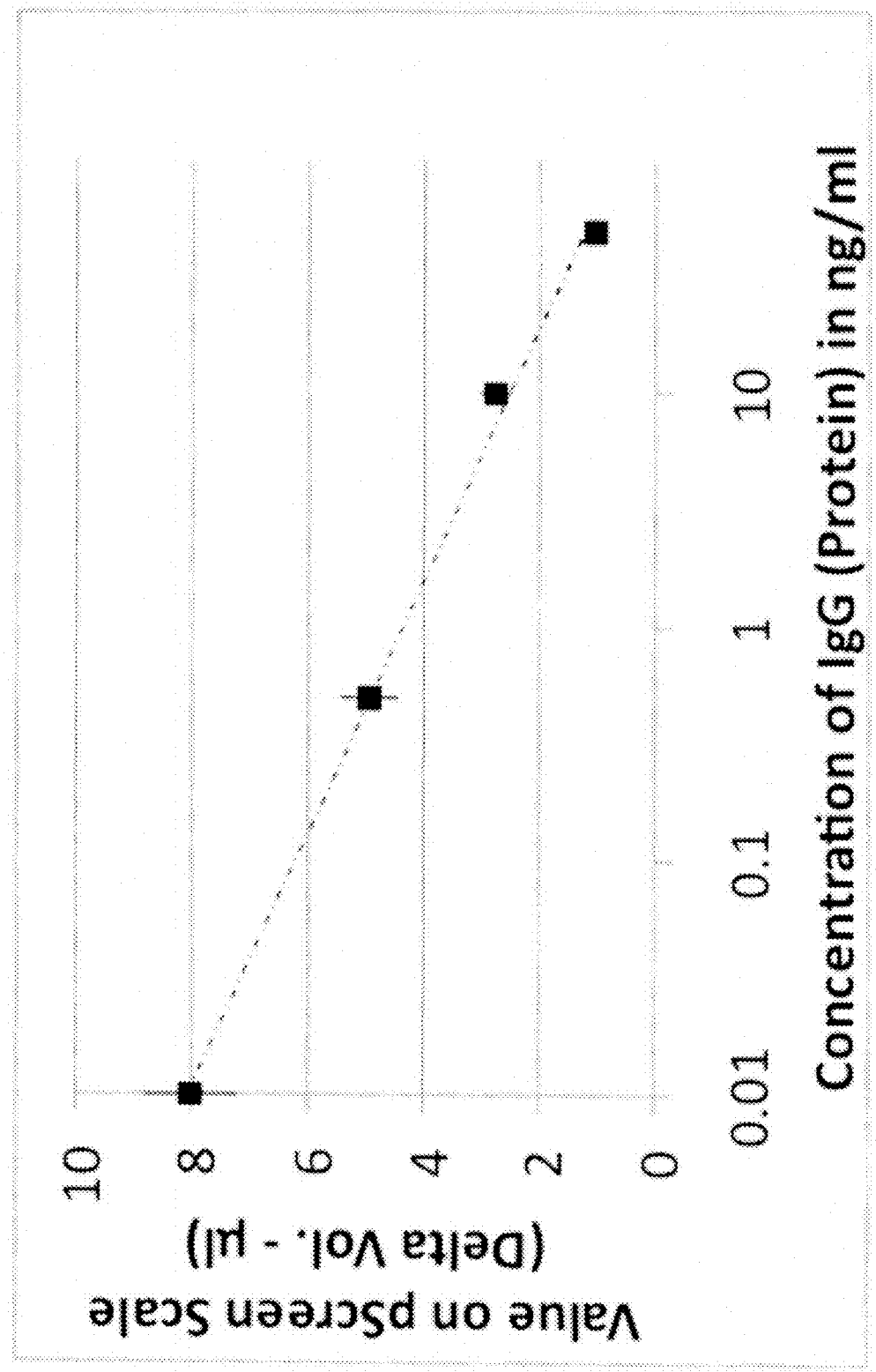
FIG. 14 is a graph showing the concentration of immunoglobulin (IgG) in a solution obtained using the pScreen™ immunoassay.

Several pScreen™ immunoassay prototypes were tested using buffer solutions containing various concentrations of mouse-IgG antibody prepared by titration from a known concentration IgG standard. The concentration of mouse-IgG antibody ranged from 0.5 ng/ml to 100 ng/ml. Tests were conducted using magnetic-responsive micro-beads coated with anti-mouse IgG antibody and coating the surface of a reaction chamber with anti-mouse IgG antibody. Sample volume ranged from 30 µl to 60 µl. The IgG antibody concentration was determined by recording the level of the fluid on the calibration and test graduated column scales. Each mark on the scale corresponded to a given amount of fluid volume which flowed through the micro-channels. FIG. 14 is a graph showing the difference between the volume collected in the control column (Vo) and the volume collected in the test column (Vm) (y-axis) versus the known concentration of IgG antibody (x-axis).

Examples 3 to 6 provide guidance regarding the detection and quantification of magnetic-responsive micro-beads and amount of analyte in a liquid sample. Also provided are examples showing how to obtain a set of calibration curves for any embodiment by means of the claimed proxies herein, i.e., between the ratio Qm/Qo, the difference Qo−Qm, and the ratio $(Qo-Qm)^p/(Qm)^q$, and the number of magnetic-responsive micro-beads and the concentration of analyte in a fluid. The examples provided show how to derive Equation 8 for any specific embodiment and provide working examples for a selected embodiment. Equation 8 is a direct result of the claimed proxy between the ratio Qm/Qo and the number of magnetic-responsive micro-beads. Equation 8 converts the volume of liquid sample passing through the control micro-channel, Vo, and through the test micro-channel, Vm, into the magnetic-responsive micro-bead concentration and the analyte concentration in a liquid sample.

Example 3—Proxy Relationships Between Flow Rate and Micro-Bead Concentration

The present invention provides a method of detecting and quantifying the concentration of magnetic-responsive micro-beads in a liquid sample, by calculating the ratio Qm/Qo, the difference Qo−Qm, and the ratio $(Qo-Qm)^p/(Qm)^q$, wherein p and q are derived through a calibration process, wherein the ratios Qm/Qo and $(Qo-Qm)^p/(Qm)^q$ are a proxy for the number of magnetic-responsive micro-beads in the liquid sample, and then quantifying the concentration of magnetic-responsive micro-beads in the liquid sample.

Three methods are provided to show how to use these proxy relationships and how to derive in practice the number of magnetic-responsive micro-beads in a liquid sample. The first method analytically derives these relationships from the physical dimensions of a specific embodiment. The second method provides a calibration process that enables the calibration of any embodiment. The third method teaches how to use the volume of sample passing through the control micro-channel, Vo, and through the test micro-channel, Vm, to derive the concentration of magnetic-responsive micro-beads.

Method 1. Relationship Between Normalized Flow Rate, Qm/Qo, and Number of Micro-Beads The relationship between the normalized flow rate, Qm/Qo, and the number of micro-beads entering the capillary tubes (i.e., micro-channels) is analytically derived for a specific embodiment having the following dimensions and values:

Test micro-channel and calibration (control) micro-channel: each with a circular cross-section with a radius of 50 µm; and a length of 15 mm.
Micro-beads: radius of 2 µm
Porosity of the flocculation: 0.55
Pressure difference between the inlet and outlet of both micro-channels: maintained constant at about 1 mmHg per cm.

The flow rate in the control micro-channel, Qo, is described by the Hagen-Poiseuille equation, and is equal to:

$$Q_o = \Delta P/R_o, \text{with: } R_o = 8 \mu L/(\pi \alpha^4), \quad \text{Equation (12)}$$

where $\Delta P$ is the pressure drop across both micro-channels; Ro is the micro-channel's flow resistance; µ is the liquid sample viscosity; α is the micro-channel's radius, and L is the micro-channel's length.

The flow rate in the test micro-channel, Qm, is given by:

$$Q_m = \Delta P/R_m, \text{with: } R_m = 8\mu(L-\lambda)/(\pi \alpha^4) + \mu \lambda/(\pi \alpha^2 k), \quad \text{Equation (13)}$$

where λ is longitudinal section of the length of the test micro-channel occupied by the micro-bead flocculation; L−λ is the remaining length of the micro-channel flocculation-free; and k is the Darcy's constant. The first term in Equation 13 is the Hagen-Poiseuille equation for the flocculation-free section of the test micro-channel, and the second term is Darcy's law for the section of the test micro-channel occupied by the micro-bead flocculation. Darcy's law is known by those skilled in the art to accurately describe flow of fluid through packed micro-beads and micro-bead flocculation. In this example, the Reynolds' number is low (<2) (Reynolds' number depends on an embodiment's physical dimensions and flow rates, and is a well know parameter that describes the physical properties of fluid in a flow), and thus the Darcy's constant takes the known form:

$$k = r^2 \varepsilon^3/(15(1-\varepsilon)^2), \quad \text{Equation (14)}$$

where ε is the porosity of the micro-bead flocculation in the test micro-channel, i.e., the fraction of volume of the test micro-channel not occupied by the micro-beads; and r is the micro-bead's radius.

Taking the ratio of Equation 13 over Equation 12, one gets:

$$Q_m/Q_o = R_o/R_m = \frac{8 \mu L}{\pi a^4} / \left[ 8\mu(L-\lambda)/(\pi a^4) + \mu \lambda/(\pi a^2 k) \right]$$

By rearranging the terms in the above equation, one gets:

$$Q_m/Q_o 1/[1+(\lambda/8L)\cdot(\alpha^2/k-1)]. \quad \text{Equation (15)}$$

It is noted that Equation 15 does not contain liquid sample viscosity.

The longitudinal section of the length of the test micro-channel occupied by the micro-bead flocculation, $\lambda$, increases with the number of micro-beads, N, that have entered the test micro-channel and formed the flocculation under the effect of the magnetic field. These quantities, $\lambda$ and N, thus are related by the following identity:

$$\lambda = N/\hat{\mathcal{Q}}, \text{ with: } \hat{\mathcal{Q}} = \tfrac{3}{4}\alpha^2(1-\varepsilon)/r^3 \qquad \text{Equation (16)}$$

where $\hat{\mathcal{B}}$ a constant that is introduced to collect different terms under a single parameter for adding simplicity and clarity to the equation.

By putting Equation 16 into Equation 15, one gets:

$$Q_m/Q_o = 1/[1+(N/8L\,\hat{\mathcal{B}})(a^2/k-1)] \qquad \text{Equation (17)}$$

or alternatively, $$Q_m/Q_o = 1/[1+\alpha\hat{\alpha}], \text{ where: } \alpha = (\tfrac{1}{8}L\,\hat{\mathcal{B}})(a^2/k-1)$$

Equation 17 provides the relationship that enables the measurement of the number of micro-beads by measuring the ratio Qm/Qo. Thus, in this example, Equation 17 becomes:

$$Q_m/Q_o = 1/[1+2.63\times 10^{-6}\cdot N], \qquad \text{Equation (18)}$$

In this example, Equation 18 is used as follows:

Given a fluid sample of unknown micro-bead concentration, for which the concentration needs to be determined, the operator first runs the sample through the micro-channels as described above and measures periodically the flow-rates, Qm and Qo. The measurements can be done at any time while the liquid sample is flowing into the micro-channels. Then, by putting the ratio, Qm/Qo, obtained from each measurement into Equation 18, the operator gets the number of micro-beads that have entered the test micro-channel, N, at the time the flow rate measurements have been taken. To compute the micro-bead concentration, the operator divides the value of N by the total volume of fluid that passed through the test micro-channel at the time flow rate measurements have been taken, which also is equal to the sum of the products of the test micro-channel flow rates by the length of the time interval between measurements. The shorter the time interval between measurements, the more precise is the obtained value of the number of micro-beads and of the micro-bead concentration. Table 1 provides the values obtained in this example:

TABLE 1

| Time (second) | Qo μl/sec | Qm μl/sec | Qo/Qm | N | Vm (μl) | Concentration (micro-beads/μl) |
|---|---|---|---|---|---|---|
| 54 | 0.01 | 0.0100 | 1.000 | 0.0E+00 | 8.5 | 0.0E+00 |
| 906 | 0.01 | 0.0094 | 0.940 | 4.0E+04 | 17.1 | 2.3E+03 |
| 1818 | 0.01 | 0.0093 | 0.934 | 4.4E+04 | 26.1 | 1.7E+03 |
| 2778 | 0.01 | 0.0089 | 0.888 | 7.9E+04 | 35.0 | 2.3E+03 |
| 3786 | 0.01 | 0.0085 | 0.845 | 1.1E+05 | 43.8 | 2.6E+03 |
| 4830 | 0.01 | 0.0082 | 0.816 | 1.4E+05 | 52.6 | 2.7E+03 |
| 5910 | 0.01 | 0.0079 | 0.789 | 1.7E+05 | 61.4 | 2.7E+03 |
| 7026 | 0.01 | 0.0076 | 0.763 | 1.9E+05 | 70.3 | 2.8E+03 |
| 8190 | 0.01 | 0.0073 | 0.732 | 2.3E+05 | 79.1 | 2.9E+03 |
| 9390 | 0.01 | 0.0071 | 0.710 | 2.6E+05 | 87.8 | 2.9E+03 |
| 10614 | 0.01 | 0.0070 | 0.696 | 2.7E+05 | 96.6 | 2.8E+03 |

Table 1 shows the time in seconds at which each measurement was taken; the experimental measurements of the flow rate, Qo, in μl/second in the control micro-channel; and the flow rate, Qm, in μl/second in the test micro-channel. (For the method to work, it is not important how the flow rates, Qo and Qm, are measured. For example, the flow rates can be measured by using commercially available flow meters placed in series with the micro-channels, or as described in detail above in Example 1. The ratio, Qm/Qo, then is computed and shown in the table's fourth column, from which the number of micro-beads, N, is derived using Equation 18 and shown in the table's fifth column. The volume, Vm, is calculated by taking the sum of the products of the test micro-channel flow rates by the length of the time interval between measurements, and is shown in the table's sixth column (alternatively, the volume, Vm, also can be measured as an independent variable, as described above). Then, micro-bead concentration is derived by dividing the N column by the Vm column, with the result shown in the table's seventh column. It is noted that the concentration slightly varies between measurements, and thus to obtain a more precise value, the average of these measurements may be taken. In this example, the micro-bead concentration is equal to 2,570 micro-beads/μl of liquid sample.

Equation 18 provided herein was derived for this specific embodiment. A person skilled in the art, however, would understand that following the same process, the relationship between the normalized flow rate and the number of micro-beads entering the test micro-channel can be derived for other embodiments by putting the appropriate value of the Darcy s constant in Equation 15. The Darcy's constant is well known by those skilled in the art to depend on the micro-channels' shape, geometry, physical dimensions, design, flow rates, as well as an embodiment's Reynolds number. By using the appropriate Darcy's constant, the invention may be practiced for other embodiments having, for example, non-cylindrical micro-channels and/or non-spherical micro-beads, and/or non-uniformly-sized micro-beads.

In addition, for other embodiments, in which micro-bead flocculation does not occupy the entire test micro-channel's cross-section, but only occupies outer layers, the relationship between the normalized flow rate, Qm/Qo, and the number of micro-beads entering the capillary tubes is given in Equations 9 to 11.

Method 2. Calibration Process

Provided herein is the construction of a set of calibration curves which provide the relationship between the normalized flow rate, Qm/Qo, and the number of micro-beads entering the test micro-channels. The method described herein allows one to avoid the need to use complex analytical expressions, which for some embodiments may be too complex to be represented in a mathematical closed form such as Equation 18.

For a given embodiment, the calibration process involves running a liquid solution containing a known concentration (the calibration solution) of magnetic-responsive micro-beads through the control and test micro-channels, as shown in FIGS. 1 and 4. The flow rates, Qm and Qo, then are measured at different time intervals and recorded, and the total volume passing through the test micro-channel also is recorded, as described above. The shorter the time interval between recordings, the more precise is the resulting calibration curve. For each value of flow rate recorded, the number of micro-beads that have entered the test micro-channel and added to the flocculation is computed by taking the product between the volume, Vm, passing through the test micro-channel and the value of the known concentration of the micro-beads. Then, the ratio, Qm/Qo, for each measurement is plotted versus the number of micro-beads computed, as previously described. The process may be repeated multiple times using calibration solutions with different known values of micro-bead concentration; the more times this process is repeated, the more precise are the calibration curves. An example of these plots is shown in FIG. 11 for the embodiment described in the Example 1. Using this calibration curve, micro-bead number in any tested fluid of unknown concentration can be determined from the observed ratio, Qm/Qo, by reading the horizontal value (the micro-bead number) on the calibration curve corresponding with the vertical value (the observed ratio, Qm/Qo) observed during the measurement. The concentration of the calibration solutions are prepared to approximate the expected range of concentration of the liquid samples to be tested.

The same process can be repeated to derive calibration curves that relate the ratio, $(Qo-(Qm)^p/((Qm)^q$, with micro-bead concentration in a liquid sample. In this case, the parameters, p and q, are obtained as followed. A solution containing a known concentration of micro-beads and of known volume is passed through the micro-channels and the flow rates, Qm and Qo, are measured. Then, an identical solution is passed through the micro-channels but with a higher flow rate, Qo. This process is repeated at least three times, with flow rates, Qo, which cover the range of flow rates, Qo, for which the embodiment is expected to be used. Then, $(Qo-Qm)^p/(Qm)^q$, with p and q set equal to 1, are plotted for each solution versus the number of micro-beads entering the test micro-channel (determined as previously described) to obtain a set of calibration curves. Then, p and q are independently varied until each curve $(Qo-Qm)^p/(Qm)^q$ collapses on each other to form a single curve. A method to optimize p and q is to solve the following set of equations.

$$[(Q_o-Q_m)^p/Q_m^p]_n^1 = [(Q_o-Q_m)^p/Q_m^p]_n^2$$

$$[(Q_o-Q_m)^p/Q_m^p]_n^1 = [(Q_o-Q_m)^p/Q_m^p]_n^3$$

where the superscript numbers 1, 2, and 3 refers to the calibration curve number, and the subscript N indicates that the values of Qo and Qm in the square brackets are taken when the number of micro-beads entering the test micro-channel is equal to N. The value of N can be chosen arbitrarily, and the process may be repeated for different N values to obtain a more accurate value of p and q across the entire range of numbers of micro-beads.

Method 3. Conversion from Volume to Micro-Bead Concentration—Equation 8 Working Example Provided herein are two processes which may be used for any embodiment in order to convert the volume of sample passing through the control micro-channel, Vo, and the test micro-channel, Vm, into magnetic-responsive micro-bead concentration and concentration of analyte in a liquid sample. The first process analytically derives these relationships from the physical dimensions of the embodiment. The second process provides a calibration method that enables calibration of any embodiment and shows the use of the embodiment in practice.

Process A

Provided is a working example showing how Equations 5 through 8 enable one to derive the concentration of micro-beads in a liquid from the ratio Qo/Qm, using the same dimensions provided above in Method 1 (spherical micro-beads with a radius of 2 μm, micro-channels having a length of 15 mm and a radius of 50 μm, and Qo equal to 0.0 μl/second), and for which the ratio, Qm/Qo, versus the number of micro-beads is provided by Equation 18. By putting Equation 18 into Equation 5, one gets:

$$N_0 = \int_0^{Nm} \frac{dN'}{(1/(1+(2.63 \times 10^{-6}) \cdot N'))} \quad \text{Equation (19)}$$

where No is the number of magnetic responsive micro-beads that are passing through the control micro-channel, Nm is the number of magnetic responsive micro-beads that are passing through the test micro-channel, and the prime symbol inside the integral, N', indicates, according to standard convention, that the integral operation is computed on an N variable. Equation 19 is the specific example, for a specific embodiment, of generic Equation 6. By solving the integral, one gets:

$$N_o = N_m + \frac{2.63 \times 10^{-6}}{2}(N_m)^2 \quad \text{Equation (20)}$$

Since No is equal to the product of the magnetic responsive micro-bead concentration, p, times the volume of sample passing through the control micro-channel, Vo; and since Nm is equal to the product of the magnetic responsive micro-bead concentration, ρ, times the volume of sample passing through the test micro-channel, Vm, Equation 20 can be rewritten as:

$$V_o\rho = V_m\rho + \frac{2.63 \times 10^{-6}}{2}(\rho V_m)^2; \quad \text{Equation (21)}$$

$$\text{or: } V_o - V_m = \frac{2.63 \times 10^{-6}}{2}(V_m)^2\rho$$

Equation 21 can easily be rearranged as follows:

$$\rho = (V_0 - V_m) / \left(\frac{2.63 \times 10^{-6}}{2} V_m^2\right) \quad \text{Equation (22)}$$

Equation 22 provides a simple expression that can be used to derive the concentration of micro-beads for any liquid sample with unknown concentration of micro-beads from the measurements of the volumes, Vo and Vm, in this working example. In other words, Equation 22 is a specific example of generic Equation 8. For example, a liquid sample containing an unknown concentration of magnetic-responsive micro-beads is run through the control and test micro-channels, as described above. To obtain the value of this unknown concentration, the volume of the fluid passing through the control micro-channel, Vo, and the volume of fluid passing through the test micro-channel, Vm, are recorded, as described above. Then these values, Vo and Vm, are put into Equation 22 to derive the concentration of magnetic-responsive micro-beads.

Process B

Figure 15:
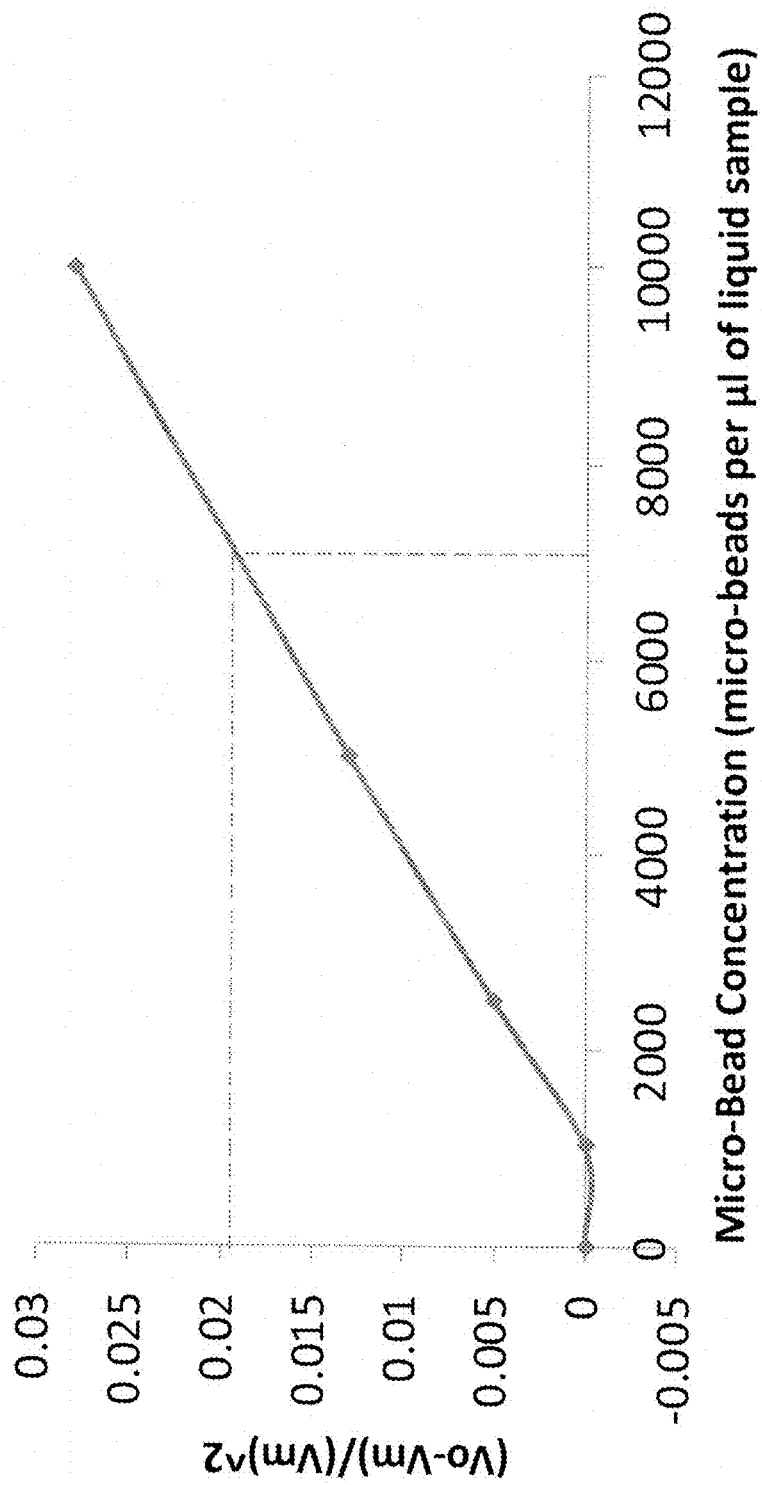
FIG. 15 is a graph showing a calibration curve describing the relationship between $(Vo-Vm)/(Vm)^2$ and the concentration of magnetic-responsive micro-beads, according to the embodiments of the invention.

Provided herein is an example showing how to construct calibration curves for the relationship between volumes, Vo and Vm, and concentration of micro-beads. The process allows one to avoid the need to use complex analytical expressions, which for some embodiments may be too complex to be represented in a simple closed form such as Equation 22. For a given embodiment, a series of solutions of known volume and containing known concentrations of magnetic-responsive micro-beads are passed through the control and test micro-channels, as described above. The concentrations of these test (calibration) solutions are chosen to span the entire range of micro-bead concentrations in the samples to be tested. The volumes, Vo and Vm, then are measured. For the lab-on-card microfluidic pScreen™ magnetic-responsive micro-bead concentration counter embodiment, the volumes, Vm and Vo, can be measured by reading the scale on the control column (Co) and the test column (Cm). Once Vm and Vo have been recorded for all solutions, the ratios, $(Vo-Vm)/(Vm)^2$, are plotted as a function of micro-bead concentration. This plot provides a calibration curve that enables the invention to be reduced to practice. Using this calibration curve, the micro-bead concentration of an unknown fluid can be determined from the observed difference, ratio $(Vo-Vm)/(Vm)^2$, by reading the horizontal value (micro-bead concentration) on the calibration curve corresponding with the y value $(Vo-Vm)/(Vm)^2$ observed during the test, as shown in FIG. 15. For example, as shown in FIG. 15, if the measurement of Vm and Vo for a solution with an unknown micro-bead concentration gives a ratio of $(Vo-Vm)/(Vm)^2$ equal to about 0.02, then the micro-bead concentration would be about 7500 micro-beads/µl. The calibration curve shown in FIG. 15 was obtained using the embodiment shown in FIG. 2, in which the micro-channels' radii is 46 µm, the length of the micro-channels is 15 mm, and the radius of the micro-beads is 2.35 µm.

Example 4—Proxy Relationships Between Flow Rate and Concentration of Analyte in a Liquid Sample The present invention provides a method of detecting and quantifying the concentration of magnetic-responsive micro-beads in a liquid sample, by calculating the ratio Qm/Qo, the difference Qo–Qm, and the ratio $(Qo-Qm)^p/(Qm)^q$, wherein the ratios Qm/Qo and $(Qo-Qm)^p/(Qm)^q$ are a proxy for the number of magnetic-responsive micro-beads in the liquid sample, which is a proxy for the concentration of analyte in the liquid sample, and then quantifying the concentration of analyte in the liquid sample, as described below.

As described above, the concentration of magnetic-responsive micro-beads exiting the reaction chamber and entering the two micro-channels is proportional to the concentration of the analyte in the liquid sample. As described herein, the concentrations of these micro-beads are detectable and quantifiable by either using the ratio Qm/Qo or the values Vo and Vm. Thus, in order to derive the concentration of analyte in a liquid sample, the relationship between the concentration of analyte and the concentration of micro-beads exiting the reaction chamber needs to be calibrated. Two methods are provided, as follows:

Method 1

The first method consists of running a sample with a known concentration of analyte through the reaction chamber and then counting the number of micro-beads binding to the reaction chamber's surface, as shown in FIGS. 8 and 9. The number of micro-beads exiting the reaction chamber is equal to the total number of micro-beads deposited in the reaction chamber (as described above) minus the number of micro-beads binding to the reaction chamber's surface. The process is repeated multiple times using a series of calibration samples obtained from the initial sample by titration. Then the concentration of micro-beads exiting the reaction chamber obtained for each calibration test is plotted as a function of the analyte concentration. In practice, the sample with unknown concentration of analyte is processed as described above and schematically shown in FIGS. 1 and 7. The concentration of micro-beads entering the micro-channels, i.e., the concentration of micro-beads exiting the reaction chamber, is derived as described above. Then, using the calibration curve derived and described above, the concentration of micro-beads is converted into the concentration of analyte.

Method 2

The second method enables the user to derive the calibration curve for any embodiment without counting the number of micro-beads binding to the reaction chamber's surface. To calibrate for any embodiment, a series of solutions of known volume, containing known concentrations of target analyte, are run through the device as described above. The concentrations of these test (calibration) solutions are chosen to span the entire range of expected analyte concentrations of the sample to be tested. The difference, Vo–Vm, between the control micro-channel volume, Vo, and the test micro-channel volume, Vm, is measured for each tested calibration sample and plotted as a function of the calibration sample's analyte concentration. Using this plot (calibration curve), the target analyte in any tested fluid can be determined from the observed difference in volume, Vo–Vm, by reading the horizontal value (analyte concentration) on the calibration curve corresponding with the vertical value (the Vo–Vm difference) observed in the test.

Example 5—Working Example—Quantification of Concentration of Micro-Beads in a Liquid Sample Quantification of the concentration of micro-beads in a liquid sample is performed by using the pScreen™ immunoassay shown in FIG. 2, and having the dimensions as described above in Method 3, Process A. To measure the concentration of micro-beads, the user performs the following steps:
  Step 1: Take 50 µl of sample solution and place it on the device inlet.
  Step 2: Wait for the sample to flow into the device columns, typically less than 20 minutes.
  Step 3: Read the values of the fluid volumes, Vo and Vm, filling up each column using the scale on the side of the column.
  Step 4: Compute the ratio $(Vo-Vm)/(Vm)^2$.
  Step 5: The concentration of micro-beads is equal to ratio $(Vo-Vm)/(Vm)^2$ divided by $1.3 \times 10^{-6}$.

Example 6—Working Example—Quantification of Analyte Concentration in a Liquid Sample Quantification of the concentration of an analyte in a liquid sample is performed by using the pScreen™ immunoassay shown in FIG. 3, and the calibration curve shown in FIG. 15. To measure the concentration of the analyte, the user performs the following steps:

Step 1: Take 50 µl of sample solution and place it on the device inlet.

Step 2: Wait for the sample to flow into the device columns, typically less than 20 minutes.

Step 3: Read the values of the fluid volumes, Vo and Vm, filling up each column using the scale on the side of the column.

Step 4: Compute the ratio $(Vo-Vm)/(Vm)^2$.

Step 5: Read, on the calibration plot, the analyte concentration on the horizontal axis of the calibration curve corresponding to the value of the $(Vo-Vm)/(Vm)^2$ ratio on the vertical axis.

Example 7—System of Valves

Figure 21:
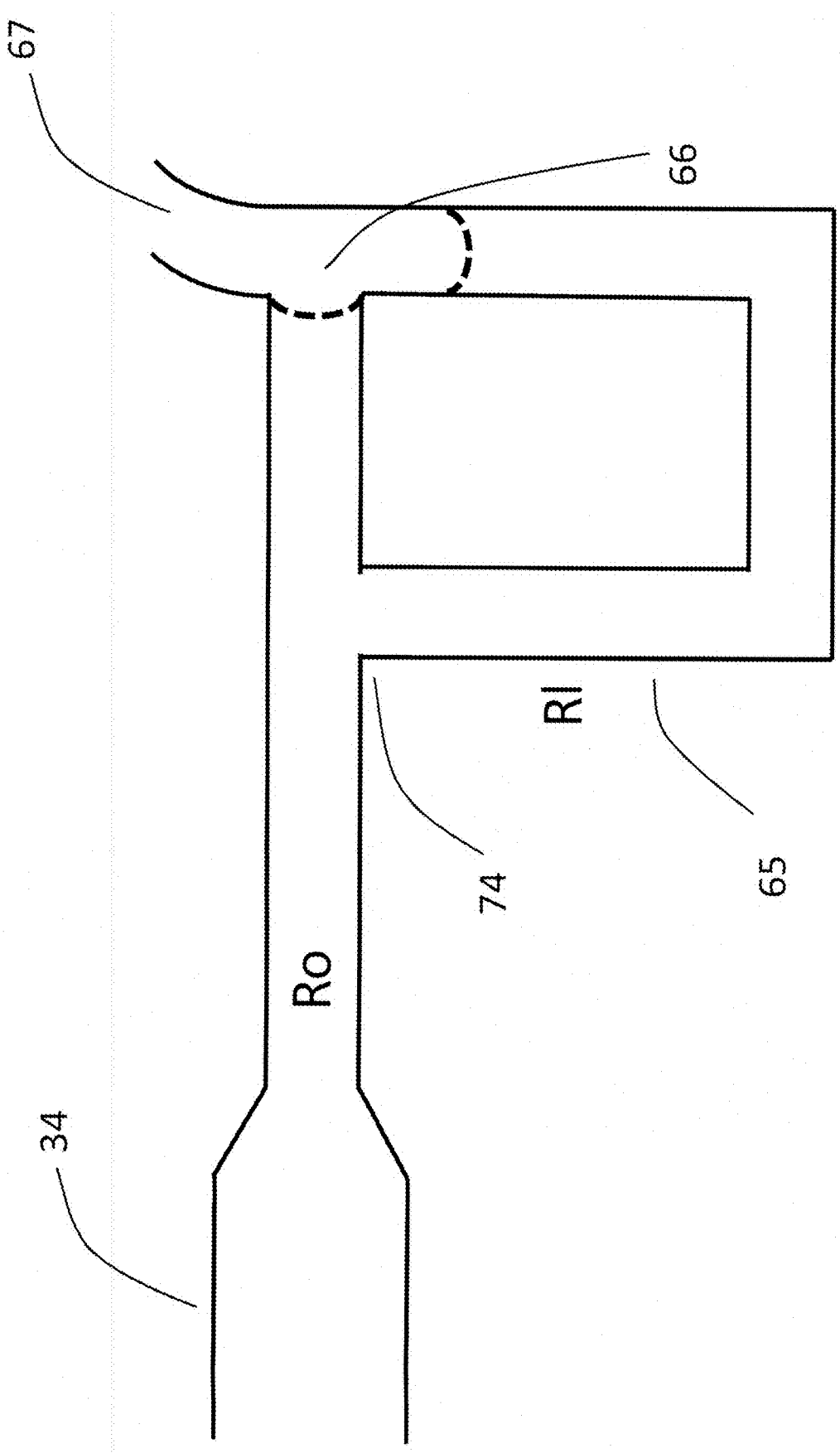
FIG. 21 is a schematic illustration of one reaction chamber, one outlet micro-channel manifold, and a delay micro-channel. Ro represents the fluid resistance of the sum of the reaction chamber and outlet manifold micro-channel, and R1 represents the fluid resistance in the delay micro-channel, in accordance with the invention.

By introducing a system of valves in the present invention, the incubation time can be adjusted by varying the length of the delay micro-channel. For any practical purpose, the incubation time is equal to the delay time, which is the time it takes fluid to travel the entire length of the delay micro-channel from the primary flow splitter 74 to the connector 67 (shown in FIG. 21). This time depends on several factors, including fluid type, delay micro-channel contact angle, delay micro-channel width, depth, and length, and reaction chamber and inlet manifold's fluid dynamic resistance. The delay time is the time t that satisfies the following equation:

$$l = \frac{1}{R^{\dot{U}}}\left(\sqrt{R_0^2 + 2D} - R^{\dot{U}}\sqrt{R_0^2}\right), \quad \text{Eq. 23}$$

where the following definitions apply:

$$R^{\dot{U}} = \frac{12\,\mu}{wh^3(1 - 0.63h/w)}$$

$$D = \frac{\gamma(\cos(\theta_c)/r_c)}{wh}$$

and, where: t, l(t), w, h, µ, γ, $\theta_c r_c$, $R_0$ are, respectively, the time it takes for the fluid to travel the entire length of the delay micro-channel; the length, width and depth of the delay micro-channel, the viscosity of the liquid sample, the surface energy of the liquid sample, the mean of the contact angle of the liquid sample with the walls of the delay micro-channel, the hydraulic radius of the delay micro-channel, and the sum of the flow resistances of the inlet manifold, reaction chamber, and outlet manifold micro-channels. Because of the complex physical behavior at the fluid meniscus, especially with a non-Newtonian liquid sample such as whole blood, the above equation provides only an approximate solution, and the desired value needs to be determined experimentally in each case.

As a specific example, a series of experimental tests were performed and results were obtained using whole blood, a device made of PMMA, sealed with a hydrophilic tape, having a contact angle between the fluid meniscus and the PMMA surface of between about 70 degrees and about 80 degrees, and between the fluid meniscus and the hydrophilic tape of between about 10 degrees and about 34 degrees.

In the first test, the delay time was determined experimentally to be 45 sec and 64 sec for a delay micro-channel having a length of 40 mm and 60 mm, respectively, and a width and depth of 0.25 mm and 0.25 mm, respectively.

In a second test, the delay time was 152 sec, for a delay micro-channel length, width and depth of 57 mm, 0.25 mm, and 0.1 mm, respectively.

In a third test, the delay time was 180 sec, for a delay micro-channel having a first section of length, width and depth of 30 mm, 0.2 mm, and 0.2 mm, respectively, a second section of length, width and depth of 30 mm, 0.1 mm, and 0.1 mm, respectively, and a third section of length, width and depth of 2 mm, 0.35 mm, and 0.25 mm, respectively.

Figure 22:
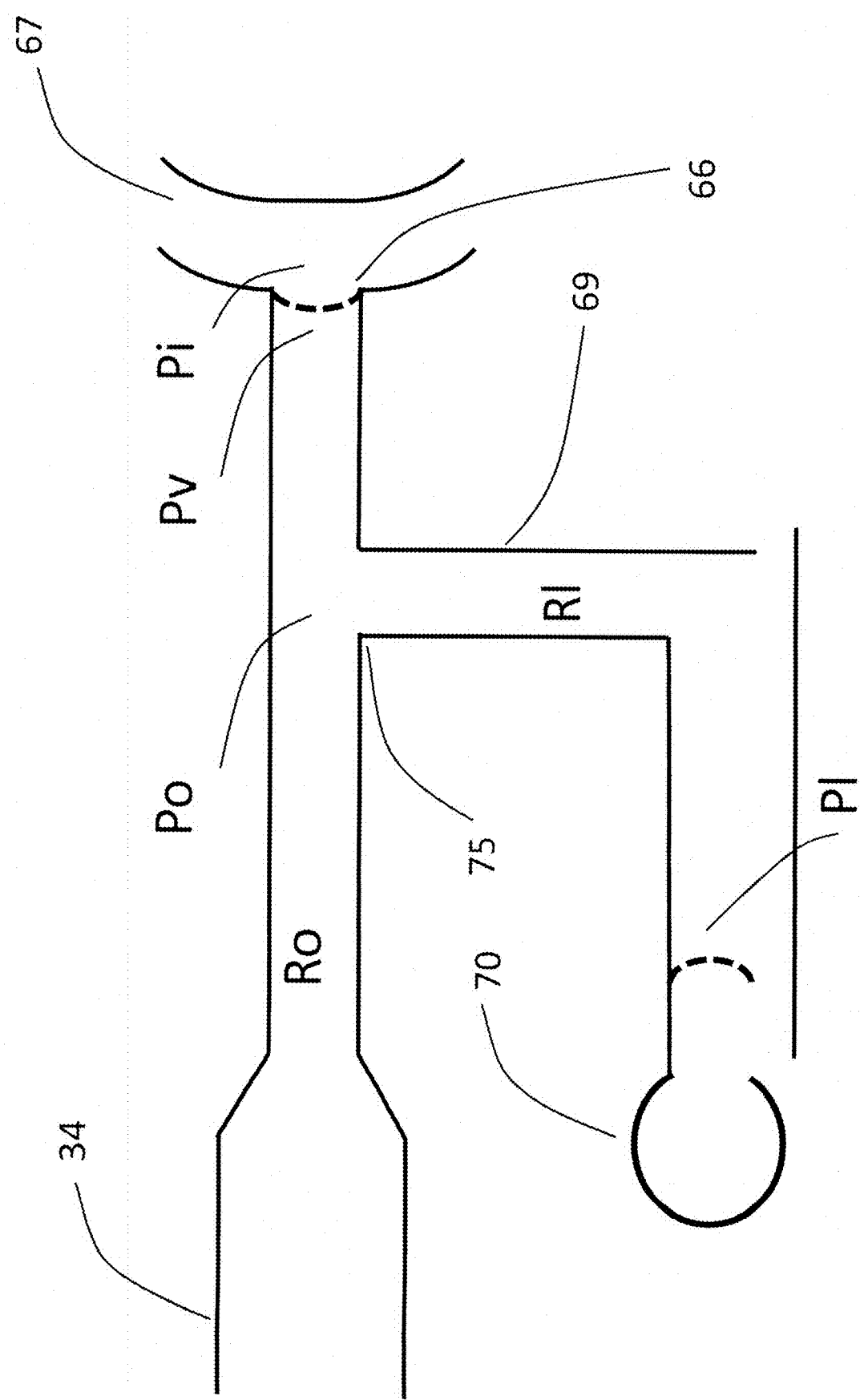
FIG. 22 is a schematic illustration of one reaction chamber, one outlet micro-channel manifold, and one appendix micro-channel. Ro represents the fluid resistance of the sum of the reaction chamber and outlet manifold micro-channel, R1 represents the fluid resistance in the appendix micro-channel, Po represents the pressure at the flow splitter, Pv represents the pressure in the fluid at the fluid meniscus, Pa represents atmospheric pressure at the fluid meniscus, and Pl represents the pressure inside the fluid meniscus in the appendix micro-channel, in accordance with the invention.

Also provided is a method to determine the size of the appendix micro-channels. As shown in FIG. 22, and as previously discussed, the passive valve 66 substantially stops the fluid flow rate to a negligible rate when the Pi>Pv, where Pi is the atmospheric pressure and Pv is the pressure inside the fluid created by the curvature of the meniscus. If the sealing layer is hydrophobic, Pv is always larger than Pi, but if the sealing layer is hydrophilic, then Pv may be smaller than Pi causing the valve to fail (FIG. 22 shows the case of a hydrophilic surface which creates a concave meniscus). By applying well-known hydrodynamic laws of flow in capillary circuits, it is shown that:

$$Pi - Pv = (Pi - Pl)\frac{R_0}{R_o + R_l}, \quad \text{Eq. 24}$$

where Ro and Rl are, respectively, the flow resistance of the reaction chamber and of the delay micro-channel (which can be calculated by using well-known formulae), and $Pl = \gamma \cos(\theta_c)/r_c$, $Pv = 2\gamma \cos(\theta_c)/w_v + \gamma \cos(\theta_c)/h_v - \gamma \cos(\varphi_c)/w_v$ where $\varphi_c$, $w_v$, $h_v$ is the contact angle of the fluid with the sealing layer, and the width and depth of the valve. The size (width, depth, and length) of the appendix micro-channels are chosen such that (Pi−Po)>(Pi−Pv), where (Pi−Pv) is given by Eq. 24, and Po is the pressure at the secondary and primary flow split, and thus provides a pressure gradient at the valve that prevents flow through the valve. The value of Po is approximately given by the ratio of the flow rate of the fluid in the appendix micro-channel over the Rl. The same applies for the computation of the delay micro-channel's size.

Example 8—Conical Sample Inlet

A conical shape inlet with a top opening of 10 mm, a bottom inlet of 1 mm, and height of 5 mm, was fabricated. The inner surface of the inlet was coated with a super-hydrophobic layer with a contact angle of 150 degrees. The inlet then is attached to an embodiment of the microfluidic device described above in paragraph [0049], human plasma was placed inside the inlet, and then the flow rate of the liquid sample, when the fluid reached the graduated columns, was measured and compared to the microfluidic device without a conical inlet. The flow rate without a conical inlet was 0.016 µl/sec, whereas with the conical inlet the flow rate increased to 0.022 µl/sec. Thus, the microfluidic device having a conical inlet in accordance with an embodiment of the present invention resulted in an increased flow rate of about 37%.

Example 9—Micro-Bead Deposition Using a Nano-Dispenser to Distribute Micro-Beads, with Addition of Sucrose and Micro-Bead Layering to Promote Release Depositing micro-beads on the surface of a reaction chamber allows for precise control of micro-bead placement and distribution. As shown in FIG. 23, micro-bead drops 83 are deposited in arrays 92 on the surface of a reaction chamber 34. The arrays 92 can be positioned based on various factors including, but not limited to, different reaction chamber sizes and geometries, micro-bead sizes and concentrations, and antibody affinities. FIG. 23 shows a particular array pattern. Each spot in the array is comprised of several layers of nano-drops. When a single layer of drops containing micro-beads suspended in a 10% sucrose solution is deposited in 5-10 nl drops and dried in a dessicator, less than 50% of the micro-beads are released, i.e., rehydrated, when a liquid sample is added the reaction chamber. When two layers of these drops are deposited on top of each other, greater than 60% of the micro-beads are released upon addition of a liquid sample. When four or more layers of drops are deposited on top of one another, greater than 90% of micro-beads are released when the sample is added.

Example 10—Alteration of Micro-Bead Density to Achieve Neutral Buoyancy and to Prevent Micro-Bead Settling During Micro-Bead Deposition Experiments were conducted to assess the settling of micro-beads in solutions with densities adjusted to achieve neutral buoyancy, and thus prevent micro-beads from settling and the concentration of the micro-bead solution from changing during dispensing. Keeping the micro-beads in a well-mixed suspension is essential to achieve uniformity in micro-bead distribution within and between reaction chambers.

Figure 24:
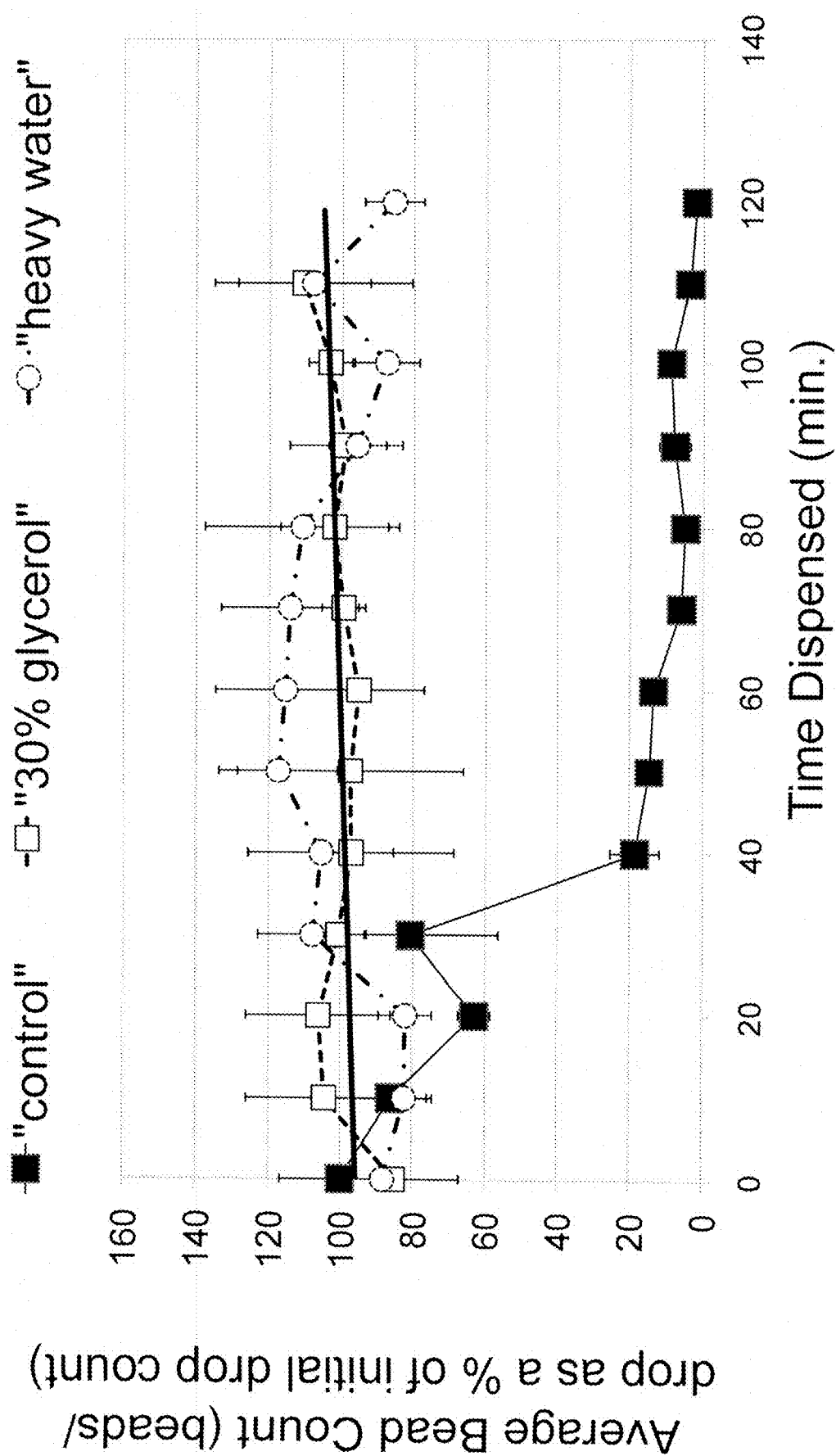
FIG. 24 is a plot of the number of micro-beads per drop deposited on a reaction chamber versus dispensing time. The vertical axis is the average number of micro-beads per drop as a percentage of the number of micro-beads per drop in the first drop deposited at time t=0, and the horizontal axis is the dispensing time.

In an exemplary experiment, suspending micro-beads in a 30% v/v glycerol solution (35% w/v) prevented the micro-beads from settling. Three drops were dispensed every 10 minutes, and micro-beads in each drop were counted. As shown in FIG. 24, micro-bead count in each drop remained constant over a two-hour period. No significant change in micro-bead uniformity was observed in a test tube or in a nano-dispenser reservoir and tubing over the two hour test period. In contrast, in the control where the micro-beads were suspended in 10% sucrose dissolved in water, which has a density lower than the micro-beads, the micro-bead count in each drop decreased by greater than 95% in two hours.

While the addition of glycerol is effective in preventing settling and promoting uniformity in micro-bead deposition, the increased viscosity due to the glycerol may adversely affect the immunoassay. Thus, heavy water (deuterium oxide) was tested for neutral buoyancy suspension of micro-beads for deposition of nano-drops. Micro-beads were suspended in a solution of heavy water (deuterium oxide) mixed with water to achieve a density that matched that of the micro-beads. Sucrose (10%) was added to promote micro-bead release from the reaction chamber surface during the immunoassay. A solution containing between 80-90% heavy water allowed the micro-beads to remain in solution without settling. No significant change in micro-bead uniformity was observed in a test tube or in a nano-dispenser reservoir and tubing over a two hour test period. Micro-bead count in each drop remained relatively constant over the hour period (shown in FIG. 24) with the count at two hours being less than 5% lower than the initial count (compared to a greater than 95% reduction in count in the control). Suspension of micro-beads in a solution containing heavy water (deuterium oxide) allows for uniformity in deposition of micro-beads without affecting the assay performance, since heavy water has the same viscosity and chemical properties as water.

Example 11—Hydrophilic Coating of Micro-Channels to Increase Flow Rate and Decrease Assay Time All micro-channels were coated using a protein-free blocking solution. This coating creates a hydrophilic film on the surface that decreases the fluid contact angle, thus increasing flow rate and decreasing assay times. This coating decreased the contact angle of the PMMA from about 74° to less than about 10°. A liquid sample was placed in the micro-channels through the liquid sample inlet and flow rate was recorded. This coating caused an average increase in flow rate of plasma by 70% (e.g., from 0.016 μl/sec to 0.028 μl/s) and in whole blood by a factor of two (e.g., from 0.005 to 0.01 μl/s) compared to flow of the same sample in uncoated channels of the same dimensions. This increase in flow rate allows the assay time to be reduced by as much as 50%.

Example 12—Flow Rate Variation of Human Whole Blood Through the pScreen™ Immunoassay Device Flow rate of human whole blood, anticoagulated with EDTA, was measured in a pScreen™ immunoassay device (shown in FIG. 18).
The device had the following dimensions:
Inlet manifold micro-channel: width, depth and length between 100 μm-300 μm, 100 μm-300 μm, and 5 mm-15 mm, respectively.
Reaction chambers: width, depth, and length between 120 μm-200 μm, 0.5 mm-3 mm, and 20-40 mm, respectively.
Outlet manifold micro-channels: width, depth and length between 50 μm-300 μm, 50 μm-300 μm, and 5 mm-20 mm, respectively.
Delay micro-channel and appendix micro-channels: width, depth, and length between 50 μm-200 μm, 50 μm-200 μm, and 30 mm-150 mm, respectively.
Test and calibration micro-channels: width, depth and length between 50 μm-200 μm, 50 μm-200 μm, and 5 mm-20 mm, respectively.
The mean flow rate when the fluid meniscus is in the reaction chamber, delay micro-channel or appendix micro-channels, connector micro-channel, and test and calibration micro-channels is between 0.15 μl/sec to 0.25 μl/sec; 0.035 μl/sec to 0.005 μl/sec; 0.12 μl/sec to 0.08 μl/sec, and 0.06 μl/sec to 0.3 μl/sec, respectively.

Example 13—Assay Calibration

Experiments were conducted to assess the sensitivity and dynamic range of the pScreen microfluidic device in quantifying the concentration of DNA fragments in solution.
Buffer 1 was prepared at a final concentration of 1.2 Mole/Liter Acetic Acid ($CH_3COOH$), 1 Mole/Liter sodium chloride (NaCl), and 20% v/v PEG 400, and containing nonmagnetic-responsive silica micro-beads, with size ranging from 1 μm to 9 μm, in a concentration of 30 μg/μL, and magnetic-responsive silica beads in concentration of 1.3 μg/μl. In place of Buffer 2, Monarch® DNA Cleanup Binding Buffer was used, which is a chaotropic salt-based binding buffer containing isopropyl alcohol, guanidine hydrochloride, and sodium Perchlorate.

Figure 27:
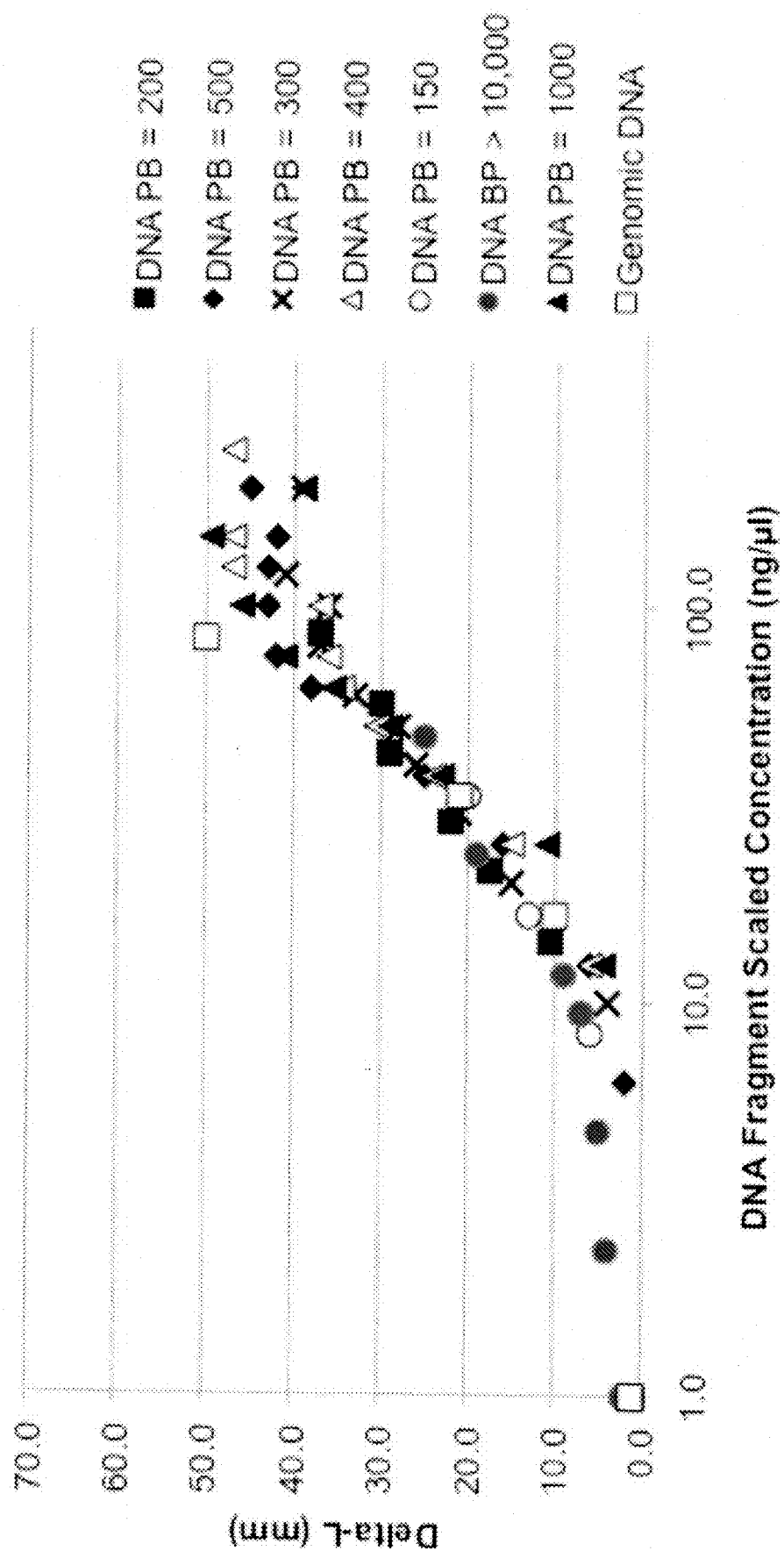
FIG. 27 is a plot of Delta-L (mm) vs DNA Fragment Scaled Concentration obtained for various DNA Fragments lengths from 150 Base Pairs (BPs) to above 10,000 and including genomic DNA.

Samples were prepared my mixing de-ionized water spiked with a known concentration of DNA fragments. Different lengths of DNA fragments were selected ranging from 150 base pairs (BPs) to over 10,000 BPs. First, 5 µL of DNA-containing sample was pipetted into a clean 1.5 mL microcentrifuge tube. Subsequently, 25 µl of Buffer 1 was added to the sample in the 1.5 mL microcentrifuge and mixed by pipetting up and down between 1 and 5 times. The solution was then incubated for 1 minute. Then, 100 µL of Solution 2 was added, and while holding the tube using the thumb and forefinger of one hand, the 1.5 mL microcentrifuge tube was flicked vigorously for 30 seconds using the forefinger of the other hand. Finally, the solution contained in the 1.5 mL microcentrifuge tube (i.e., the sample mixed with Buffer 1 and 2, as above described) was pipetted up and down between 1 and 10 times and transferred into the inlet of the microfluidic device. The test is completed when the liquid in the control column reaches the passive valve, and the flow in the microfluidic card stops. The location where the liquid in the test column stops was recorded, and its distance to the passive valve, Delta-L, plotted against the Scaled Concentration (ng/µl) of the DNA fragments (see FIG. 27). The Scale Concentration is defined as the actual DNA fragment concentration divided by a calibration BP-dependent constant, Cal. The calibration constant, Cal, is experimentally determined so that each Delta-L vs Scale Concentration, for all BPs, collapses as shown in FIG. 27 on the same master curve.

Sample volume used for this set of experiments varied between 1 µl and 5 ul. The dynamic range of the assay with 5 ul input is approx. 5 ng/uL to 30 ng/uL. This can be extended further up to 150 ng/u 1 by lowering sample volume to 1 ul. Accordingly, as shown in FIG. 27, the overall dynamic range is approximately 5 ng/u 1 to 150 ng/ul, thus overlapping with most molecular biology methods. Samples with DNA concentrations exceeding 150 ng/ul can be diluted prior to measurement to avoid saturation, using water or other buffer DNA compatible buffers (e.g. TE buffer).

Example 14—Assay Validation

Figure 28:
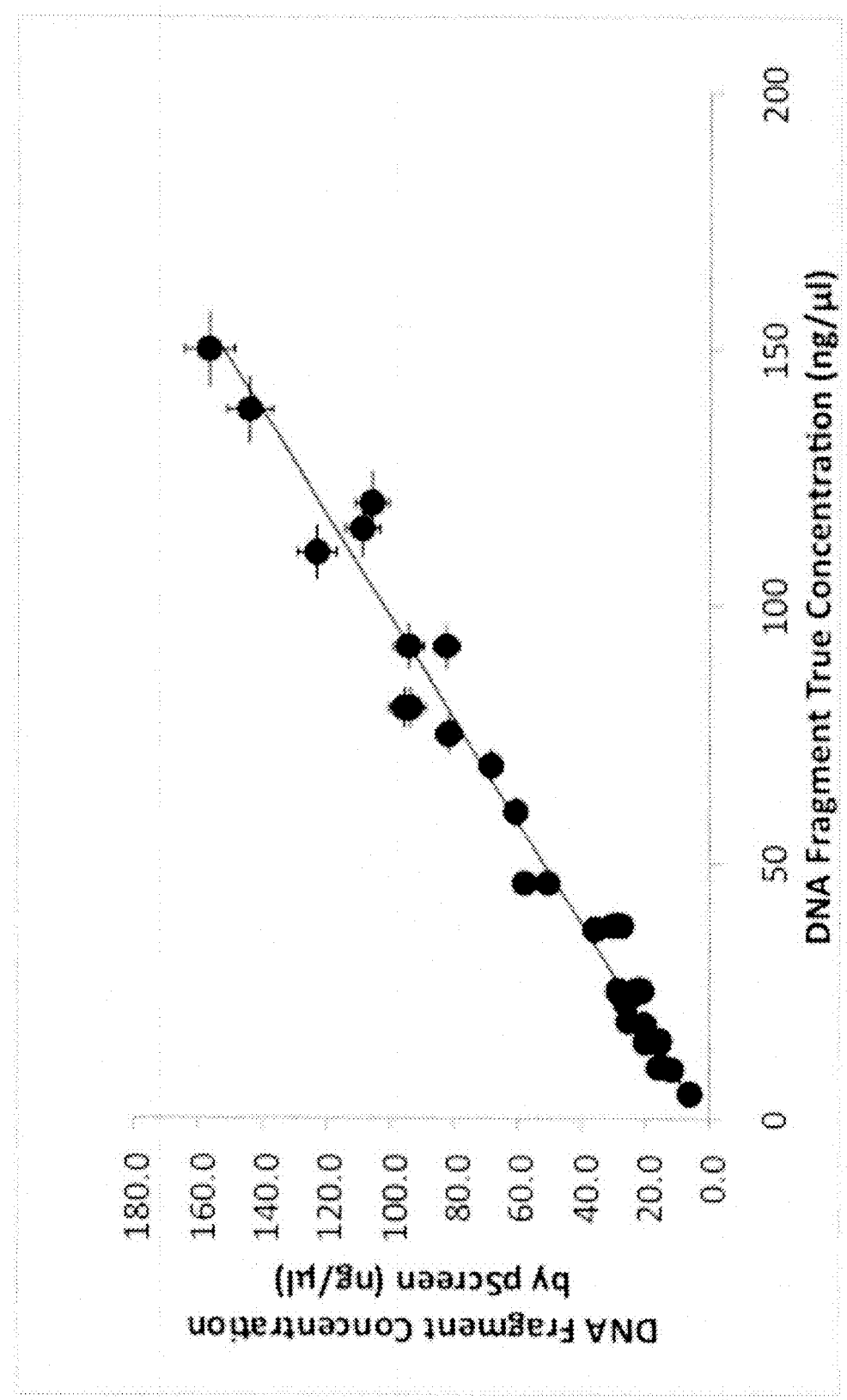
FIG. 28 is a plot of the Concentration of the DNA Fragments (ng/µl) obtained with the p-Screen Device vs. the True Concentration of DNA Fragments.

The assay was validated using multiple DNA sample types, including highly purified NoLimits DNA Fragments (ThermoFisher), fragmented genomic DNA (ThermoFisher), and products generated from standard amplification methods (PCR). FIG. 28 summarizes the results from experiments designed to evaluate the correlation between DNA concentrations of multiple samples measured using the microfluidic device and the same samples analyzed with UV spectrometry (purified DNA) or gel electrophoresis in conjunction with densitometry (unpurified DNA). The validation study was performed using the same Buffer 1 and Buffer 2 as described in Example 13.

Each sample was prepared using Buffer 1 and Buffer 2, and the sample run on the pScreen assay as described above. The resulting Delta-Ls were recorded for each sample, and the scaled concentration of the DNA fragments subsequently was calculated from FIG. 27, by reading the value of the Delta-L on the y-axis of FIG. 27, and recording the correspondent value on the x-axis, i.e., the scaled concentration. Then, using the Cal constant as derived in Example 13, the concentration of DNA fragments was computed by multiplying the scaled concentration by the Cal constant. This process can also be accomplished using an algorithm calculator or, alternatively, using a manual calibration table.

FIG. 28 shows the value of Delta-L as a function of the actual DNA fragment concentration for various concentrations of DNA fragments and fragment size from 150 BPs to over 10,000 BPs. FIG. 28 shows that a high degree of correlation was observed between the concentration of DNA fragments measured by the pScreen assay as described above and the actual (true) DNA concentration. The graph shows a correlation of 1, and a $R^2=0.97$. The standard deviation is about 10%. No significant bias in the results obtained with the pScreen assay was noted with regard to either DNA fragment length or concentration. As it is apparent by examining FIG. 28, one key aspect that makes the microfluidic device an attractive option for DNA quantification is its insensitivity to the interference stemming from the presence of typical PCR reaction components, thereby eliminating the need for separate purification steps. Taken together, the collected data support the notion that the methodology described above combines specificity, sensitivity, speed and cost-effectiveness in a simple and user-friendly procedure which should find multiple applications in the field of molecular biology.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A microfluid device for quantifying the concentration of DNA fragments, comprising:
    a sample inlet defined by an opening for accepting a liquid sample;
    a sealing layer positioned atop the microfluidic device;
    a reaction chamber in continuous fluid connection with the sample inlet;
    a micro-channel splitter in continuous fluid connection with the reaction chamber, said micro-channel bifurcating to form a calibration micro-channel and a test micro-channel;
    a control graduated column in continuous fluid connection with the calibrated micro-channel;
    a test graduated column in continuous fluid connection with the test-micro channel;
    a venting hole located at the end of each of the graduated columns that is placed through the sealing layer; and
    a magnetic field gradient adjacent to the test micro-channel.

2. The microfluid device of claim 1, wherein the liquid sample containing a mixture of magnetic-responsive silica micro-beads, nonmagnetic-responsive silica micro-beads, a chaotropic buffer, and an aliquot of a DNA fragment sample is placed on the inlet of the microfluidic device.

3. The microfluid device of claim 2, wherein the concentration of nonmagnetic-responsive silica micro-beads ranges from between 10 µg/µl and 60 µg/µ in the liquid sample.

4. The microfluid device of claim 2, wherein the concentration of magnetic-responsive silica micro-beads ranges from between 1.0 µg/µl and 3.0 µg/µL in the liquid sample.

5. The microfluid device of claim 1, wherein the presence of DNA fragments triggers the formation of large magnetic-responsive clusters, said magnetic-responsive clusters aggregating in proximity of the magnetic field gradient to produce a localized restriction, said restriction retarding flow of the liquid sample in the test graduated column.

6. The microfluid device of claim 1, wherein the control graduated column and the test graduated column are connected to one another via a joining channel, and a venting hole located at the end of the control column is placed through the sealing layer to stop the flow in the test channel when the liquid flowing in the control column fills to a desired volume.

* * * * *